(12) United States Patent
Blake et al.

(10) Patent No.: US 9,573,899 B2
(45) Date of Patent: Feb. 21, 2017

(54) USP7 INHIBITOR COMPOUNDS AND METHODS OF USE

(71) Applicant: Genentech, Inc., South San Francisco, CA (US)

(72) Inventors: Robert Blake, South San Francisco, CA (US); Paola Di Lello, South San Francisco, CA (US); Jason Drummond, South San Francisco, CA (US); Christine Johanna Heideker, South San Francisco, CA (US); Lorna Kategaya, South San Francisco, CA (US); Till Maurer, South San Francisco, CA (US); Jeremy M. Murray, South San Francisco, CA (US); Chudi Ndubaku, South San Francisco, CA (US); Richard Pastor, South San Francisco, CA (US); Lionel Rouge, South San Francisco, CA (US); Vickie Tsui, Burlingame, CA (US); Ingrid E. Wertz, South San Francisco, CA (US); Kebing Yu, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/074,027

(22) Filed: Mar. 18, 2016

(65) Prior Publication Data
US 2016/0272588 A1 Sep. 22, 2016

Related U.S. Application Data

(60) Provisional application No. 62/135,846, filed on Mar. 20, 2015.

(51) Int. Cl.
| | | |
|---|---|---|
| C07D 213/02 | (2006.01) | |
| C07D 213/73 | (2006.01) | |
| A61K 31/44 | (2006.01) | |
| A61K 45/06 | (2006.01) | |
| C07D 409/04 | (2006.01) | |
| A61K 31/4436 | (2006.01) | |
| A61K 31/5355 | (2006.01) | |
| C07D 401/04 | (2006.01) | |
| A61K 31/444 | (2006.01) | |
| A61K 31/506 | (2006.01) | |
| A61K 31/496 | (2006.01) | |
| A61K 31/4439 | (2006.01) | |
| C07D 213/74 | (2006.01) | |
| C07D 403/04 | (2006.01) | |

(52) U.S. Cl.
CPC .......... *C07D 213/73* (2013.01); *A61K 31/44* (2013.01); *A61K 31/444* (2013.01); *A61K 31/4436* (2013.01); *A61K 31/4439* (2013.01); *A61K 31/496* (2013.01); *A61K 31/506* (2013.01); *A61K 31/5355* (2013.01); *A61K 45/06* (2013.01); *C07D 213/74* (2013.01); *C07D 401/04* (2013.01); *C07D 403/04* (2013.01); *C07D 409/04* (2013.01)

(58) Field of Classification Search
CPC ..................................................... C07D 213/02
USPC ......................................................... 546/255
See application file for complete search history.

(56) References Cited

U.S. PATENT DOCUMENTS

8,802,866 B2 * 8/2014 Emde ................ A61K 31/4178
548/314.7

FOREIGN PATENT DOCUMENTS

| WO | 2012/121939 A2 | 9/2012 |
| WO | 2013/162061 A1 | 10/2013 |

OTHER PUBLICATIONS

Colland et al., "Small-molecule inhibitor of USP7/HAUSP ubiquitin protease stabilizes and activates p53 in cells" Mol Cancer Ther. 8(8):2286-95 ( 2009).
Database Registry CAS Reg. No. 1259479-70-3 Jan. 17, 2011.
Database Registry CAS Reg. No. 1261684-65-4; 1261651-69-7; 1261635-29-3; 1261568-53-9; 1261454-30-1; 1261436-81-0 Feb. 2, 2011.
Database Registry CAS Reg. No. 1261870-37-4 Feb. 3, 2011.
Database Registry CAS Reg. No. 1361605-03-9; 1361583-94-9; 1361565-02-7; 1361558-84-0; 1361498-43-2; 1361479-27-7 Mar. 22, 2012.
Database Registry CAS Reg. No. 131862-20-5; 1361823-67-7; 1361804-33-2; 1361748-00-6; 1361694-12-3; 1361650-05-6 Mar. 23, 2012.

(Continued)

*Primary Examiner* — Niloofar Rahmani
(74) *Attorney, Agent, or Firm* — Alex Andrus

(57) ABSTRACT

2-Aminopyridine compounds of Formula I are provided, and various substituents including stereoisomers, tautomers, and pharmaceutically acceptable salts thereof, useful for modulating USP7, and for treating cancer and immune disorders such as inflammation mediated by USP7. Methods of using compounds of Formula I for in vitro, in situ, and in vivo diagnosis, and treatment of such disorders in mammalian cells, or associated pathological conditions, are disclosed.

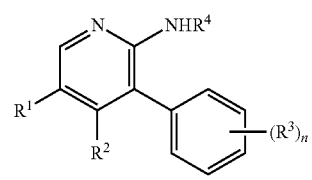

I

12 Claims, 23 Drawing Sheets

(56) References Cited

OTHER PUBLICATIONS

Guedat et al., "Patented small molecule inhibitors in the ubiquitin proteasome System" BMC Biochemistry 8( SUPPL 1)::S14:1-12 ( 2007).
Heideker et al., "DUBs, the regulation of cell identify and disease" Biochemical Journal 465(1):1-26 ( 2015).
ISR for PCT/EP2016/055744, WO2016/150800.
Lill et al., "Toward understanding ubiquitin-modifying enzymes: from pharamcological targeting to proteomics" Trends in Pharmacological Sciences 35(4):187-207 (Apr. 2014).
Reverdy et al., "Discovery of Specific Inhibitors of Human USP7/HAUSP Deubiquitinating Enzyme" Chemistry & Biology 19(4):467-477 ( 2012).
Ritorto et al., "Screening of DUB activity and specificity by MALDI-TOF mass spectrometry" Nature Communications 5:4763-73 ( 2014).
Vucic et al., "Ubiquitylation in apoptosis: a post-translational modification at the edge of life and death" Nat Rev Mol Cell Biol. 12(7):439-452 ( 2011).
Zhang et al., "Confromational stabilization of ubiquitin yields potent and selective inhibitors of USP7" Nature Chemical Biology 9(1):51-58 ( 2013).

\* cited by examiner

Cells were treated with 15μM compounds 88 and 89 for <24h in low serum

* indicates statistical significance between inactive and active compound (n = 3)

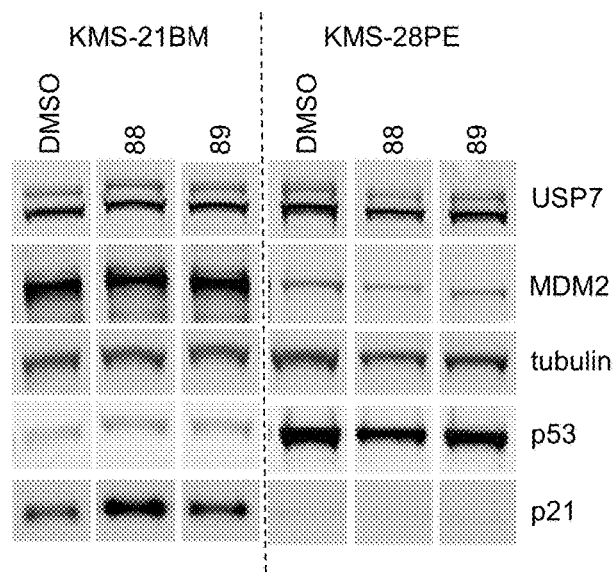
*Fig. 13B*
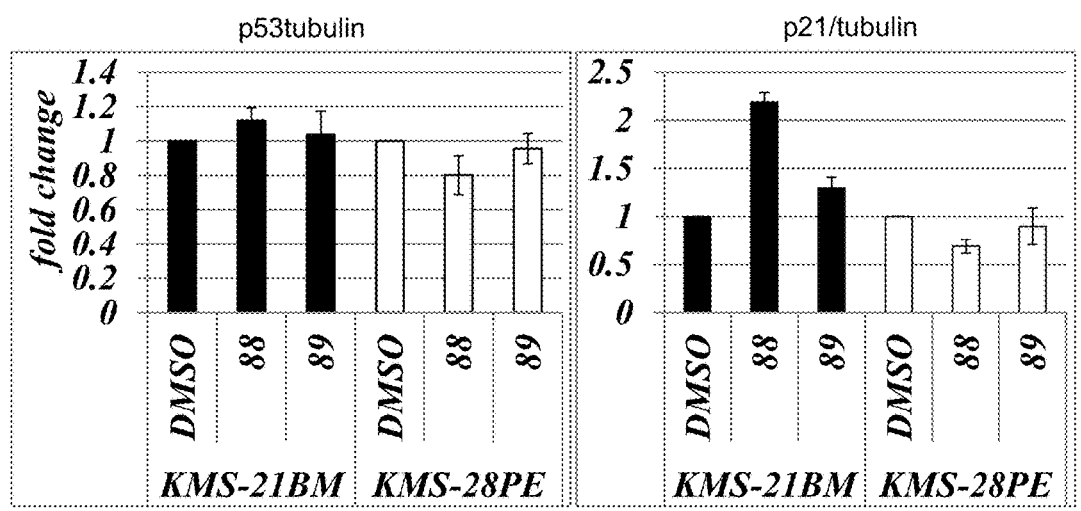
*Fig. 13C*  *Fig. 13D*

USP7 INHIBITOR COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 62/135,846 filed on 20 Mar. 2015, which is incorporated by reference in entirety.

FIELD OF THE INVENTION

The invention relates generally to compounds for treating disorders mediated by USP7 including inflammation, immunological, and cancer, and more specifically to compounds which inhibit or modulate USP7 activity or function. The invention also relates to methods of using the compounds for in vitro, in situ, and in vivo diagnosis or treatment of mammalian cells, or associated pathological conditions.

BACKGROUND OF THE INVENTION

Ubiquitin, a small protein that acts as a post-translational mark on other proteins, has a surprising amount of conformational heterogeneity (Lange, O. F. et al. (2008) Science 320, 1471-1475). Protein ubiquitination mediates numerous cellular processes, such as cell cycle control, apoptosis, epigenetics and transcriptional regulation (Clague, M. J. et al (2010) Cell 143:682-685). The C terminus of ubiquitin is covalently attached to a lysine or the N terminus of a substrate protein through the coordinated action of three classes of enzymes: an E1 activator, an E2 conjugator and ubiquitin ligase (ubiquitin E3) (Pickart, C. M. (2001) Annu. Rev. Biochem. 70:503-533). Each of the seven lysines or the N terminus of ubiquitin can also serve as a substrate for further ubiquitination, allowing the polymerization of ubiquitin chains with linkages that convey a wealth of information (Pickart, C. M. et al (2004) Curr. Opin. Chem. Biol. 8:610-616). Motions within the $\beta 1$-$\beta 2$ loop of ubiquitin have been implicated in its recognition by partner proteins, though it is currently unknown how the conformational state of apo ubiquitin is 'read' by each partner. The multiple conformations of apo ubiquitin could represent a compromise that allows its single protein surface to bind a wide variety of unrelated partners with moderate affinity (Humphris, E. L. et al (2007) PLoS Comput. Biol. 3, e164 (2007); Friedland, G. D., et al (2009) PLoS Comput. Biol. 5, e1000393).

Deubiquitinases (DUBs) are a class of specialized proteases that regulate ubiquitin-mediated signaling by disassembling ubiquitin chains or removing monoubiquitination from substrates (Heideker, J. and Wertz, I. E. (2015) Biochem. J. 465:1-26; Lill, J. R. and Wertz, I. E. (2014) Trends in Pharm. Sci. 35(4):187-207; Komander, D., et al (2009) Nat. Rev. Mol. Cell Biol. 10:550-563). There are approximately 100 identified human DUBs, the majority of which await extensive investigation. One exception is USP7 (also known as HAUSP), a ubiquitin-specific protease (USP) which has an established role in tumorigenesis via its action on Mdm2, p53, FOXO4 and PTEN (Nicholson, B. et al (2011) Cell Biochem. Biophys. 60:61-68); Hussain, S., et al (2009) Cell Cycle 8:1688-1697). Although the determination of USP7's precise function in certain pathways has been complicated by conflicting reports (Li, M., et al (2004) Mol. Cell 13:879-886); Li, M. et al. (2002) Nature 416:648-653), this enzyme's participation in many cancer related processes has made it an attractive therapeutic target.

Despite its cellular importance, the catalytic core of USP7 is unexpectedly inactive, with a catalytic efficiency ($k_{cat}/K_m$) around 103 M-1 s-1 and an affinity (KD) for ubiquitin of several hundred micromolar (Faesen, A. C. et al. (2011) Mol. Cell 44:147-159); Fernández-Montalván, A. et al. (2007) FEBS J. 274, 4256-4270). The conformationally heterogeneous $\beta 1$-$\beta 2$ loop is directly contacted by all DUBs, including USP7. Hence, it is sought to determine whether stabilizing a USP7-binding conformation of ubiquitin's $\beta 1$-$\beta 2$ region could yield variants with a high affinity for the target DUB. Given USP7's role in cell division and technical difficulties surrounding USP7 knockdown, a conformationally optimized, ubiquitin-based inhibitor with high affinity and specificity for USP7 could prove a potent tool for understanding USP7's cellular functions. In a related approach, surface engineering of ubiquitin was used to generate potent binders of ubiquitin-signaling enzymes (Ernst et al, Science doi:10.1126/science. 1230161 (3 Jan. 2013); Zhang, Y., et al (2013) Nature Chemical Biology 9(1):51-58).

USP7 or HAUSP (herpesvirus-associated USP) is a ubiquitin specific protease or a deubiquitylating enzyme that cleaves ubiquitin from its substrates (Holowaty M N, et al (2003) J. Biol. Chem. 278 (48):47753-47756). Since ubiquitylation (polyubiquitination) is most commonly associated with the stability and degradation of cellular proteins, HAUSP activity generally stabilizes its substrate proteins. HAUSP is most popularly known as a direct antagonist of Mdm2, the E3 ubiquitin ligase for the tumor suppressor protein, p53 (Li M, et al (2002) Nature 416 (6881): 648-53). Normally, p53 levels are kept low in part due to Mdm2-mediated ubiquitylation and degradation of p53. In response to oncogenic insults, HAUSP can deubiquitinate p53 and protect p53 from Mdm2-mediated degradation, indicating that it may possess a tumor suppressor function for the immediate stabilization of p53 in response to stress. Another important role of HAUSP function involves the oncogenic stabilization of p53. Oncogenes such as Myc and E1A are thought to activate p53 through a p19 alternative reading frame (p19ARF, also called ARF)-dependent pathway, although some evidence suggests ARF is not essential in this process. A possibility is that HAUSP provides an alternative pathway for safeguarding the cell against oncogenic insults.

USP7 is a DUB that controls cell proliferation by altering the stability of Mdm2, p53, PTEN and FOXO4. Despite USP7's importance in tumor-related pathways, relatively little is known about its cellular and biochemical regulation, and there has been some confusion about its precise role in the Mdm2-p53 axis, in part because of a lack of inhibitory tools. The catalytic domain of USP7 is relatively inefficient in vitro, with a nearly undetectable affinity for its ubiquitin substrate and relatively poor catalytic efficiency. The C terminus and the fourth and fifth Ubl domains of USP7 greatly increase its activity via a combination of increased kcat and decreased Km, though the mechanism by which these effects are achieved is currently unknown. Engineering of ubiquitin conformation can greatly increase its interaction with deubiquitinases such as USP7 (Zhang, Y., et al (2013) Nature Chemical Biology 9(1):51-58).

Deregulation of the ubiquitin/proteasome system (UPS) has been implicated in the pathogenesis of many human diseases, including cancer (Vucic, D., et al (2011) Nature Reviews Molecular Cell Biology 12:439-452). Ubiquitin-specific proteases (USP) are cysteine proteases involved in the deubiquitination of protein substrates. Functional connections between USP7 and essential viral proteins and oncogenic pathways, such as the p53/Mdm2 and phosphatidylinositol 3-kinase/protein kinase B networks, strongly suggest that the targeting of USP7 with small-molecule inhibitors may be useful for the treatment of cancers and viral diseases.

Therapeutic agents that target apoptotic regulatory proteins that are part of the ubiquitin-proteasome system, might afford clinical benefits (Vucic, D., et al (2011) Nature Reviews Molecular Cell Biology 12:439-452). Deubiquitinase inhibitors and antagonists have been reported (Lill, J. R. and Wertz, I. E. (2014) Trends in Pharm. Sci. 35(4):187-207, see Table 2, page 195, Ndubaku, C. and Tsui, V. (2015) J. Med. Chem. DOI:10.1021/jm501061a). The rationale for targeting the ubiquitin-proteasome system for the treatment of cancer is validated by FDA approval, and the clinical efficacy, of bortezomib (VELCADE®; Millennium Pharmaceuticals) for the treatment of multiple myeloma and mantle cell lymphoma. Phenotypes associated with USP7 silencing strongly suggest that small molecule inhibitors of USP7 may have the potential for antiviral and anticancer therapies (Li, M. et al. (2002) Nature 416:648-653; Daviet, L. and Colland, F. (2008) Biochimie 90:270-283).

SUMMARY OF THE INVENTION

The invention relates generally to 2-aminopyridine compounds with USP7 modulating activity or function having the Formula I structure:

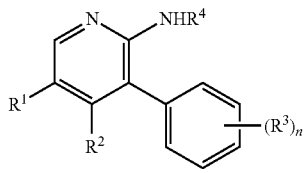

including stereoisomers, tautomers, or pharmaceutically acceptable salts thereof. The various substituents are defined herein.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by USP7.

The invention includes a kit for treating a condition mediated by USP7, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by USP7.

The invention includes a Formula I compound for use in combination with an additional therapeutic agent in treating a disease or disorder.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates USP7.

The invention includes methods of making a Formula I compound.

BRIEF DESCRIPTION OF THE DRAWINGS

FIG. 13B shows western blot data indicating that the active compound 88 compared to 89 increases p21 levels in KMS-21BM and KMS-28PE multiple myeloma cells.

FIG. 13C shows a plot of p53/tubulin change in KMS-21BM and KMS-28PE multiple myeloma cells treated with compounds 88 and 89.

FIG. 13D shows a plot of p21/tubulin change in KMS-21BM and KMS-28PE multiple myeloma cells treated with compounds 88 and 89.

DETAILED DESCRIPTION OF EXEMPLARY EMBODIMENTS

Figure 1A:
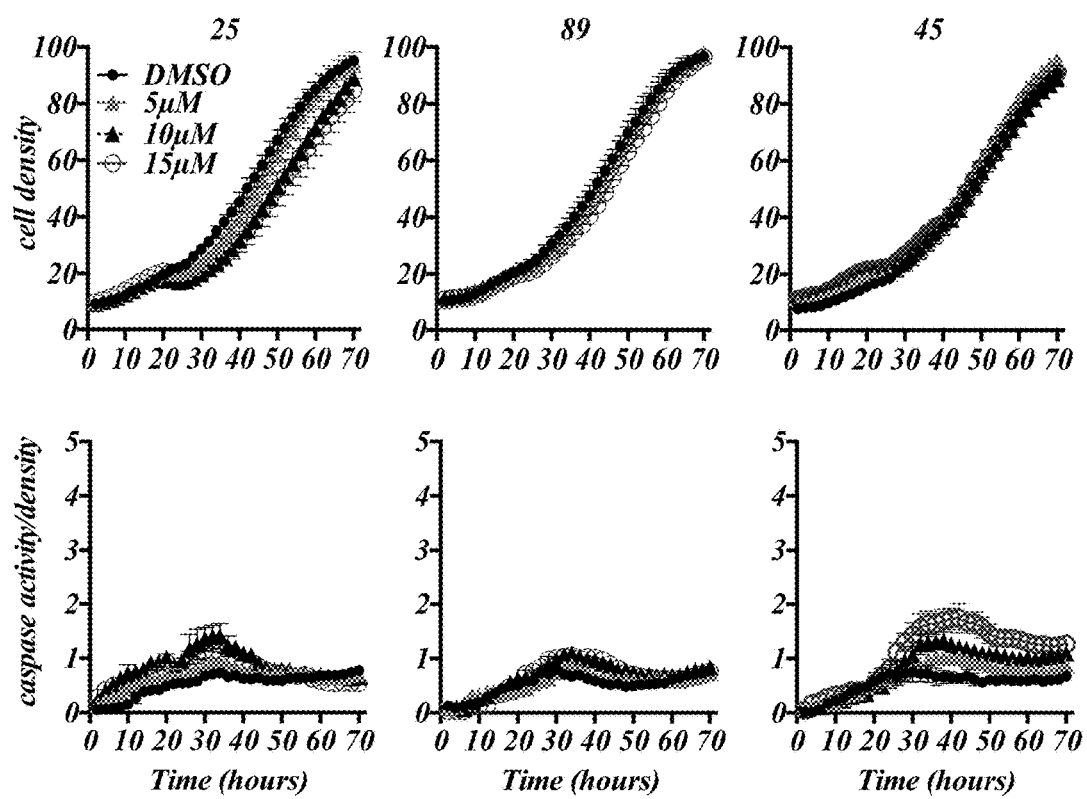
FIG. 1A shows cellular proliferation and caspase activity (Incucyte®, Essen Bioscience) data of compounds 25, 89 and 45 in HCT116 colon cancer cells.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indenylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (formerly CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (-log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (-log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

2-Aminopyridine Compounds

The present invention provides 2-aminopyridine compounds of Formula I, including Formulas Ia-If, and pharmaceutical formulations thereof, which are potentially useful in the treatment of diseases, conditions and/or disorders modulated by USP7. Dysregulation of the ubiquitin proteasome system (UPS) has been associated with disease pathogenesis, including several types of cancer. In particular, ubiquitin-specific protease 7 (USP7), a cysteine protease belonging to the deubiquitinase (DUB) family, has been shown to be a critical regulator of p53.

Compounds which modulate USP7 may be identified and assessed by the NMR fragment screen methodology of Example 907. Utilizing fragment-based screening by NMR, 2-aminopyridine compounds of Formula I were shown to bind to the enzyme active site by X-ray crystallography. Using shape-based virtual screening combined with NMR site-mapping, Formula I compounds were found that bound to an adjacent site, known as the Palm site. Crystallography-guided design led to novel inhibitors that are selective for USP7 over other DUBs, show activity in multiple tumor cell lines and demonstrate expected p53/Mdm2 biology.

Formula I compounds have the structure:

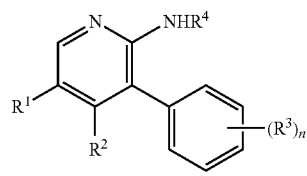

I or stereoisomers, tautomers, or pharmaceutically acceptable salts thereof, wherein:

$R^1$ is selected from $C_6$-$C_{20}$ aryl, $C_3$-$C_{12}$ carbocyclyl, $C_2$-$C_{20}$ heterocyclyl, and $C_1$-$C_{20}$ heteroaryl;

$R^2$ is selected from —CN, —OCH3, $C_1$-$C_3$ alkyl, $C_1$-$C_3$ fluoroalkyl, and cyclopropyl;

$R^3$ is selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;

n is selected from 0, 1, 2, and 3; and $R^4$ is selected from H, $C_1$-$C_3$ alkyl, $C_1$-$C_3$ fluoroalkyl, cyclopropyl, and cyclopropylmethyl;

where aryl, carbocyclyl, heterocyclyl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

Exemplary embodiments of Formula I compounds include wherein $R^1$ is optionally substituted $C_6$-$C_{20}$ aryl.

Exemplary embodiments of Formula I compounds include wherein $R^1$ is 4-phenol

Exemplary embodiments of Formula I compounds include wherein $R^1$ is optionally substituted $C_1$-$C_{20}$ heteroaryl.

Exemplary embodiments of Formula I compounds include wherein $R^1$ is selected from 1H-indazol-5-yl, 1H-indazol-6-yl, 2-methylindazol-4-yl, 1H-benzimidazol-5-yl, 2-thienyl, pyrimidin-5-yl, 3-pyridyl, 4-pyridyl, and 1H-pyridin-2-one.

Exemplary embodiments of Formula I compounds include wherein $R^2$ is —CH$_2$CH$_3$.

Exemplary embodiments of Formula I compounds include wherein $R^3$ is —OH, and n is 1.

Exemplary embodiments of Formula I compounds include wherein $R^4$ is H.

Exemplary embodiments of Formula I compounds include compounds of Formulas Ia-f:

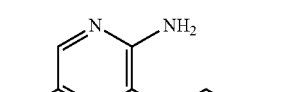

Ia

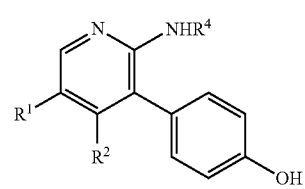

Ib

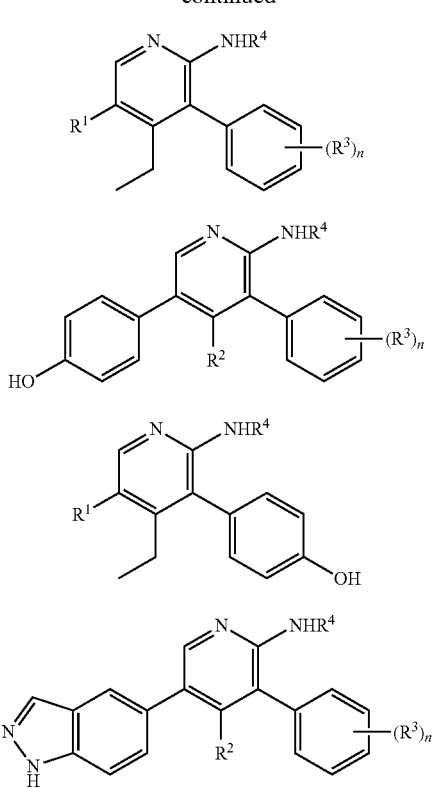

Exemplary embodiments of Formula I compounds include the compounds in Table 1.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

The ubiquitin-intein-His6 expression vector was cloned according to the methods of Example 901 to provide Ubiquitin-Rhodamine 110-Glycine for screening the compounds of the invention Formula I compounds were tested by a standard biochemical USP7 enzymatic Assay (Example 902).

Example 903 measures activity-based enrichment of deubiquitinase enzymes (DUBs).

Example 904 measures in-gel tryptic digestion and mass spectroscopy analysis.

Example 905 provides methodology for data analysis and bioinformatics.

Examples 903-905 are collectively used to evaluate the selectivity of compounds to antagonize the activity of endogenous DUBs that are detected in an activity-based profiling assay.

Example 906 provides cellular data methods: Cell viability assays (Incucyte, Cell Titer Glo), MDM2 turnover, and western blots of proteins that participate in USP7-regulated signaling pathways are collectively used to evaluate the molecular and the cellular mechanisms of action of USP7 antagonists.

The methods elucidate a unique mechanism to inhibit USP7 catalytic activity, that may be applicable to antagonizing other deubiquitinases.

Formula I compounds can be screened for DUB activity and specificity by MALDI-TOF mass spectrometry (Ritorto, M. S., et al (2014) Nature Communications 5:4763; doi: 10.1038).

Cell proliferation, cytotoxicity, and cell viability of the Formula I compounds can be measure by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

FIG. 1A shows cellular proliferation and caspase activity (Incucyte®, Essen BioScience) data of compounds 25, 89 and 45 in HCT116 colon cancer cells.

Figure 1B:
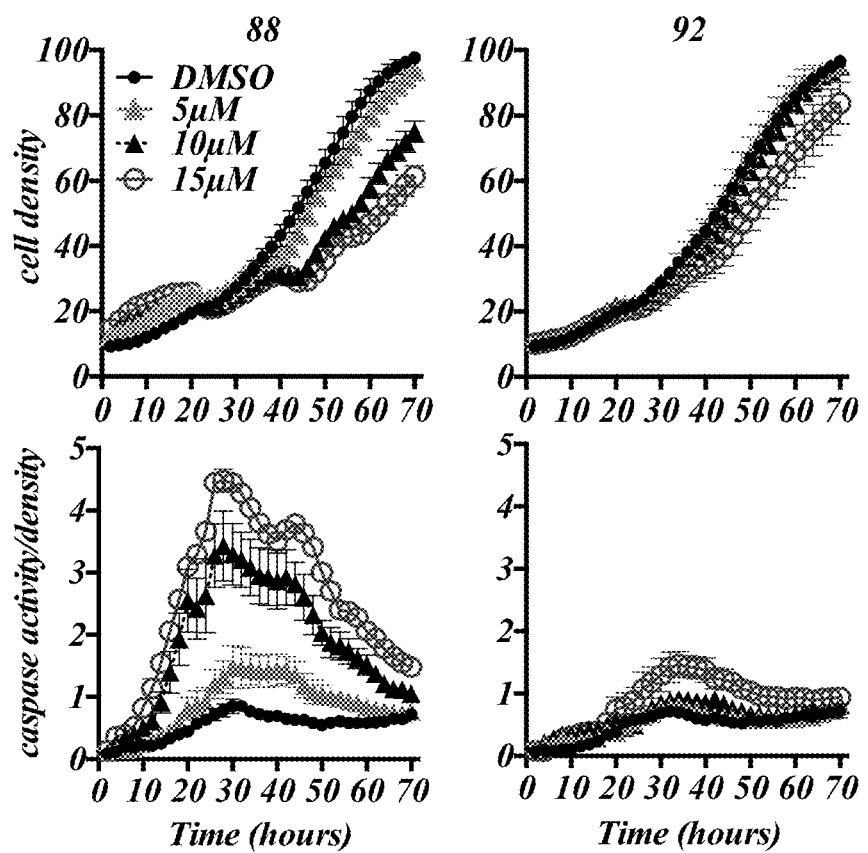
FIG. 1B shows cellular proliferation and caspase activity (Incucyte®, Essen BioScience) data of compounds 88 and 92 in HCT116 colon cancer cells.

FIG. 1B shows cellular proliferation and caspase activity (Incucyte®, Essen BioScience) data of compounds 88 and 92 in HCT116 colon cancer cells.

Figure 2A:
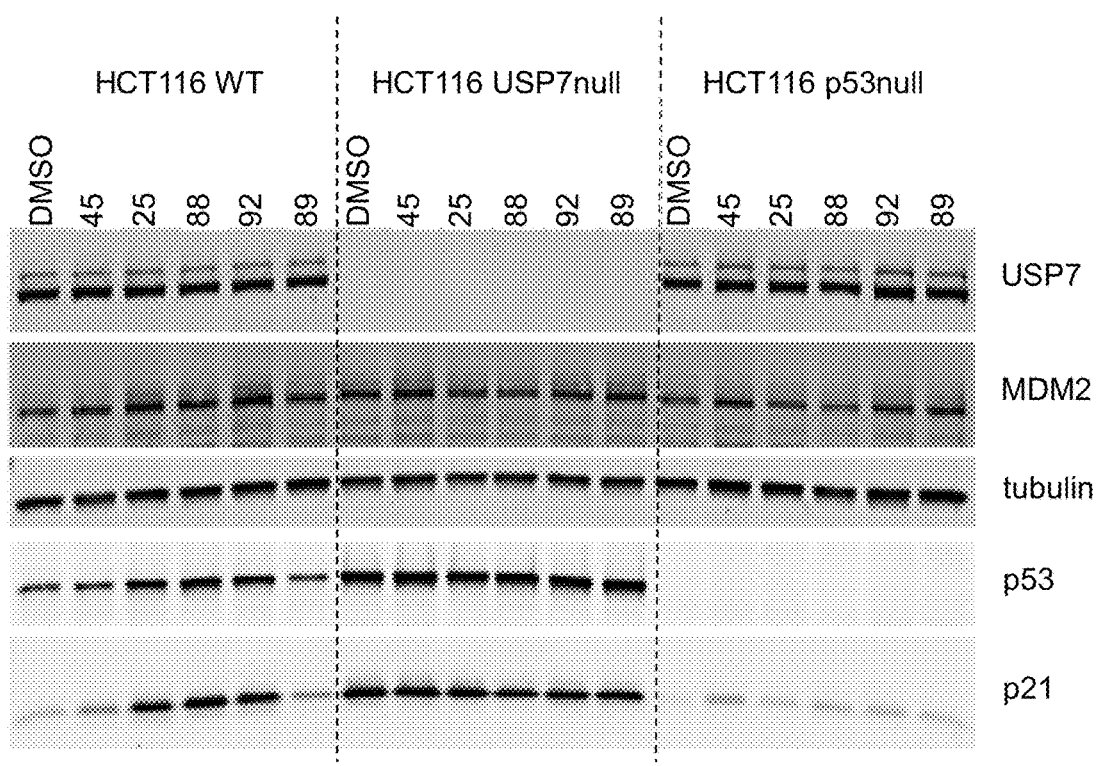
FIG. 2A shows western blot data indicating that active Palm compounds 25, 88, 92, but not compounds 45 and 89, stabilize p53 and p21 in a p53- and in a USP7-dependent manner in isogenic HCT116 colon cancer cell lines (wild-type (WT), USP7 null, and p53 null, respectively).

FIG. 2A shows western blot data indicating that active Palm compounds 25, 88, 92, but not inactive control compounds 45, 89 stabilize p53 and p21 in a p53- and in a USP7-dependent manner in isogenic HCT116 colon cancer cell lines (wild-type, USP7 null, and p53 null, respectively).

Figure 2B:
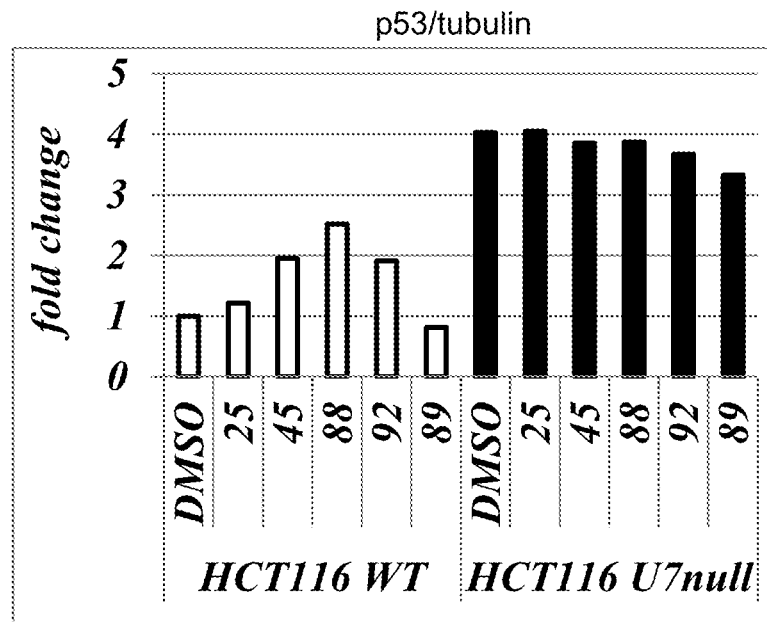
FIG. 2B shows a plot of p53/tubulin change in HCT116 colon cancer cell lines (wild-type and USP7 null) treated with compounds 45, 25, 88, 92, 89.

FIG. 2B shows a plot of p53/tubulin change in HCT116 colon cancer cell lines (wild-type and USP7 null) treated with compounds 45, 25, 88, 92, 89.

Figure 2C:
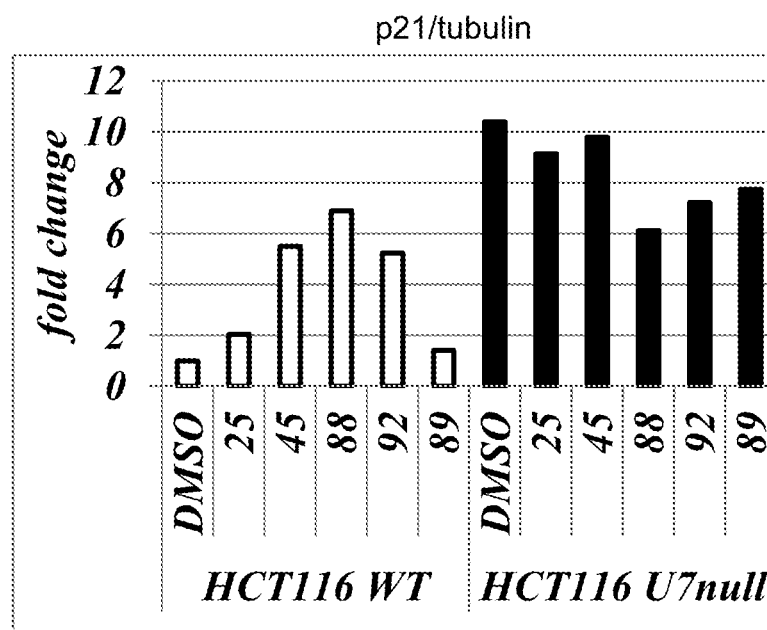
FIG. 2C shows a plot of p21/tubulin change in HCT116 colon cancer cell lines (wild-type and USP7 null) treated with compounds 45, 25, 88, 92, 89.

FIG. 2C shows a plot of p21/tubulin change in HCT116 colon cancer cell lines (wild-type and USP7 null) treated with compounds 45, 25, 88, 92, 89.

Figure 3A:
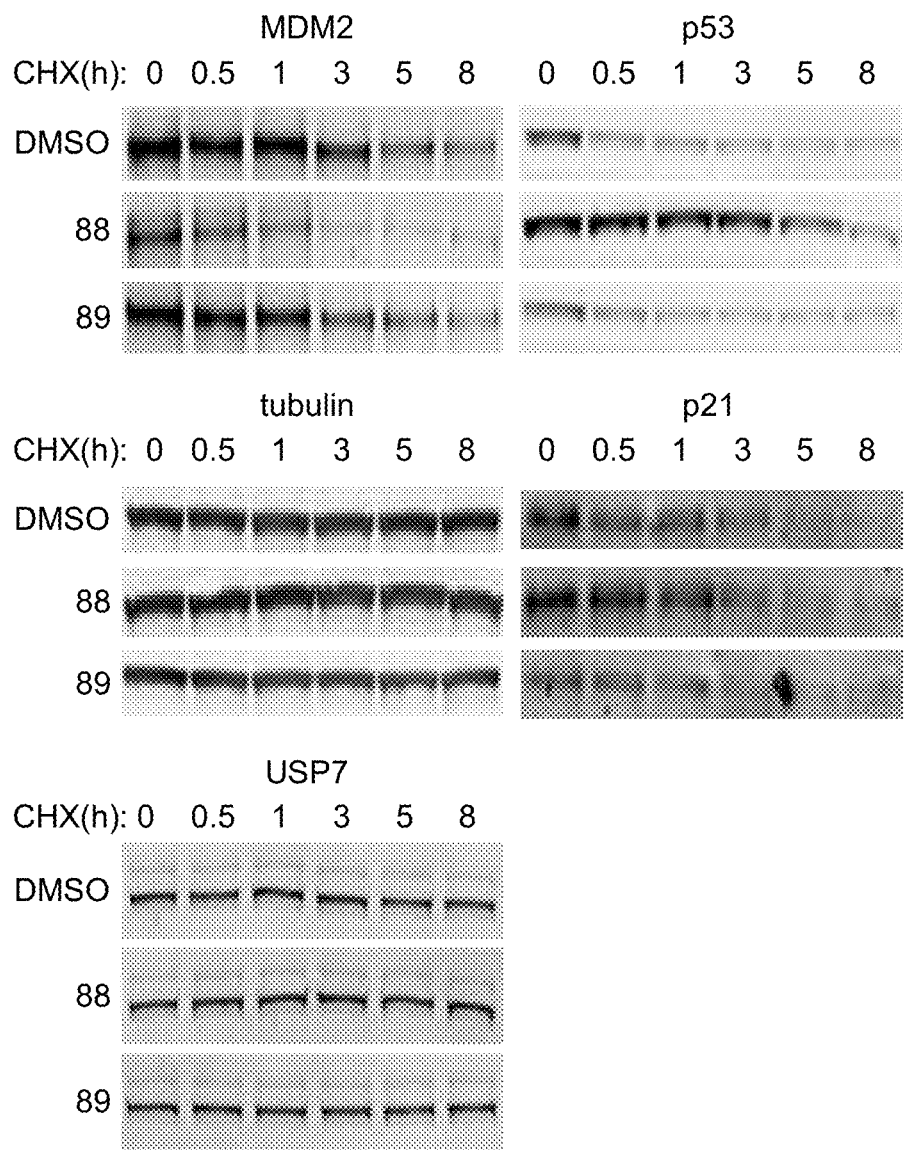
FIG. 3A shows western blot data indicating the destabilizing effects of compound 88 versus less active compound 89 (15 µM) on MDM2, tubulin, USP7, p53 and p21 in MCF7 breast cancer cells in the presence of cycloheximide (CHX).

FIG. 3A shows western blot data indicating the destabilizing effects of active compounds 88 versus less active compound 89 (15 µM) on MDM2, tubulin, USP7, p53 and p21 in MCF7 breast cancer cells.

Figure 3B:
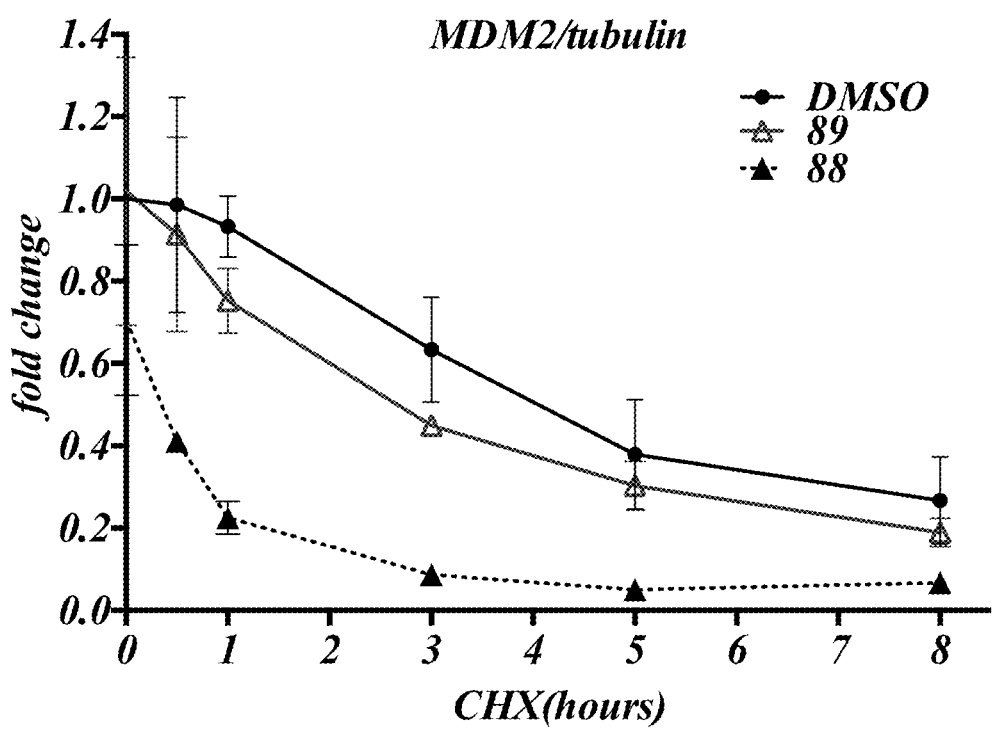
FIG. 3B shows a plot of quantitated MDM2/tubulin in cells treated with compounds 88 and 89 in the presence of cycloheximide (CHX).

FIG. 3B shows a plot of MDM2/tubulin in cells treated with compounds 88 and 89

Figure 4:
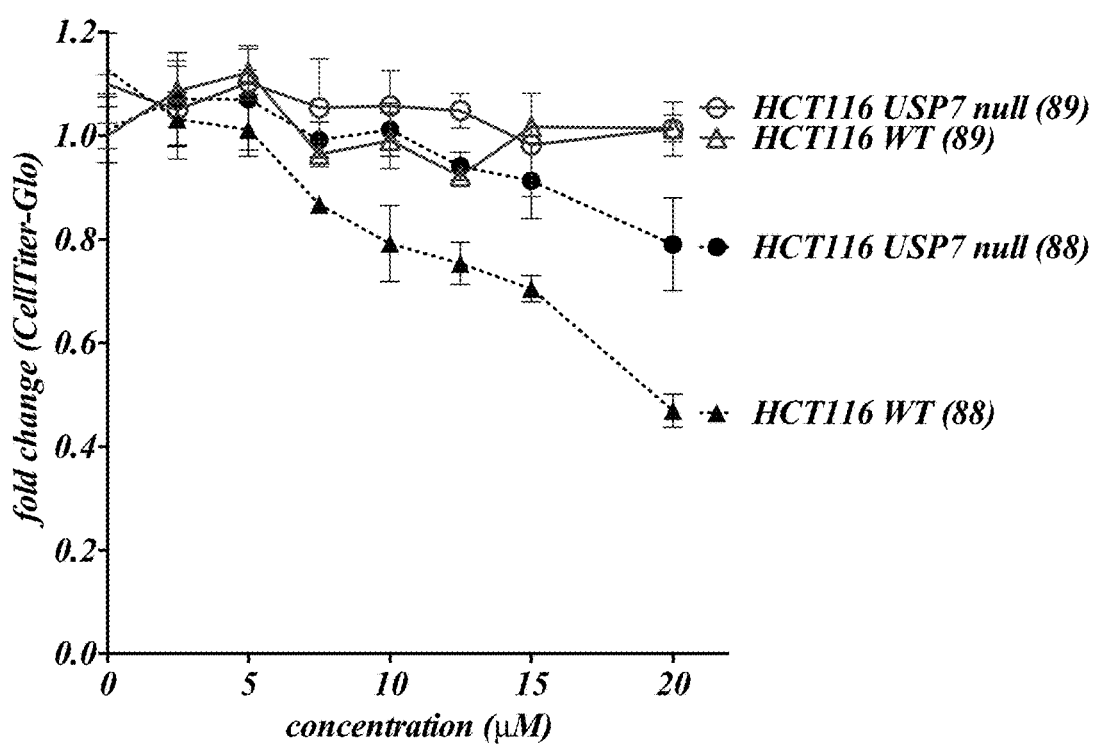
FIG. 4 shows a plot of the effects of cell viability in a USP7-dependent manner by compounds 88 and 89 on HCT116 cells (wild type and USP7 null), indicating a USP7-dependent decrease in viability.

FIG. 4 shows a plot of the effects of cell viability in a USP7-dependent manner by compounds 88 and 89 on HCT116 cells (wild type and USP7 null), indicating a USP7-dependent decrease in viability.

Figure 5:
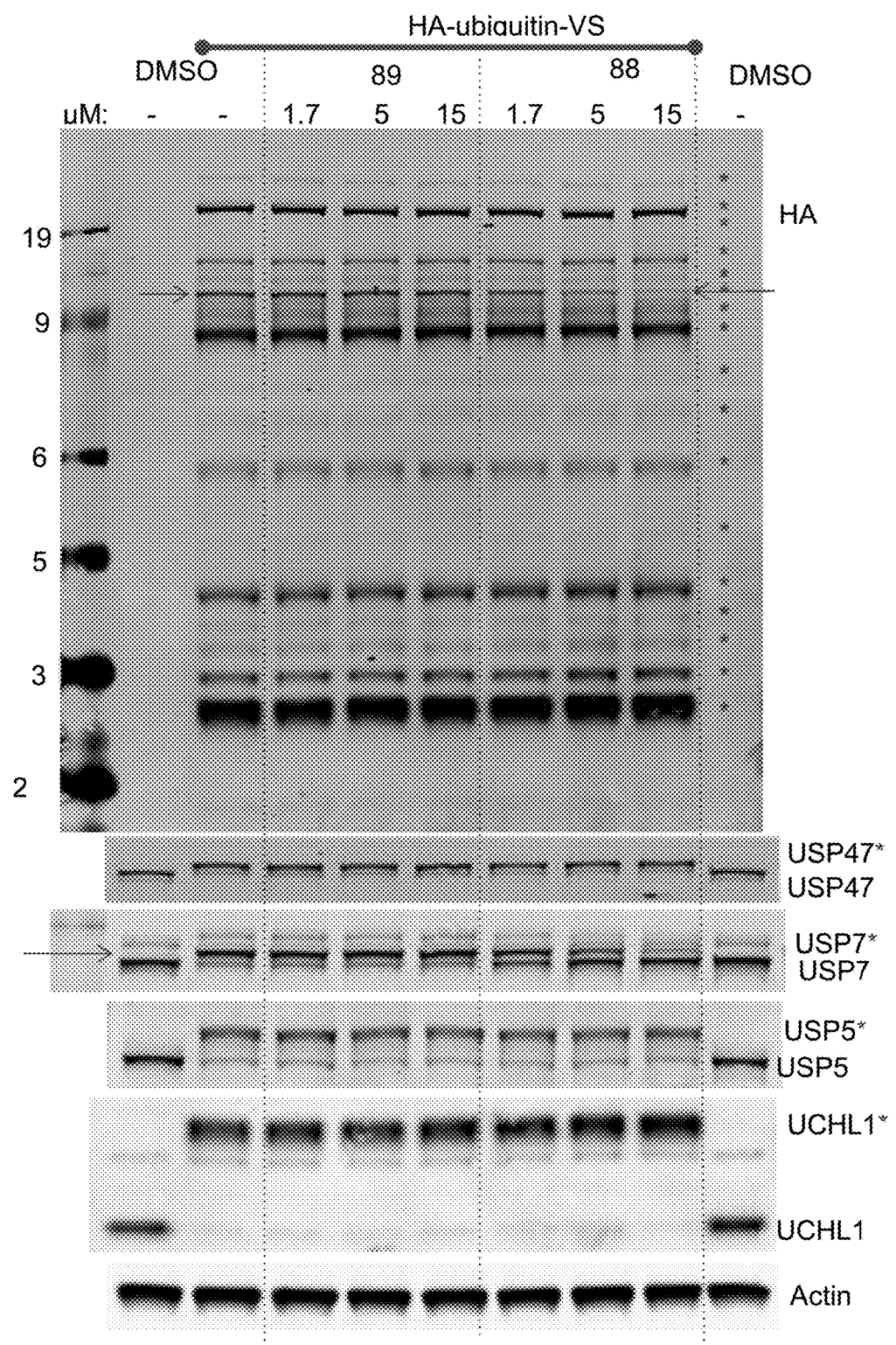
FIG. 5 shows western blot data of activity-based profiling to show that the HA-probe-conjugated band corresponding to USP7 (indicated by arrows) is decreased in lysates treated with compound 88, indicating selective DUB inhibition with 88. The asterisks designate endogenous HA-probe-conjugated DUBs.

FIG. 5 shows western blot data of activity-based profiling to show that the HA-probe-conjugated band corresponding to USP7 is decreased in lysates treated with compound 88, indicating selective DUB inhibition with 88.

Figure 6:
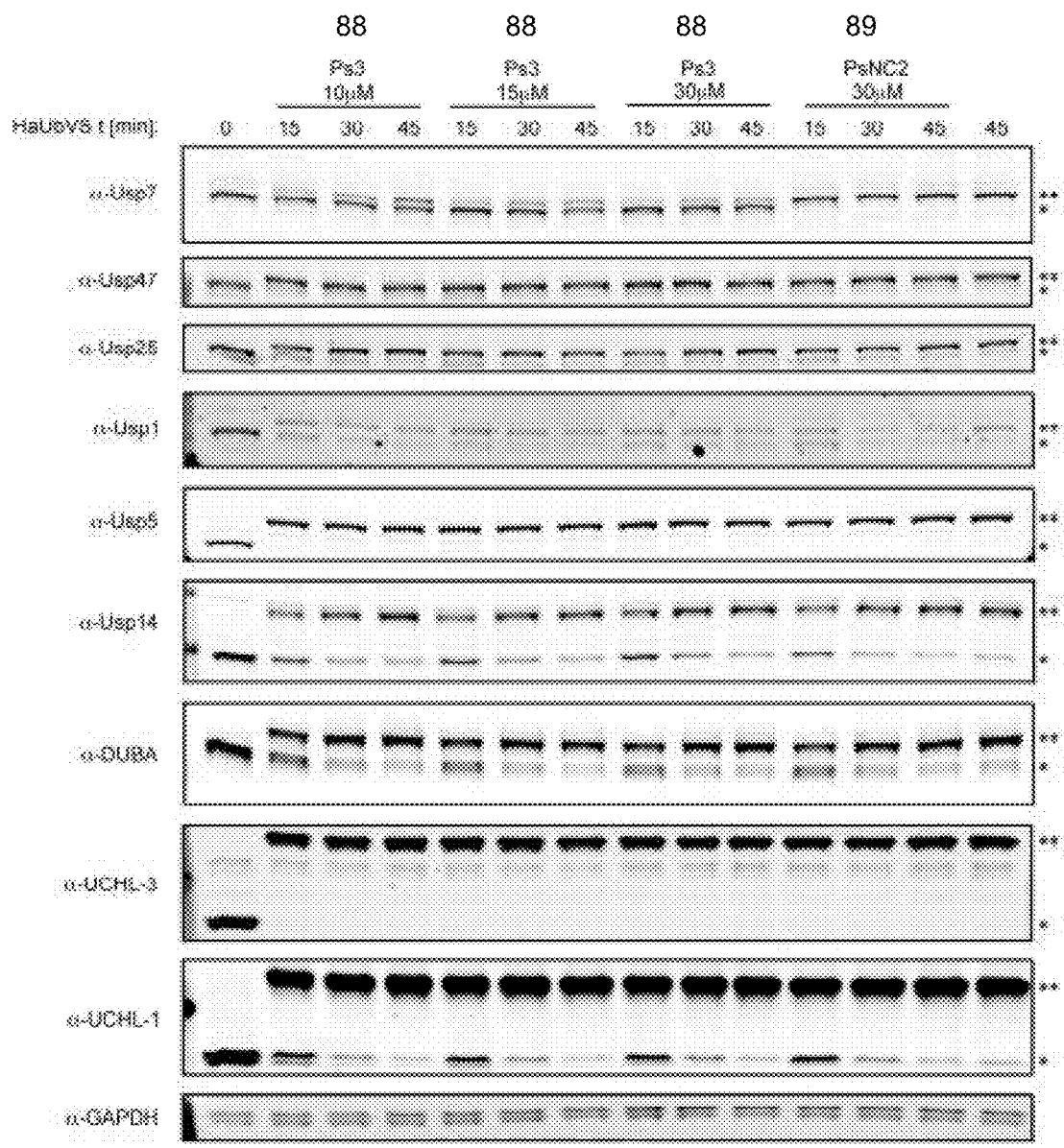
FIG. 6 shows western blot data of activity-based profiling to show that only Palm-binding compound 88, and not 89, selectively antagonizes endogenous USP7 over other DUBs evaluated by western blotting, indicating selective DUB inhibition with 88.

FIG. 6 shows western blot data of activity-based profiling to show that only Palm-binding compound 88, and not 89, selectively antagonizes endogenous USP7 over other DUBs evaluated by western blotting, indicating selective DUB inhibition with 88.

Figure 7:
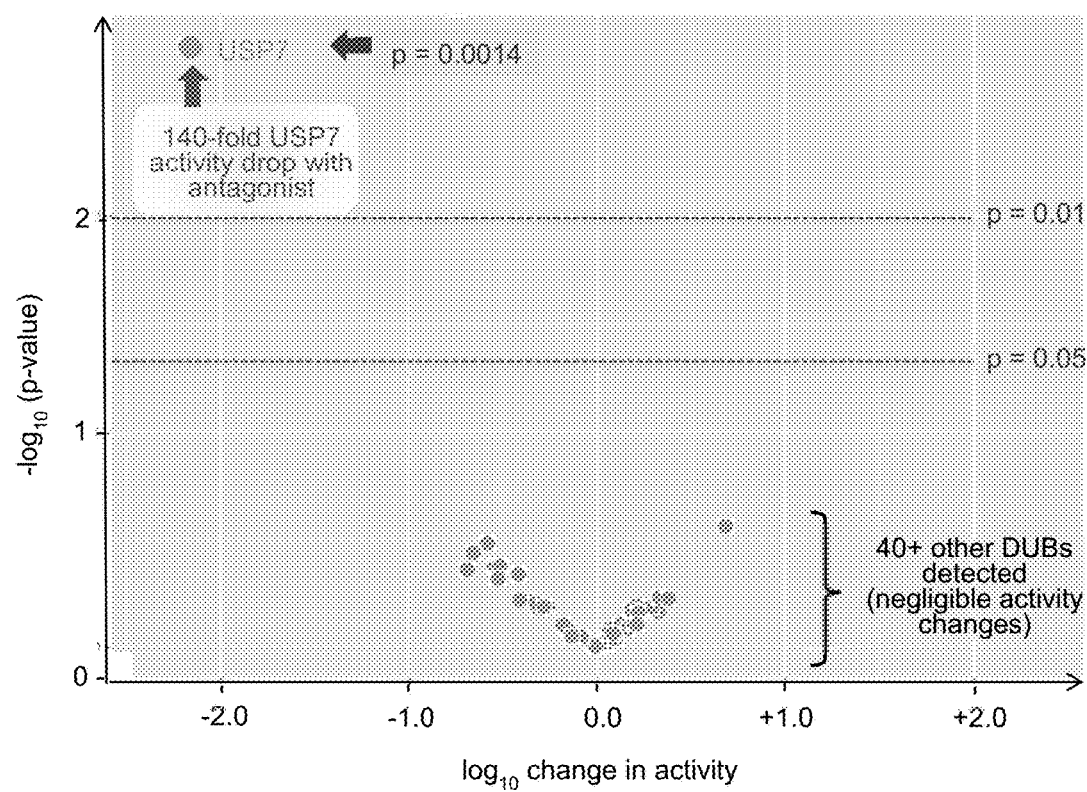
FIG. 7 shows a plot of activity-based profiling to show that active Palm-binding compound selectively antagonize endogenous USP7 over other DUBs evaluated by mass spectrometry, indicating selective DUB inhibition with active compounds.

FIG. 7 shows a plot of activity-based profiling to show that active Palm-binding compound selectively antagonize endogenous USP7 over other DUBs evaluated by mass spectrometry, indicating selective DUB inhibition with active compounds.

Figure 8A:
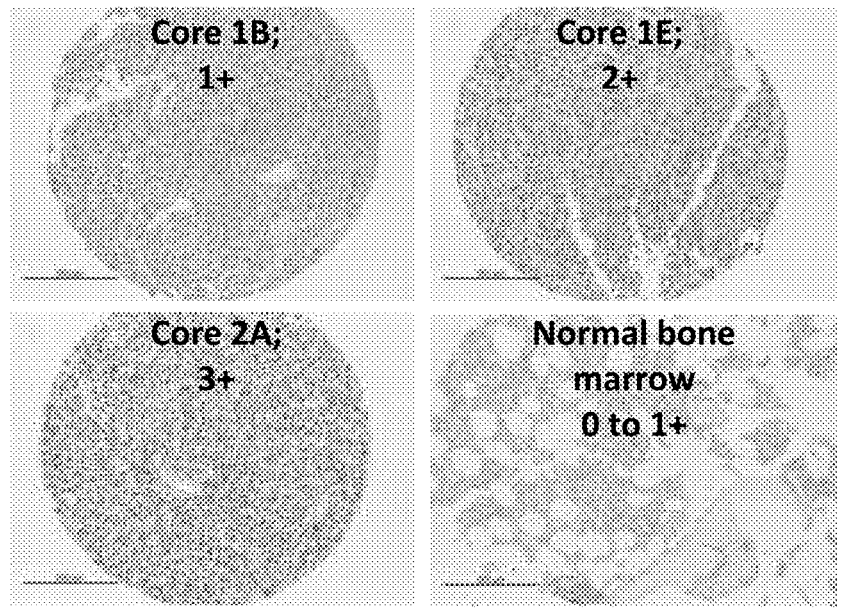
FIG. 8A shows immunohistochemical analysis of elevated USP7 expression in multiple myeloma specimens relative to normal bone marrow specimens: Core 1B; 1+, Core 1E; 2+, Core 2A; 3+, and Normal bone marrow; 0 to 1+.

FIG. 8A shows immunohistochemical analysis of elevated USP7 expression in multiple myeloma specimens relative to normal bone marrow specimens.

Figure 8B:
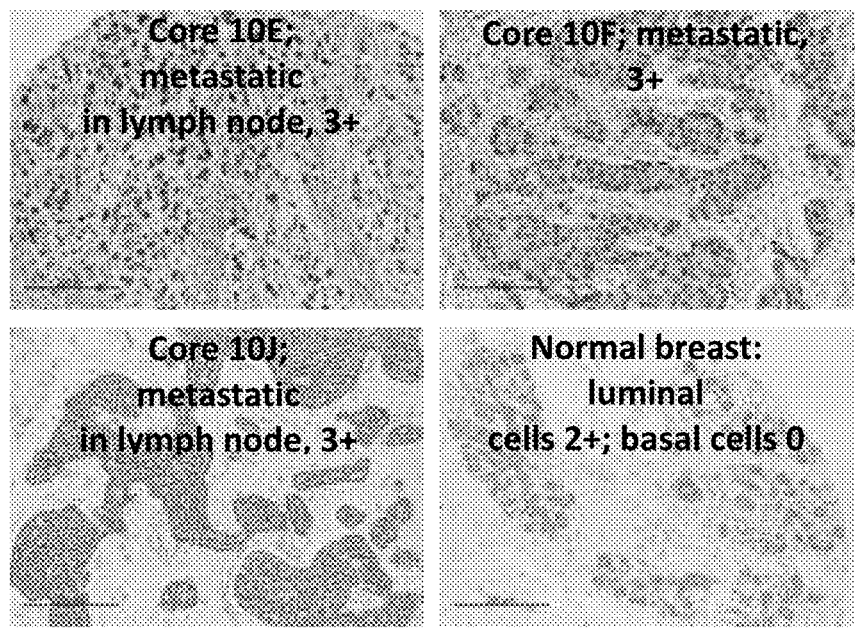
FIG. 8B shows immunohistochemical analysis of elevated USP7 expression in breast cancer specimens relative to normal breast specimens: Core 10E; metastatic in lymph node, 3+, Core 10F; metastatic, 3+, Core 10J; metastatic in lymph node, 3+, and Normal breast: luminal cells 2+; basal cells 0.

FIG. 8B shows immunohistochemical analysis of elevated USP7 expression in breast cancer specimens relative to normal breast specimens.

Figure 9:
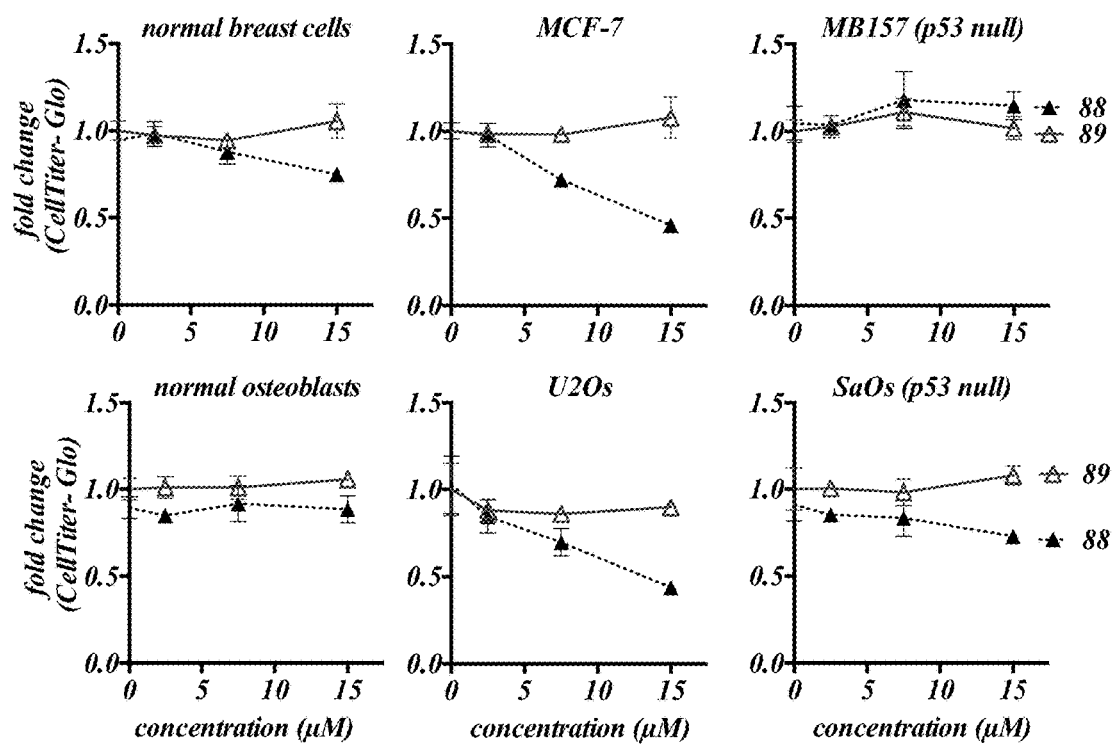
FIG. 9 shows CellTiter-Glo® (Promega Corp.) data indicating that wild-type p53-containing tumor cell lines MCF-7 and U Os have decreased viability when treated with compound 88 relative to compound 89, but matched normal osteoblast cell lines, and matched p53 null cell lines MDA-MB157 and SaOs of the same tissue origin, do not show similar decreases in cell viability, indicating a potential therapeutic index of tumor vs. normal cells and p53 dependence for decreased tumor cell viability.

FIG. 9 shows CellTiter-Glo® (Promega Corp.) data indicating that wild-type p53-containing tumor cell lines have decreased viability when treated with palm-binding compound 88 relative to compound 89, but matched normal cell lines, and matched p53 null cell lines of the same tissue origin, do not show similar decreases in cell viability, indicating a potential therapeutic index of tumor vs. normal cells and p53 dependence for decreased tumor cell viability.

Figure 10:
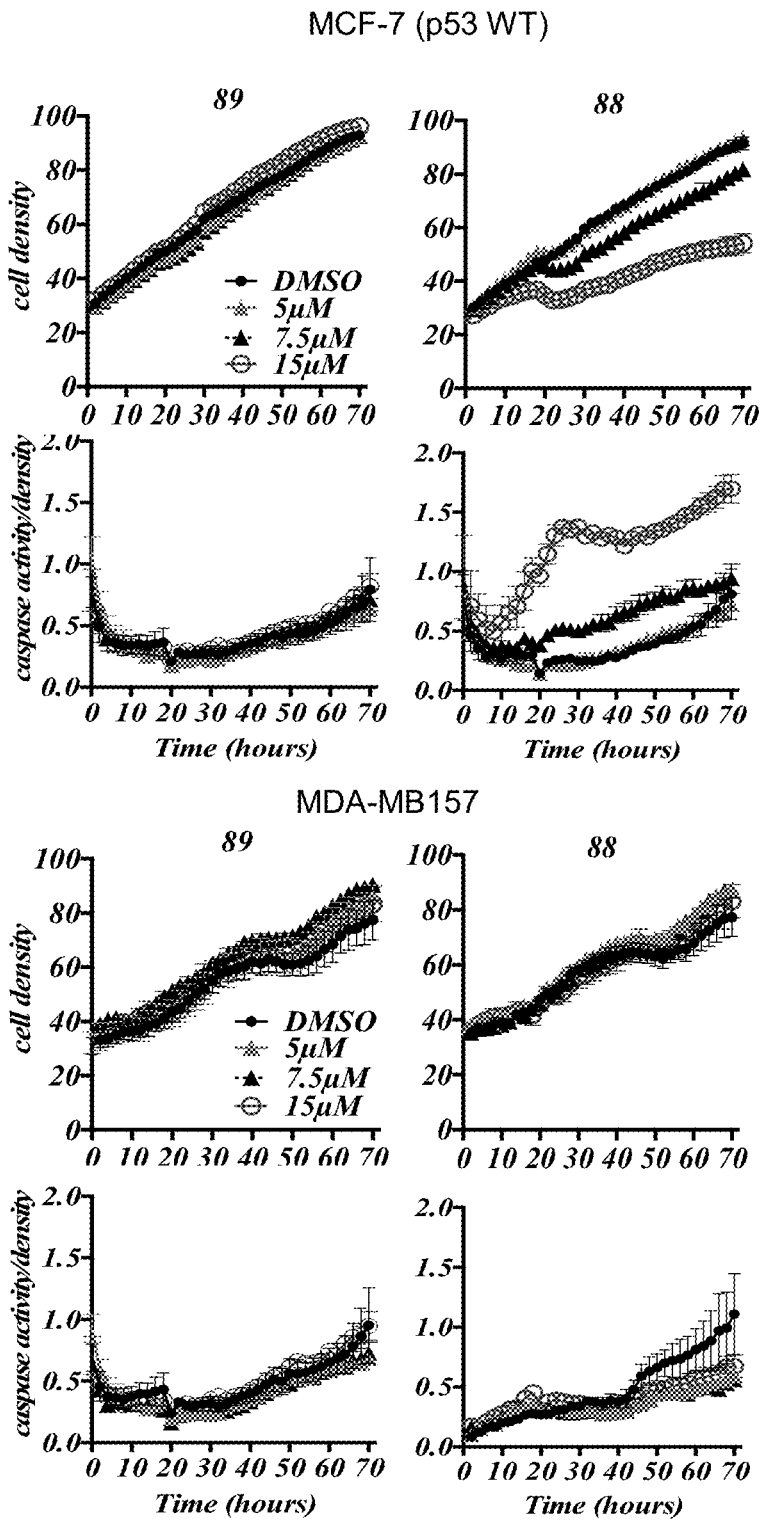
FIG. 10 shows cell proliferation and caspase activity data (Incucyte®, Essen BioScience) from Example 906 indicating that the active palm-site compound 88 compared to 89 decreases cell viability of MCF-7 p53 WT breast cancer cells compared to MDA-MB157 p53 null cells.

FIG. 10 shows cell proliferation and caspase activity data (Incucyte®), Essen BioScience) from Example 906 indicating that the active palm-site compound 88 compared to 89 decreases cell viability of MCF-7 p53 WT breast cancer cells compared to MDA-MB 157 p53 null cells.

Figure 11:
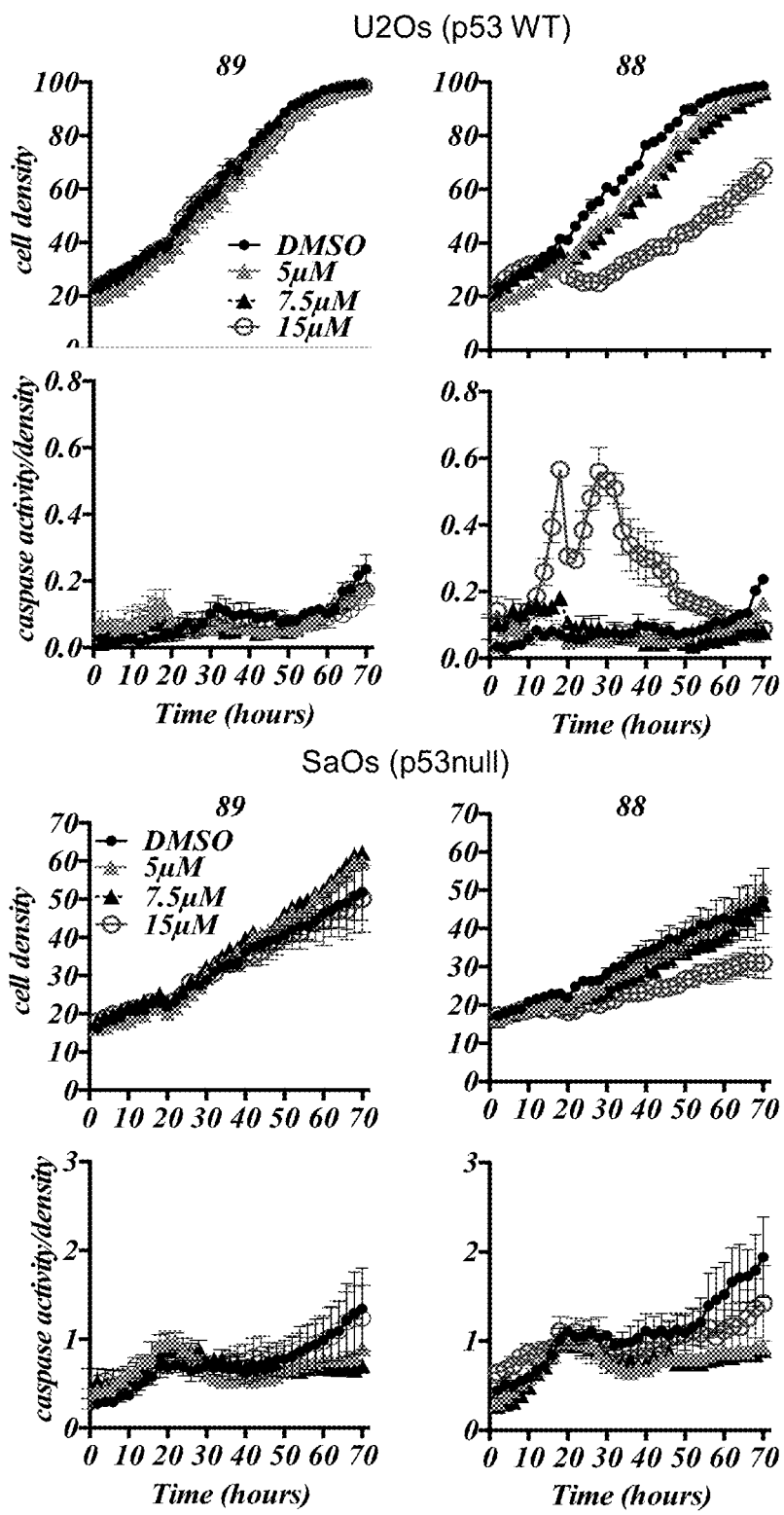
FIG. 11 shows cell proliferation and caspase activity data (Incucyte®, Essen BioScience) from Example 906 indicating that the active palm-site compound 88 compared to 89 decreases cell viability of U2Os p53 WT osteosarcoma cells compared to SaOs p53 null cells.

FIG. 11 shows cell proliferation and caspase activity data (Incucyte®, Essen BioScience) from Example 906 indicating that the active palm-site compound 88 compared to 89 decreases cell viability of U2Os p53 WT osteosarcoma cells compared to SaOs p53 null cells.

Figure 12A:
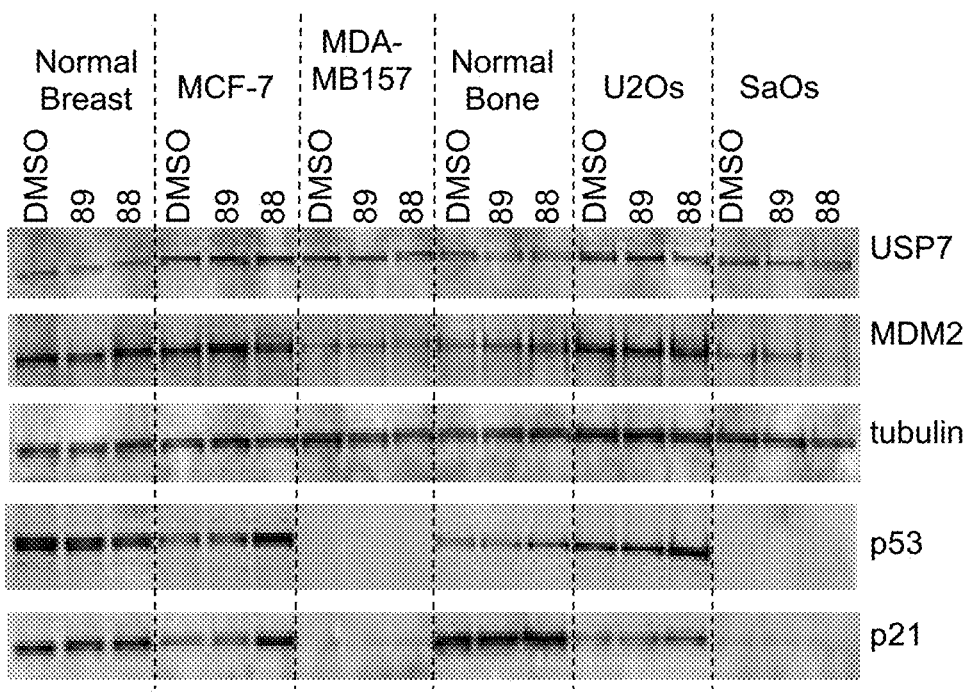
FIG. 12A shows western blot data indicating that the active compound 88 compared to 89 increases p53 and p21 levels in p53 wild-type breast cancer and osteosarcoma cells but not normal cells. Cells were treated with 15 µM compounds 88 and 89 for <24 h in low serum.

FIG. 12A shows western blot data indicating that the active compound 88 compared to 89 increases p53 and p21 levels in p53 wild-type breast cancer and osteosarcoma cells but not normal cells.

Figure 12B:
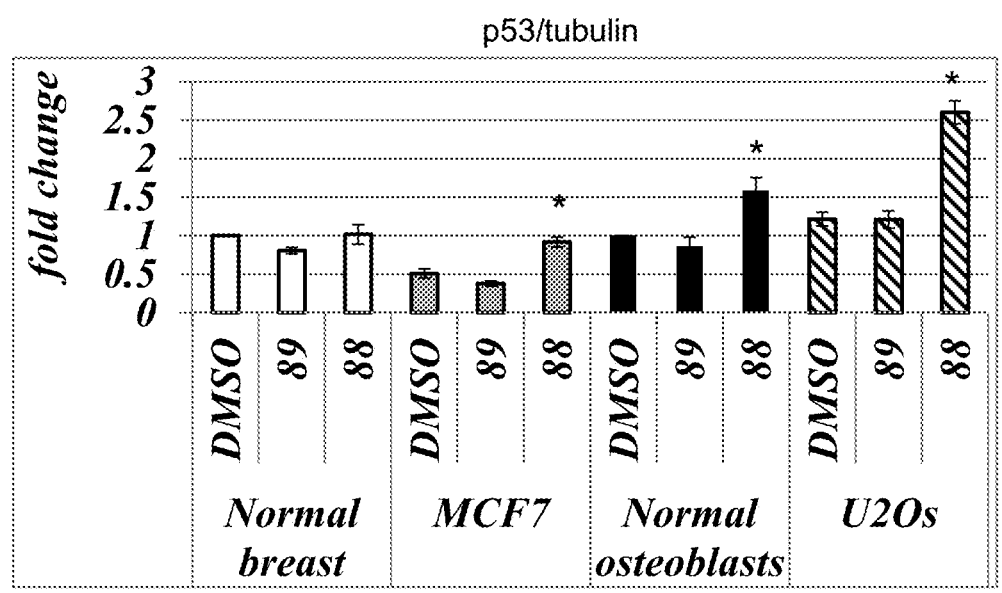
FIG. 12B shows a plot of p53/tubulin change in p53 wild-type breast cancer and osteosarcoma cells but not normal cells treated with compounds 88 and 89.

FIG. 12B shows a plot of p53/tubulin change in p53 wild-type breast cancer and osteosarcoma cells but not normal cells treated with compounds 88 and 89.

Figure 12C:
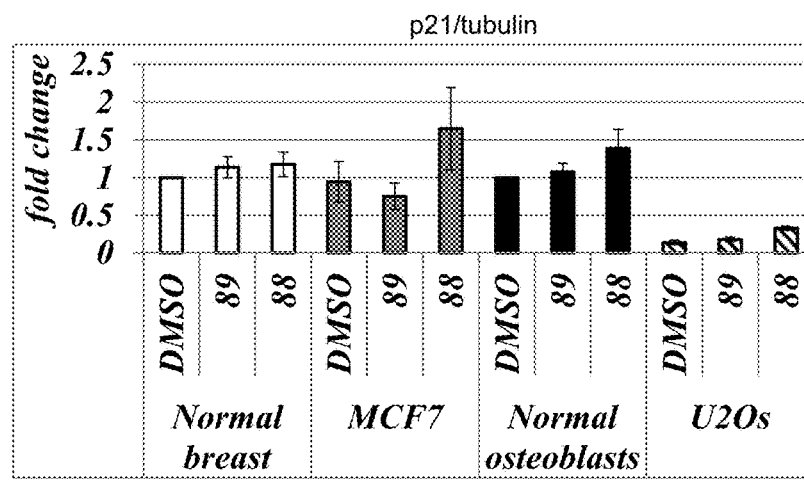
FIG. 12C shows a plot of p21/tubulin change in p53 wild-type breast cancer and osteosarcoma cells but not normal cells treated with compounds 88 and 89.

FIG. 12C shows a plot of p21/tubulin change in p53 wild-type breast cancer and osteosarcoma cells but not normal cells treated with compounds 88 and 89.

Figure 12D:
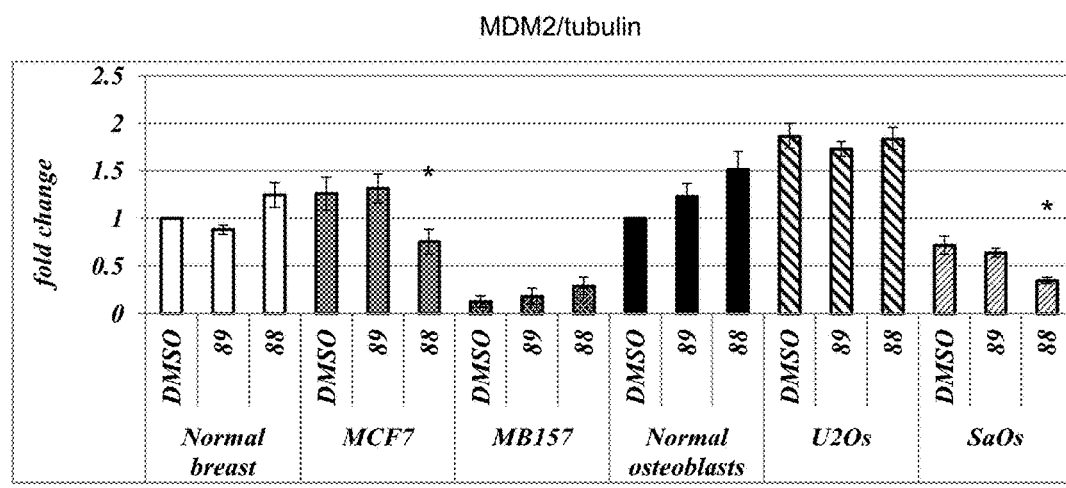
FIG. 12D shows a plot of MDM2/tubulin change in p53 wild-type breast cancer MCF7 and MDA-MB157 and osteosarcoma cells U2Os and SaOs but not normal cells treated with compounds 88 and 89.

FIG. 12D shows a plot of MDM2/tubulin change in p53 wild-type breast cancer and osteosarcoma cells but not normal cells treated with compounds 88 and 89.

Figure 13A:
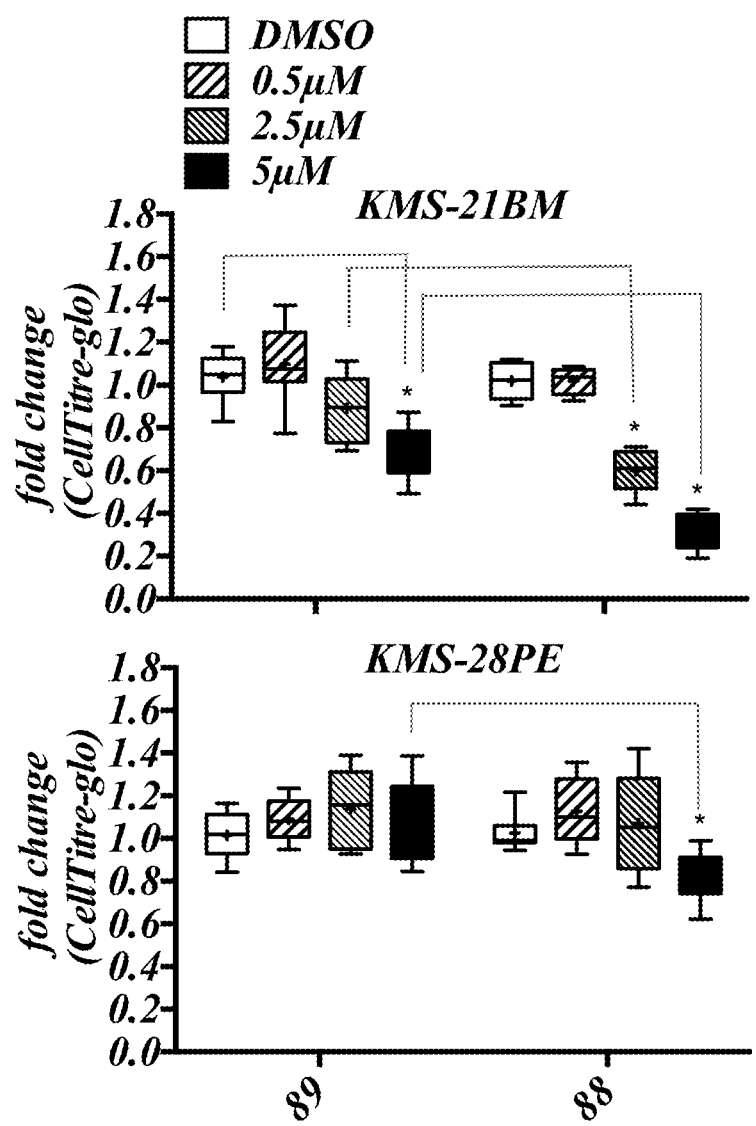
FIG. 13A shows cell viability data indicating that the active compound 88 compared to 89 decreases Cell Titer Glo signal, indicating a decrease in cell viability in KMS-21BM and KMS-28PE multiple myeloma cells.

FIG. 13A shows cell viability data indicating that the active compound 88 compared to 89 decreases Cell Titer Glo signal, indicating a decrease in cell viability in KMS-21BM and KMS-28PE multiple myeloma cells.

FIG. 13B shows western blot data indicating that the active compound 88 compared to 89 increases p53 and p21 levels in KMS-21BM and KMS-28PE multiple myeloma cells.

FIG. 13C shows a plot of p53/tubulin change in KMS-21BM and KMS-28PE multiple myeloma cells treated with compounds 88 and 89.

FIG. 13D shows a plot of p21/tubulin change in KMS-21BM and KMS-28PE multiple myeloma cells treated with compounds 88 and 89.

Figure 14A:
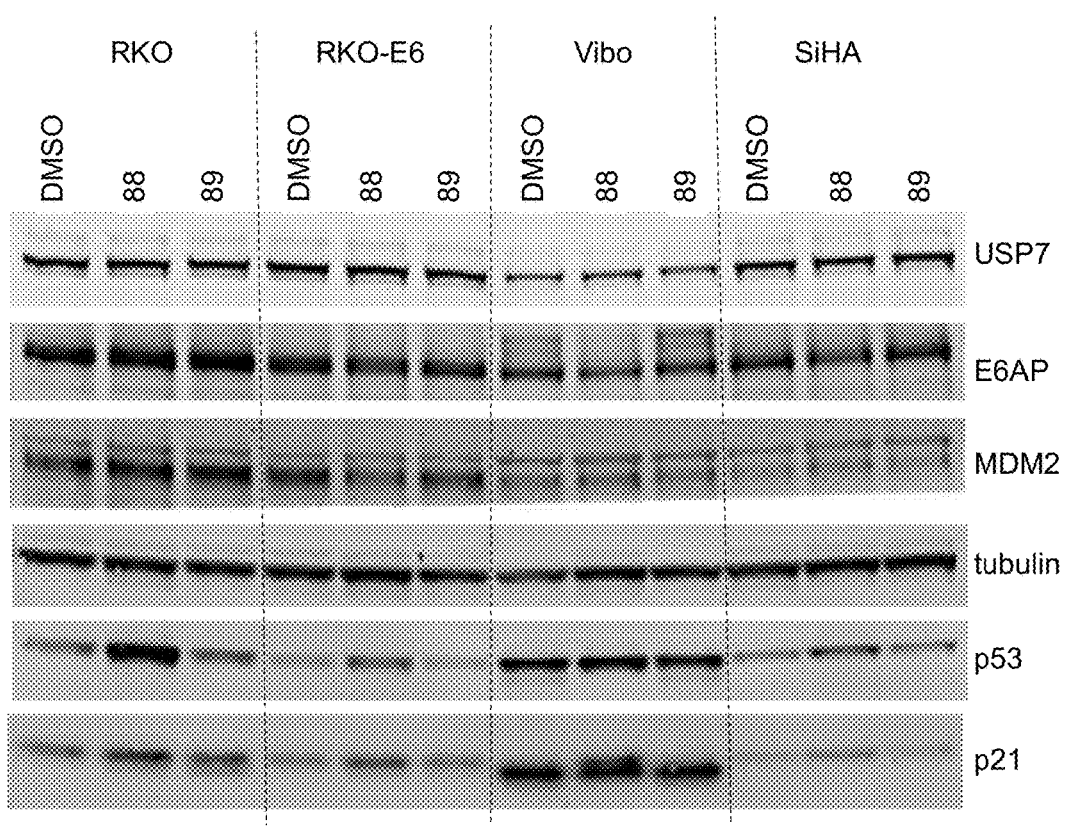
FIG. 14A shows western blot data indicating that palm-binding compounds 88 and 89 stabilize p53, p21, and destabilize MDM2 and E6AP in colon cancer cell lines RKO and RKO-E6, and cervical cancer cell lines Vibo and SiHA.

FIG. 14A shows western blot data indicating that palm-binding compounds 88 and 89 stabilize p53, p21, and destabilize MDM2 and E6AP in cervical cancer cell lines RKO, RKO-E6, Vibo, and SiHA.

Figure 14B:
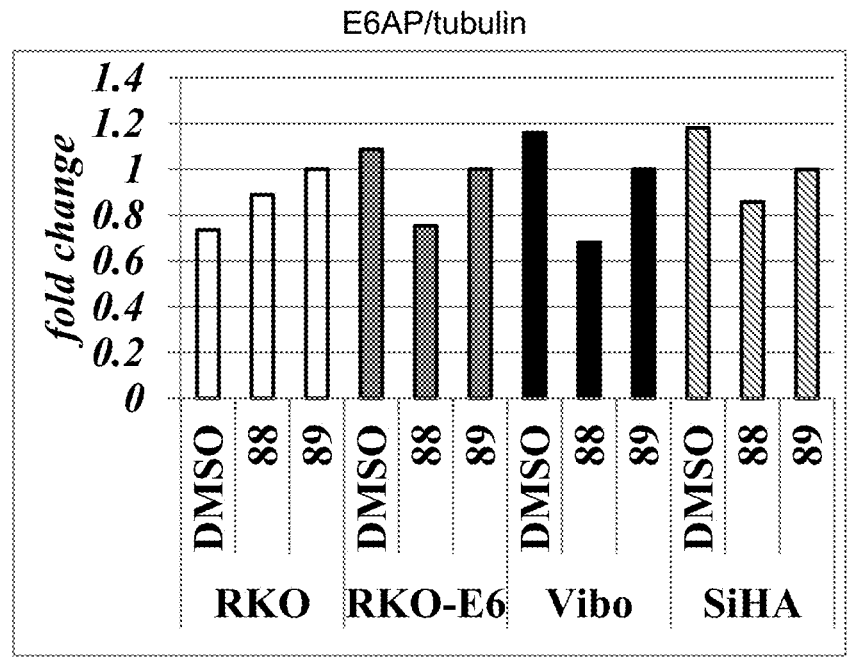
FIG. 14B shows a plot of E6AP/tubulin change in colon cancer cell lines RKO RKO-E6, and cervical cancer cell lines Vibo and SiHA treated with compounds 88 and 89.

FIG. 14B shows a plot of E6AP/tubulin change in cervical cancer cell lines RKO, RKO-E6, Vibo, and SiHA treated with compounds 88 and 89.

Figure 14C:
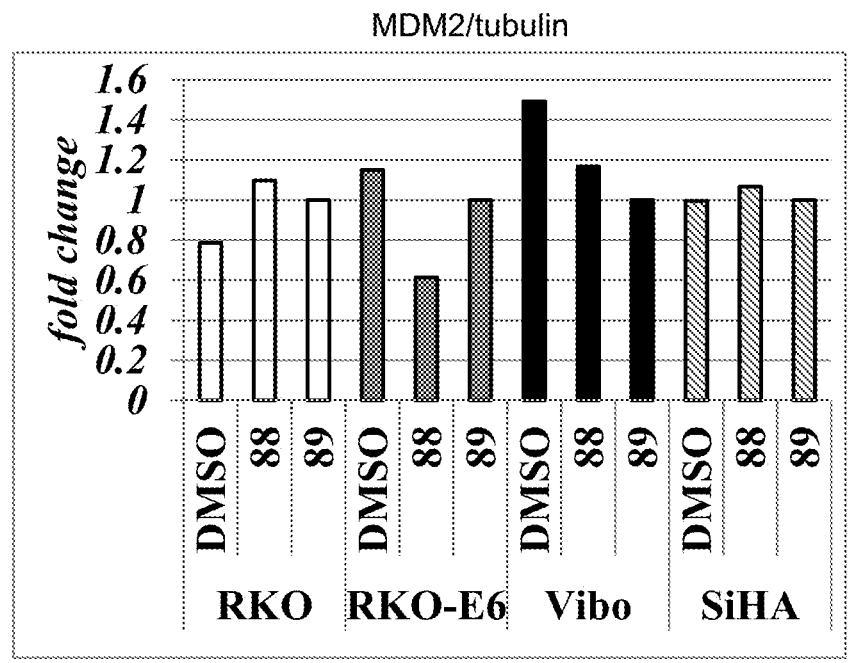
FIG. 14C shows a plot of MDM2/tubulin change in colon cancer cell lines RKO and RKO-E6, and cervical cancer cell lines Vibo and SiHA treated with compounds 88 and 89.

FIG. 14C shows a plot of MDM2/tubulin change in cervical cancer cell lines RKO, RKO-E6, Vibo, and SiHA treated with compounds 88 and 89.

Figure 15:
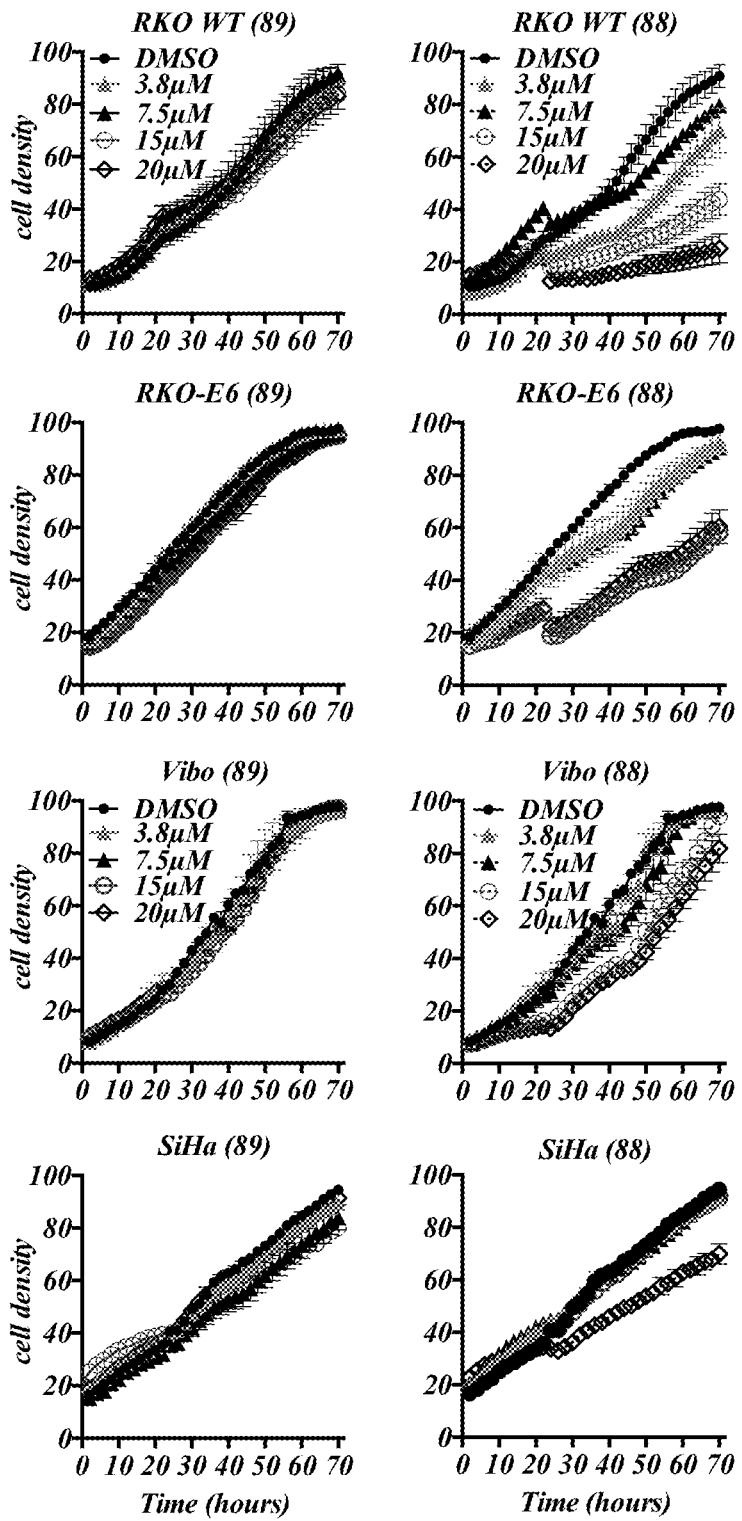
FIG. 15 shows cell proliferation (Incucyte®, Essen BioScience) data indicating that active compound 88 but not compound 89 decreases cell viability of colon cancer cell lines RKO RKO-E6, and cervical cancer cell lines Vibo and SiHA.

FIG. 15 shows cell proliferation (Incucyte®, Essen Bio-Science) data indicating that active compound 88 but not compound 89 decreases cell viability of cervical cancer cell lines RKO, RKO-E6, Vibo, and SiHA.

Figure 16:
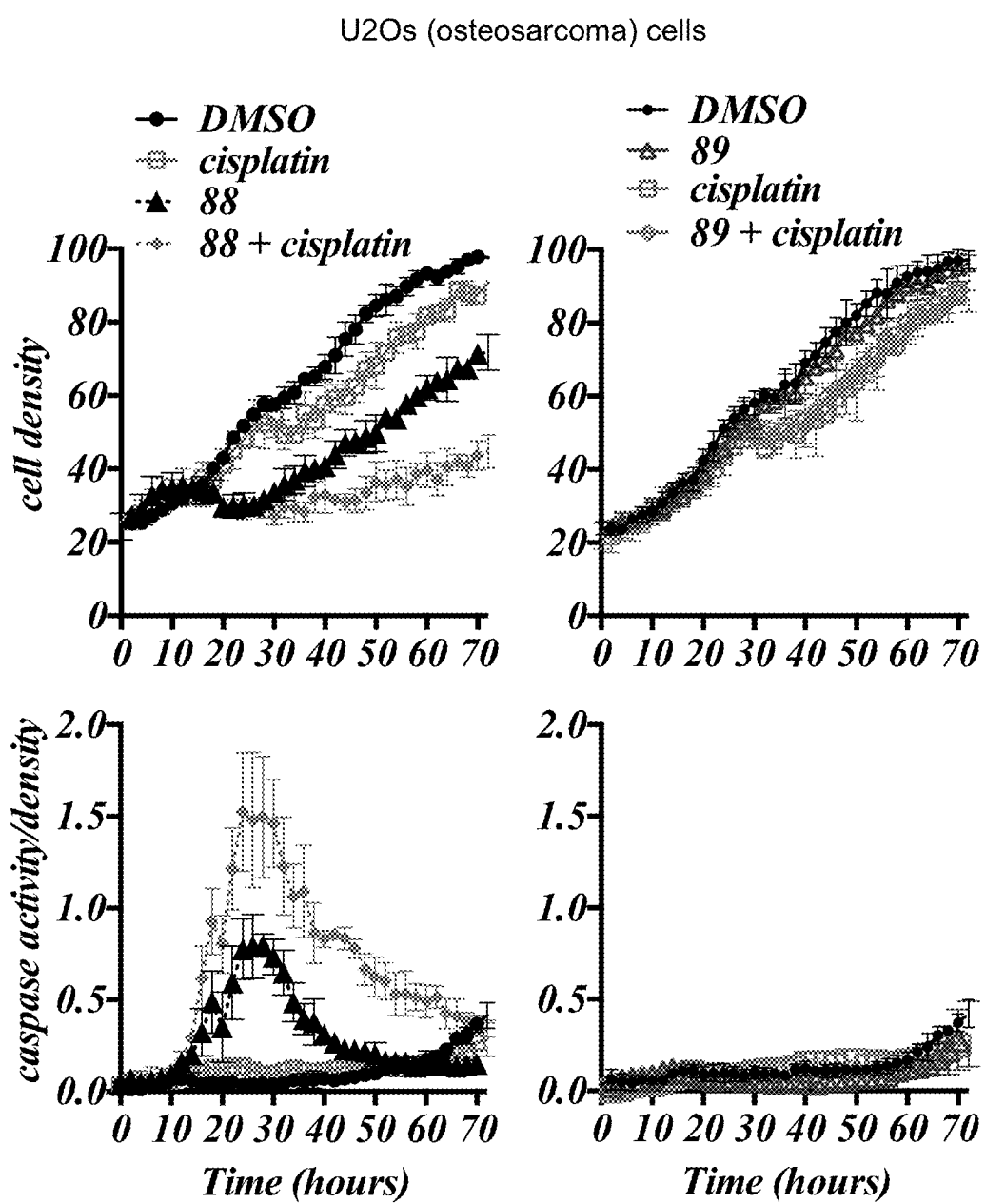
FIG. 16 shows cell proliferation (Incucyte®, Essen BioScience) and caspase activity data with U2Os (osteosarcoma) cells using either cisplatin (1 µM), the compounds 88 and 89 (15 µM), or the combinations of 88+ cisplatin, and 89+ cisplatin. The combination treatment of 88+ cisplatin most potently decreases cell proliferation and enhances caspase activity.

FIG. 16 shows cell proliferation (Incucyte®, Essen Bio-Science) and caspase activity data with U2Os (osteosarcoma) cells using either cisplatin (1 µM), compounds 88 and 89 (15 µM), or the combinations of 88+ cisplatin, and 89+ cisplatin. The combination treatment of 88+ cisplatin most potently decreases cell proliferation and enhances caspase activity.

Figure 17:
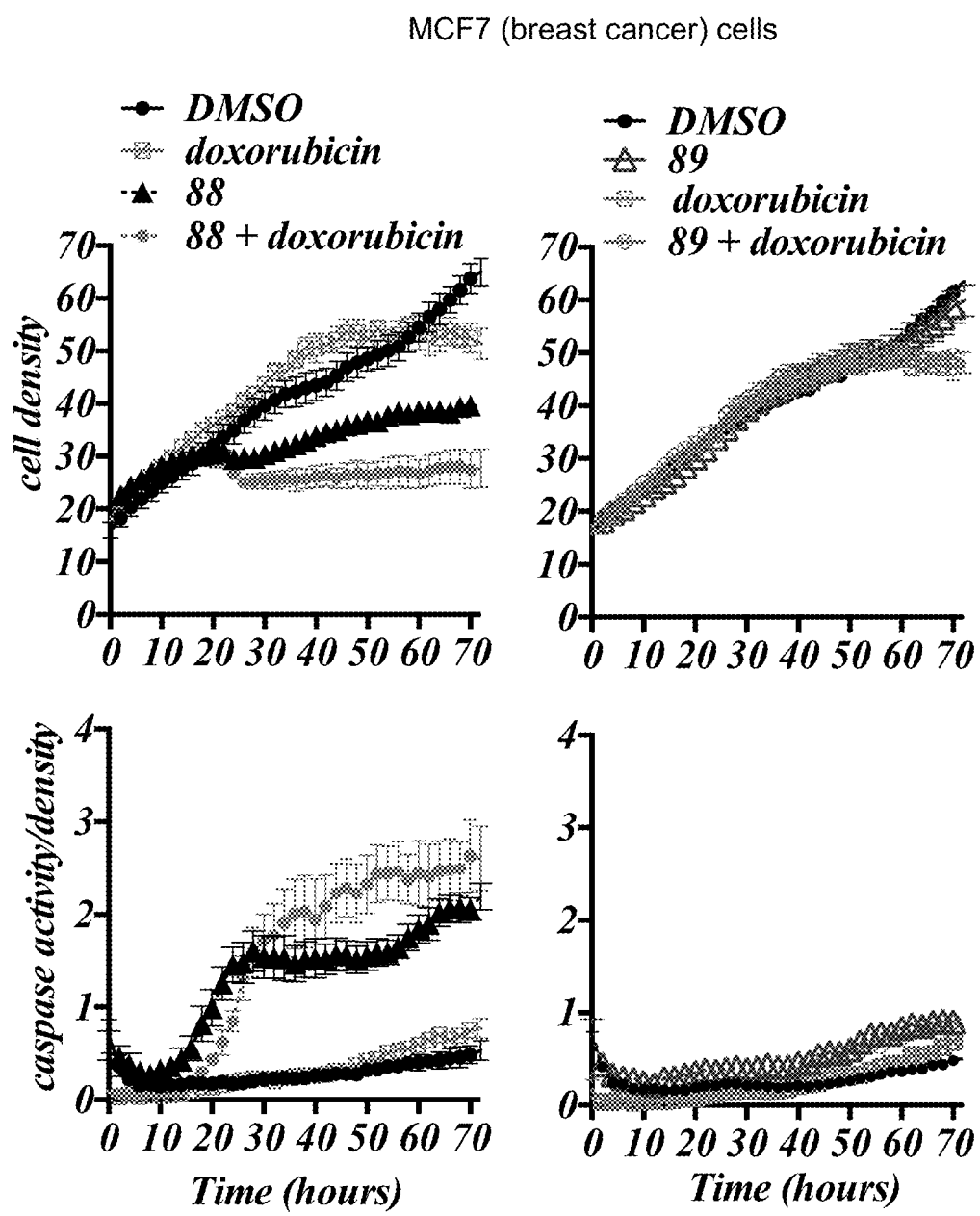
FIG. 17 shows cell proliferation (Incucyte®, Essen BioScience) and caspase activity data with MCF7 (breast cancer) cells using either doxorubicin (0.1 µM), the compounds 88 and 89 (15 µM), or the combinations of 88+ doxorubicin, and 89+ doxorubicin. The combination treatment of 88+ doxorubicin most potently decreases cell proliferation and enhances caspase activity.

FIG. 17 shows cell proliferation (Incucyte®, Essen Bio-Science) and caspase activity data with MCF7 (breast cancer) cells using either doxorubicin (0.1 µM), compounds 88 and 89 (15 µM), or the combinations of 88+ doxorubicin, and 89+ doxorubicin. The combination treatment of 88+ doxorubicin most potently decreases cell proliferation and enhances caspase activity.

Exemplary Formula I compounds in Table 1 were made, characterized, and tested for binding to USP7 according to the methods of this invention, and have the following structures, corresponding names (ChemBioDraw, Version 12.0.2, CambridgeSoft Corp., Cambridge Mass.), and biological activity. Where more than one name is associated with a Formula I compound or intermediate, the chemical structure shall define the compound.

TABLE 1

| No. | Structure | IUPAC_Name | USP7 Ub-Rho preInc (IC50) μmol | USP7 Ub-Rho110 Fluor (IC50) μmol |
|---|---|---|---|---|
| 1 | 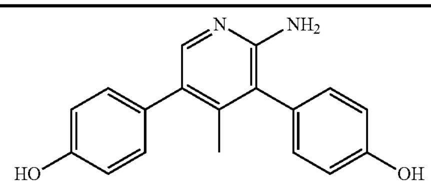 | 4-[6-amino-5-(4-hydroxyphenyl)-4-methyl-3-pyridyl]phenol | | 7.7 |
| 2 | 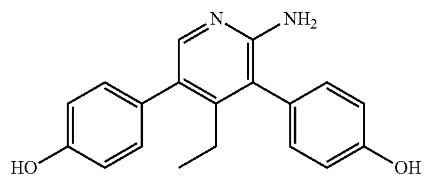 [SMILES: CCc1c(-c2ccc(O)cc2)cnc(N)c1-c1ccc(O)cc1] | 4-[6-amino-4-ethyl-5-(4-hydroxyphenyl)-3-pyridyl]phenol | 4.6 | 3 |
| 3 | 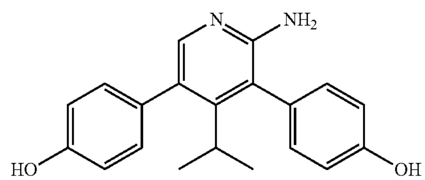 [SMILES: CC(C)c1c(-c2ccc(O)cc2)cnc(N)c1-c1ccc(O)cc1] | 4-[6-amino-5-(4-hydroxyphenyl)-4-isopropyl-3-pyridyl]phenol | | 197 |
| 4 | 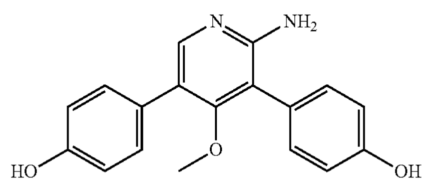 [SMILES: COc1c(-c2ccc(O)cc2)cnc(N)c1-c1ccc(O)cc1] | 4-[6-amino-5-(4-hydroxyphenyl)-4-methoxy-3-pyridyl]phenol | | 29.1 |
| 5 | 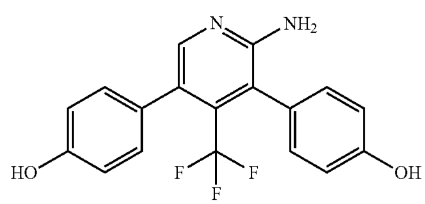 [SMILES: Nc1ncc(-c2ccc(O)cc2)c(C(F)(F)F)c1-c1ccc(O)cc1] | 4-[6-amino-5-(4-hydroxyphenyl)-4-(trifluoromethyl)-3-pyridyl]phenol | 7.1 | 6 |
| 6 | 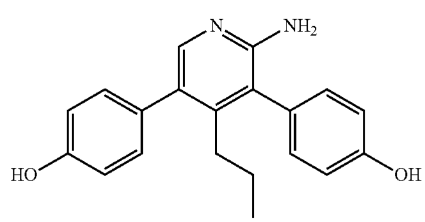 [SMILES: CCCc1c(-c2ccc(O)cc2)cnc(N)c1-c1ccc(O)cc1] | 4-[6-amino-5-(4-hydroxyphenyl)-4-propyl-3-pyridyl]phenol | | 35.2 |
| 7 | 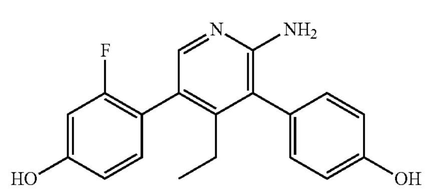 [SMILES: CCc1c(-c2ccc(O)cc2F)cnc(N)c1-c1ccc(O)cc1] | 4-[6-amino-4-ethyl-5-(4-hydroxyphenyl)-3-pyridyl]-3-fluoro-phenol | | 4.5 |
| 8 | 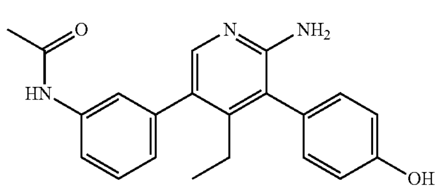 [SMILES: CCc1c(-c2cccc(NC(C)=O)c2)cnc(N)c1-c1ccc(O)cc1] | N-[3-[6-amino-4-ethyl-5-(4-hydroxyphenyl)-3-pyridyl]phenyl]acetamide | | 45 |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 9 | 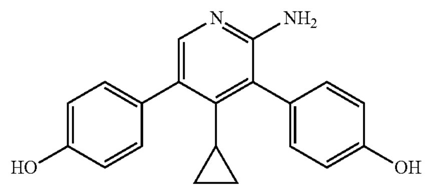 [SMILES: Nc1ncc(-c2ccc(O)cc2)c(C2CC2)c1-c1ccc(O)cc1] | 4-[6-amino-4-cyclopropyl-5-(4-hydroxyphenyl)-3-pyridyl]phenol | | 56.6 |
| 10 | 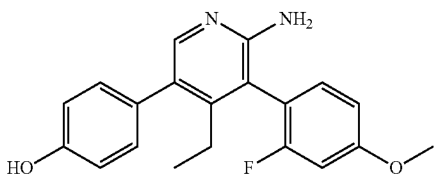 [SMILES: CCc1c(-c2ccc(O)cc2)cnc(N)c1-c1ccc(OC)cc1F] | 4-[6-amino-4-ethyl-5-(2-fluoro-4-methoxyphenyl)-3-pyridyl]phenol | 13 | 7.5 |
| 11 | 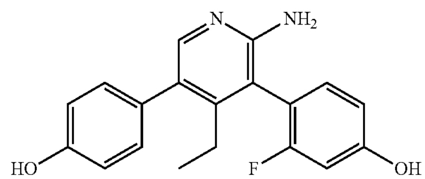 [SMILES: CCc1c(-c2ccc(O)cc2)cnc(N)c1-c1ccc(O)cc1F] | 4-[2-amino-4-ethyl-5-(4-hydroxyphenyl)-3-pyridyl]-3-fluoro-phenol | | >20 |
| 12 | 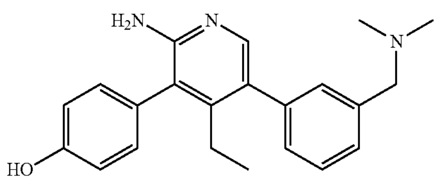 [SMILES: CCc1c(-c2cccc(CN(C)C)c2)cnc(N)c1-c1ccc(O)cc1] | 4-[2-amino-5-[3-[(dimethylamino)methyl]phenyl]-4-ethyl-3-pyridyl]phenol | | 23.9 |
| 13 | 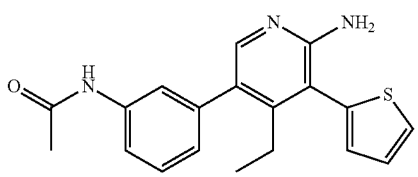 [SMILES: CCc1c(-c2cccc(NC(C)=O)c2)cnc(N)c1-c1cccs1] | N-[3-[6-amino-4-ethyl-5-(2-thienyl)-3-pyridyl]phenyl]acetamide | | >63.3 |
| 14 | 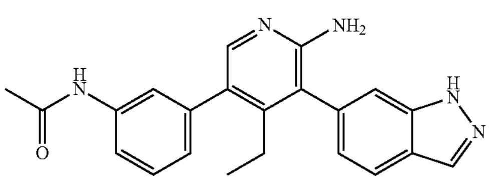 [SMILES: CCc1c(-c2cccc(NC(C)=O)c2)cnc(N)c1-c1ccc2cn[nH]c2c1] | N-[3-[6-amino-4-ethyl-5-(1H-indazol-6-yl)-3-pyridyl]phenyl]acetamide | 136 | |
| 15 | 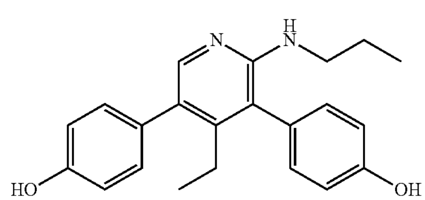 [SMILES: CCCNc1ncc(-c2ccc(O)cc2)c(CC)c1-c1ccc(O)cc1] | 4-[4-ethyl-5-(4-hydroxyphenyl)-6-(propylamino)-3-pyridyl]phenol | 10.1 | |
| 16 | 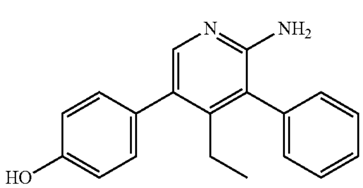 [SMILES: CCc1c(-c2ccc(O)cc2)cnc(N)c1-c1ccccc1] | 4-(6-amino-4-ethyl-5-phenyl-3-pyridyl)phenol | 60.7 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 17 | 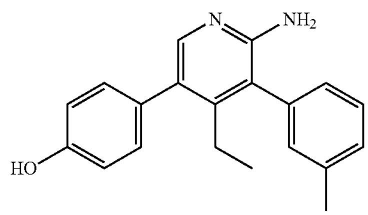 [SMILES: CCc1c(-c2ccc(O)cc2)cnc(N)c1-c1cccc(C)c1] | 4-[6-amino-4-ethyl-5-(m-tolyl)-3-pyridyl]phenol | >63.3 | |
| 18 | 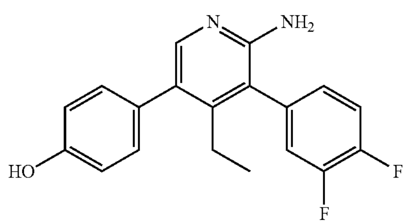 [SMILES: CCc1c(-c2ccc(O)cc2)cnc(N)c1-c1ccc(F)c(F)c1] | 4-[6-amino-5-(3,4-difluorophenyl)-4-ethyl-3-pyridyl]phenol | >20 | |
| 19 | 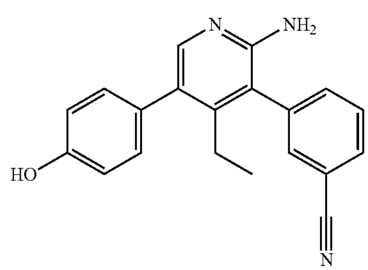 [SMILES: CCc1c(-c2ccc(O)cc2)cnc(N)c1-c1cccc(C#N)c1] | 3-[2-amino-4-ethyl-5-(4-hydroxyphenyl)-3-pyridyl]benzonitrile | 9.9 | |
| 20 | 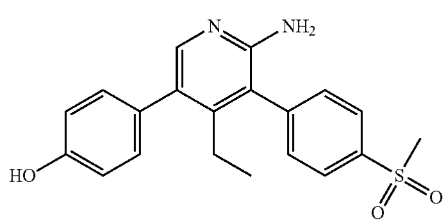 [SMILES: CCc1c(-c2ccc(O)cc2)cnc(N)c1-c1ccc(S(C)(=O)=O)cc1] | 4-[6-amino-4-ethyl-5-(4-methylsulfonylphenyl)-3-pyridyl]phenol | >63.3 | |
| 21 | 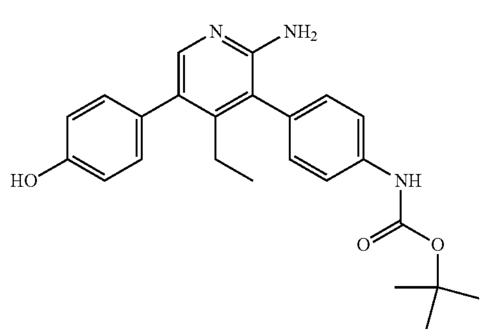 [SMILES: CCc1c(-c2ccc(O)cc2)cnc(N)c1-c1ccc(NC(=O)OC(C)(C)C)cc1] | tert-butyl N-[4-[2-amino-4-ethyl-5-(4-hydroxyphenyl)-3-pyridyl]phenyl]carbamate | >20 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 22 | 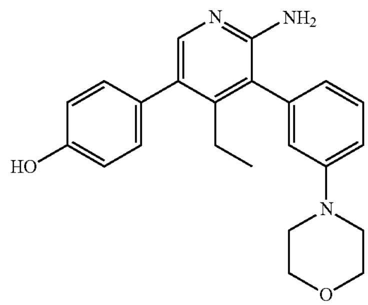 [SMILES: CCc1c(-c2ccc(O)cc2)cnc(N)c1-c1cccc(N2CCOCC2)c1] | 4-[6-amino-4-ethyl-5-(3-morpholinophenyl)-3-pyridyl]phenol | >63.3 | |
| 23 | 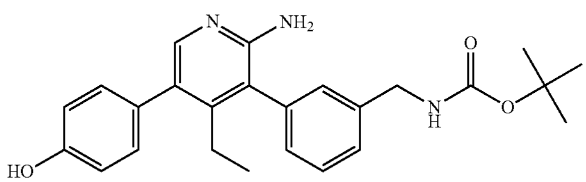 [SMILES: CCc1c(-c2ccc(O)cc2)cnc(N)c1-c1cccc(CNC(=O)OC(C)(C)C)c1] | tert-butyl N-[[3-[2-amino-4-ethyl-5-(4-hydroxyphenyl)-3-pyridyl]phenyl]methyl] carbamate | >6.3 | |
| 24 | 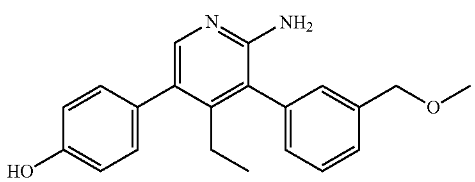 [SMILES: CCc1c(-c2ccc(O)cc2)cnc(N)c1-c1cccc(COC)c1] | 4-[6-amino-4-ethyl-5-[3-(methoxymethyl)phenyl]-3-pyridyl]phenol | >63.3 | |
| 25 | 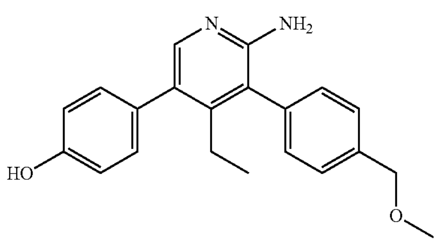 [SMILES: CCc1c(-c2ccc(O)cc2)cnc(N)c1-c1ccc(COC)cc1] | 4-[6-amino-4-ethyl-5-[4-(methoxymethyl)phenyl]-3-pyridyl]phenol | 63.3++ | |
| 26 | 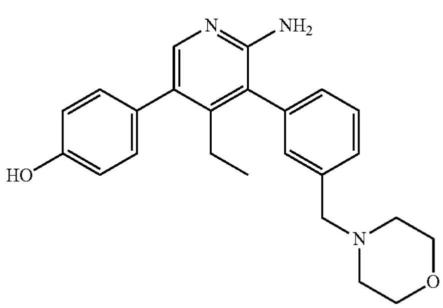 [SMILES: CCc1c(-c2ccc(O)cc2)cnc(N)c1-c1cccc(CN2CCOCC2)c1] | 4-[6-amino-4-ethyl-5-[3-(morpholinomethyl)phenyl]-3-pyridyl]phenol | 145 | |
| 27 | 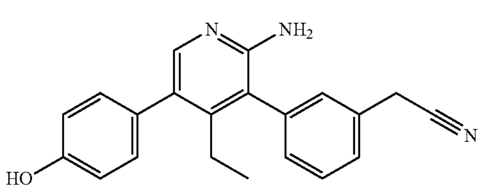 [SMILES: CCc1c(-c2ccc(O)cc2)cnc(N)c1-c1cccc(CC#N)c1] | 2-[3-[2-amino-4-ethyl-5-(4-hydroxyphenyl)-3-pyridyl]phenyl]acetonitrile | 48.7 | |

TABLE 1-continued

| No. | Structure | IUPAC_Name | USP7 Ub-Rho preInc (IC50) µmol | USP7 Ub-Rho110 Fluor (IC50) µmol |
|---|---|---|---|---|
| 28 | 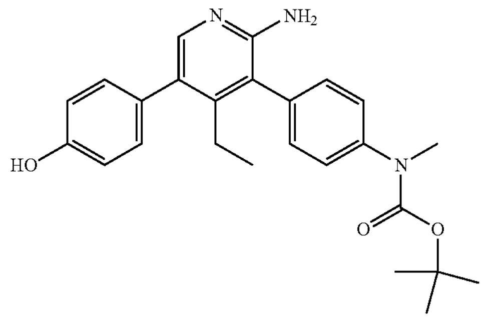 [SMILES: CCc1c(-c2ccc(O)cc2)cnc(N)c1-c1ccc(N(C)C(=O)OC(C)(C)C)cc1] | tert-butyl N-[4-[2-amino-4-ethyl-5-(4-hydroxyphenyl)-3-pyridyl]phenyl]-N-methyl-carbamate | >20 | |
| 29 | 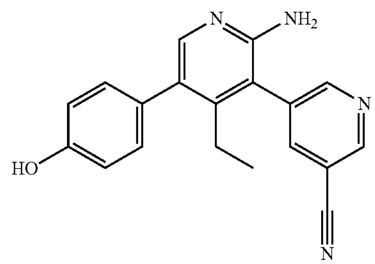 [SMILES: CCc1c(-c2ccc(O)cc2)cnc(N)c1-c1cncc(C#N)c1] | 5-[2-amino-4-ethyl-5-(4-hydroxyphenyl)-3-pyridyl]pyridine-3-carbonitrile | 18.6 | |
| 30 | 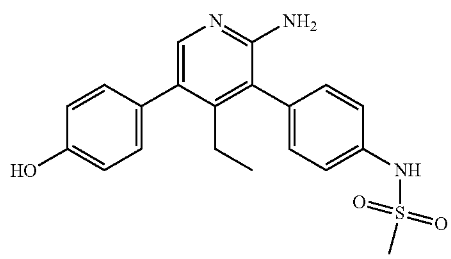 [SMILES: CCc1c(-c2ccc(O)cc2)cnc(N)c1-c1ccc(NS(C)(=O)=O)cc1] | N-[4-[2-amino-4-ethyl-5-(4-hydroxyphenyl)-3-pyridyl]phenyl]methanesulfonamide | 19.6 | |
| 31 | 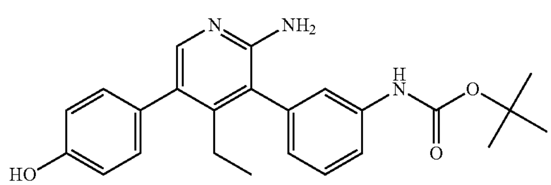 [SMILES: CCc1c(-c2ccc(O)cc2)cnc(N)c1-c1cccc(NC(=O)OC(C)(C)C)c1] | tert-butyl N-[3-[2-amino-4-ethyl-5-(4-hydroxyphenyl)-3-pyridyl]phenyl]carbamate | >20 | |
| 32 | 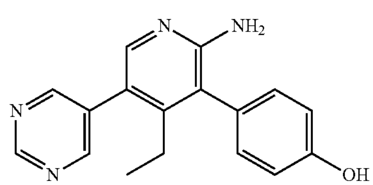 [SMILES: CCc1c(-c2cncnc2)cnc(N)c1-c1ccc(O)cc1] | 4-(2-amino-4-ethyl-5-pyrimidin-5-yl-3-pyridyl)phenol | 69.9 | |
| 33 | 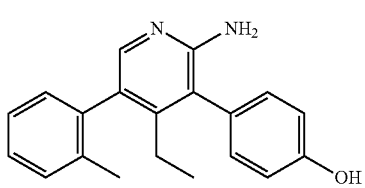 [SMILES: CCc1c(-c2ccccc2C)cnc(N)c1-c1ccc(O)cc1] | 4-[2-amino-4-ethyl-5-(o-tolyl)-3-pyridyl]phenol | >63.3 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 34 | 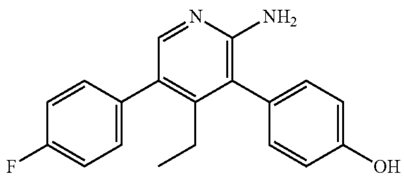 [SMILES: CCc1c(-c2ccc(F)cc2)cnc(N)c1-c1ccc(O)cc1] | 4-[2-amino-4-ethyl-5-(4-fluorophenyl)-3-pyridyl]phenol | 19.9 | |
| 35 | 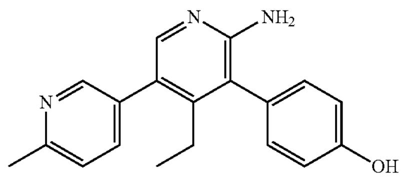 [SMILES: CCc1c(-c2ccc(C)nc2)cnc(N)c1-c1ccc(O)cc1] | 4-[2-amino-4-ethyl-5-(6-methyl-3-pyridyl)-3-pyridyl]phenol | 31.2 | |
| 36 | 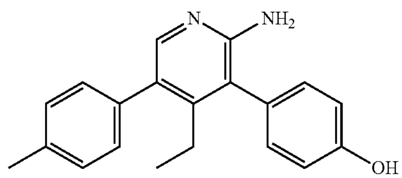 [SMILES: CCc1c(-c2ccc(C)cc2)cnc(N)c1-c1ccc(O)cc1] | 4-[2-amino-4-ethyl-5-(p-tolyl)-3-pyridyl]phenol | 18.1 | |
| 37 | 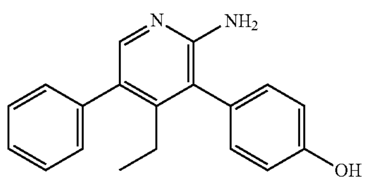 [SMILES: CCc1c(-c2ccccc2)cnc(N)c1-c1ccc(O)cc1] | 4-(2-amino-4-ethyl-5-phenyl-3-pyridyl)phenol | 17.8 | |
| 38 | 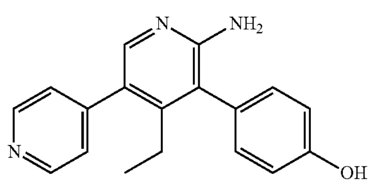 [SMILES: CCc1c(-c2ccncc2)cnc(N)c1-c1ccc(O)cc1] | 4-[2-amino-4-ethyl-5-(4-pyridyl)-3-pyridyl]phenol | 52.4 | |
| 39 | 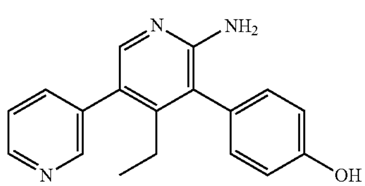 [SMILES: CCc1c(-c2cccnc2)cnc(N)c1-c1ccc(O)cc1] | 4-[2-amino-4-ethyl-5-(3-pyridyl)-3-pyridyl]phenol | 41 | |
| 40 | 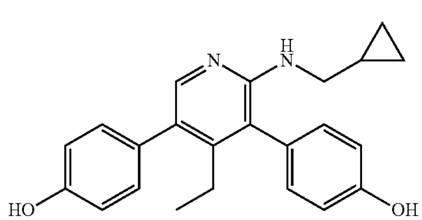 [SMILES: CCc1c(-c2ccc(O)cc2)cnc(NCC2CC2)c1-c1ccc(O)cc1] | 4-[6-(cyclopropylmethylamino)-4-ethyl-5-(4-hydroxyphenyl)-3-pyridyl]phenol | 19.9 | |
| 41 | 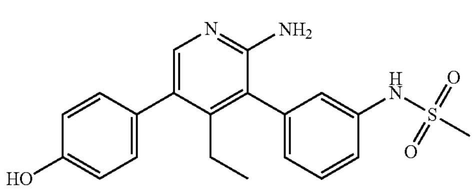 [SMILES: CCc1c(-c2ccc(O)cc2)cnc(N)c1-c1cccc(NS(C)(=O)=O)c1] | N-[3-[2-amino-4-ethyl-5-(4-hydroxyphenyl)-3-pyridyl]phenyl]methanesulfonamide | 118 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 42 | 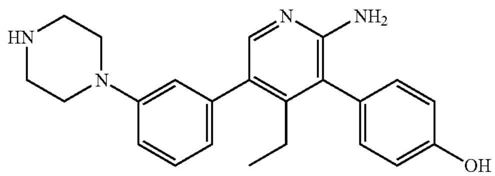 [SMILES: CCc1c(-c2cccc(N3CCNCC3)c2)cnc(N)c1-c1ccc(O)cc1] | 4-[2-amino-4-ethyl-5-(3-piperazin-1-ylphenyl)-3-pyridyl]phenol | 165 | |
| 43 | 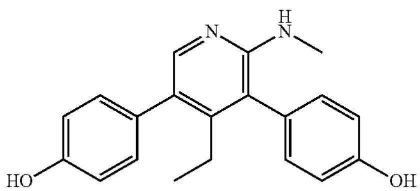 [SMILES: CCc1c(-c2ccc(O)cc2)cnc(NC)c1-c1ccc(O)cc1] | 4-[4-ethyl-5-(4-hydroxyphenyl)-6-(methylamino)-3-pyridyl]phenol | 6.8 | |
| 44 | 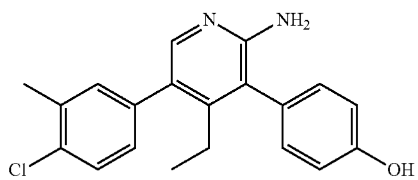 [SMILES: CCc1c(-c2ccc(Cl)c(C)c2)cnc(N)c1-c1ccc(O)cc1] | 4-[2-amino-5-(4-chloro-3-methyl-phenyl)-4-ethyl-3-pyridyl]phenol | >20 | |
| 45 | 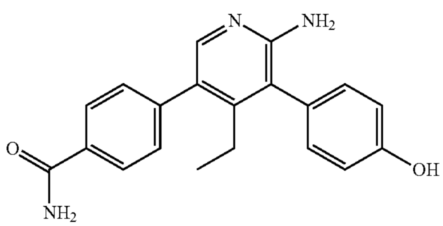 [SMILES: CCc1c(-c2ccc(C(N)=O)cc2)cnc(N)c1-c1ccc(O)cc1] | 4-[6-amino-4-ethyl-5-(4-hydroxyphenyl)-3-pyridyl]benzamide | 2.6 | |
| 46 | 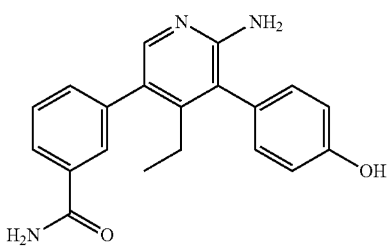 [SMILES: CCc1c(-c2cccc(C(N)=O)c2)cnc(N)c1-c1ccc(O)cc1] | 3-[6-amino-4-ethyl-5-(4-hydroxyphenyl)-3-pyridyl]benzamide | 114 | |
| 47 | 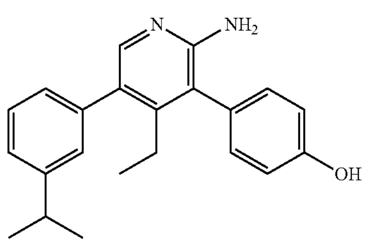 [SMILES: CCc1c(-c2cccc(C(C)C)c2)cnc(N)c1-c1ccc(O)cc1] | 4-[2-amino-4-ethyl-5-(3-isopropylphenyl)-3-pyridyl]phenol | >20 | |
| 48 | 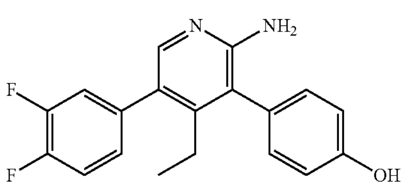 [SMILES: CCc1c(-c2ccc(F)c(F)c2)cnc(N)c1-c1ccc(O)cc1] | 4-[2-amino-5-(3,4-difluorophenyl)-4-ethyl-3-pyridyl]phenol | 11.6 | |

TABLE 1-continued

| No. | Structure | IUPAC_Name | USP7 Ub-Rho preInc (IC50) µmol | USP7 Ub-Rho110 Fluor (IC50) µmol |
|---|---|---|---|---|
| 49 | 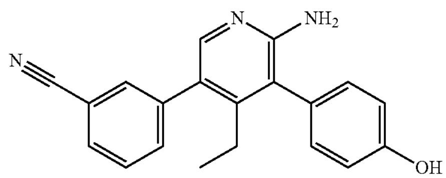 [SMILES: CCc1c(-c2cccc(C#N)c2)cnc(N)c1-c1ccc(O)cc1] | 3-[6-amino-4-ethyl-5-(4-hydroxyphenyl)-3-pyridyl]benzonitrile | 5.4 | |
| 50 | 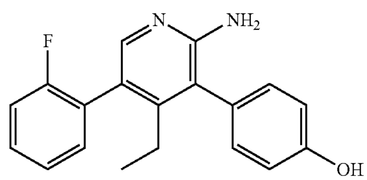 [SMILES: CCc1c(-c2ccccc2F)cnc(N)c1-c1ccc(O)cc1] | 4-[2-amino-4-ethyl-5-(2-fluorophenyl)-3-pyridyl]phenol | 14.2 | |
| 51 | 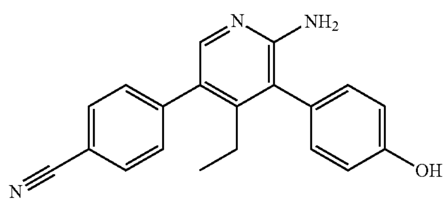 [SMILES: CCc1c(-c2ccc(C#N)cc2)cnc(N)c1-c1ccc(O)cc1] | 4-[6-amino-4-ethyl-5-(4-hydroxyphenyl)-3-pyridyl]benzonitrile | 44.2 | |
| 52 | 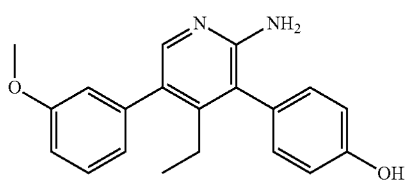 [SMILES: CCc1c(-c2cccc(OC)c2)cnc(N)c1-c1ccc(O)cc1] | 4-[2-amino-4-ethyl-5-(3-methoxyphenyl)-3-pyridyl]phenol | 50.1 | |
| 53 | 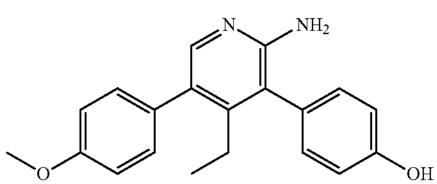 [SMILES: CCc1c(-c2ccc(OC)cc2)cnc(N)c1-c1ccc(O)cc1] | 4-[2-amino-4-ethyl-5-(4-methoxyphenyl)-3-pyridyl]phenol | >20 | |
| 54 | 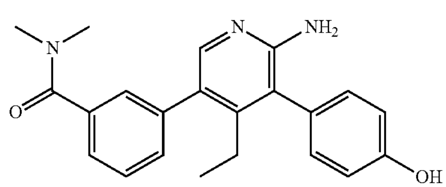 [SMILES: CCc1c(-c2cccc(C(=O)N(C)C)c2)cnc(N)c1-c1ccc(O)cc1] | 3-[6-amino-4-ethyl-5-(4-hydroxyphenyl)-3-pyridyl]-N,N-dimethyl-benzamide | 161 | |
| 55 | 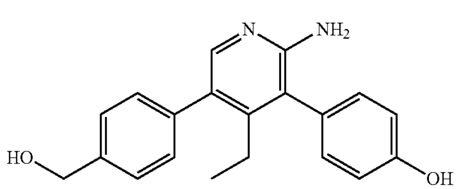 [SMILES: CCc1c(-c2ccc(CO)cc2)cnc(N)c1-c1ccc(O)cc1] | 4-[2-amino-4-ethyl-5-[4-(hydroxymethyl)phenyl]-3-pyridyl]phenol | >20 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 56 | 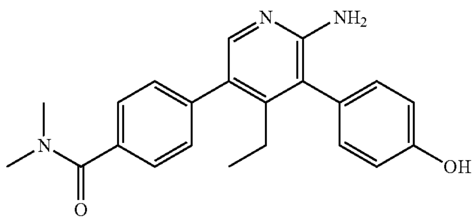 [SMILES: CCc1c(-c2ccc(C(=O)N(C)C)cc2)cnc(N)c1-c1ccc(O)cc1] | 4-[6-amino-4-ethyl-5-(4-hydroxyphenyl)-3-pyridyl]-N,N-dimethyl-benzamide | 75.6+ | |
| 57 | 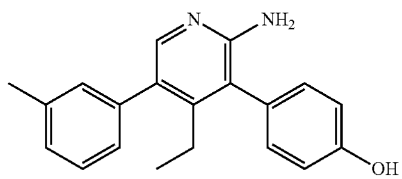 [SMILES: CCc1c(-c2cccc(C)c2)cnc(N)c1-c1ccc(O)cc1] | 4-[2-amino-4-ethyl-5-(m-tolyl)-3-pyridyl]phenol | >20 | |
| 58 | 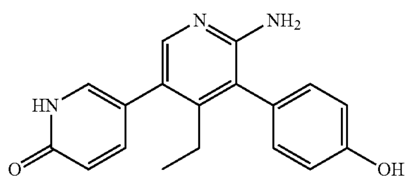 [SMILES: CCc1c(-c2ccc(=O)[nH]c2)cnc(N)c1-c1ccc(O)cc1] | 5-[6-amino-4-ethyl-5-(4-hydroxyphenyl)-3-pyridyl]-1H-pyridin-2-one | 93.3 | |
| 59 | 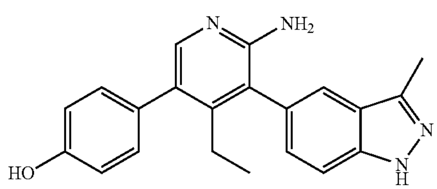 [SMILES: CCc1c(-c2ccc(O)cc2)cnc(N)c1-c1ccc2[nH]nc(C)c2c1] | 4-[6-amino-4-ethyl-5-(3-methyl-1H-indazol-5-yl)-3-pyridyl]phenol | 19.3 | |
| 60 | 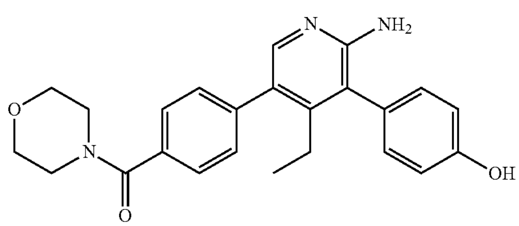 [SMILES: CCc1c(-c2ccc(C(=O)N3CCOCC3)cc2)cnc(N)c1-c1ccc(O)cc1] | [4-[6-amino-4-ethyl-5-(4-hydroxyphenyl)-3-pyridyl]phenyl]-morpholino-methanone | 167 | |
| 61 | 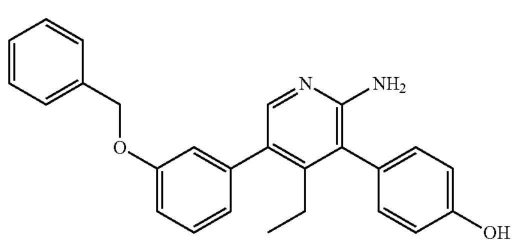 [SMILES: CCc1c(-c2cccc(OCc3ccccc3)c2)cnc(N)c1-c1ccc(O)cc1] | 4-[2-amino-5-(3-benzyloxyphenyl)-4-ethyl-3-pyridyl]phenol | 63.3++ | |
| 62 | 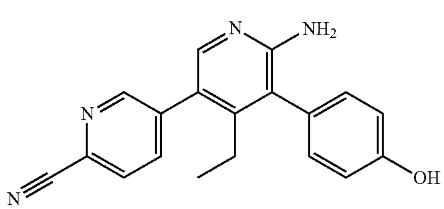 [SMILES: CCc1c(-c2ccc(C#N)nc2)cnc(N)c1-c1ccc(O)cc1] | 5-[6-amino-4-ethyl-5-(4-hydroxyphenyl)-3-pyridyl]pyridine-2-carbonitrile | 39.2 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 63 | 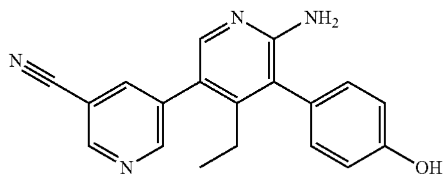 [SMILES: CCc1c(-c2cncc(C#N)c2)cnc(N)c1-c1ccc(O)cc1] | 5-[6-amino-4-ethyl-5-(4-hydroxyphenyl)-3-pyridyl]pyridine-3-carbonitrile | 11.7 | |
| 64 | 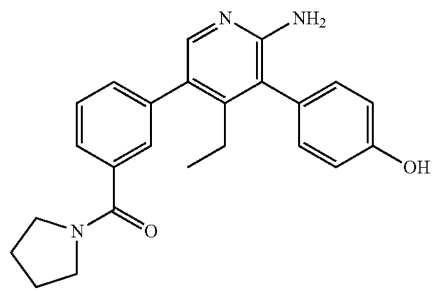 [SMILES: CCc1c(-c2cccc(C(=O)N3CCCC3)c2)cnc(N)c1-c1ccc(O)cc1] | [3-[6-amino-4-ethyl-5-(4-hydroxyphenyl)-3-pyridyl]phenyl]-pyrrolidin-1-yl-methanone | >63.3 | |
| 65 | 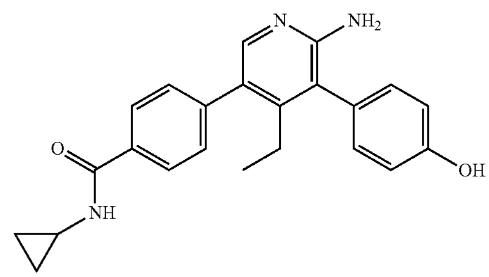 [SMILES: CCc1c(-c2ccc(C(=O)NC3CC3)cc2)cnc(N)c1-c1ccc(O)cc1] | 4-[6-amino-4-ethyl-5-(4-hydroxyphenyl)-3-pyridyl]-N-cyclopropyl-benzamide | 7.7 | |
| 66 | 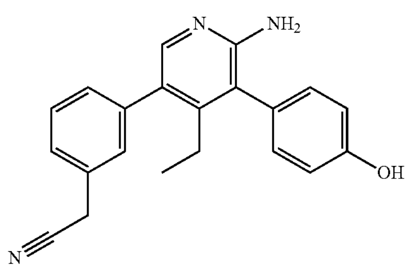 [SMILES: CCc1c(-c2cccc(CC#N)c2)cnc(N)c1-c1ccc(O)cc1] | 2-[3-[6-amino-4-ethyl-5-(4-hydroxyphenyl)-3-pyridyl]phenyl]acetonitrile | 18.3 | |
| 67 | 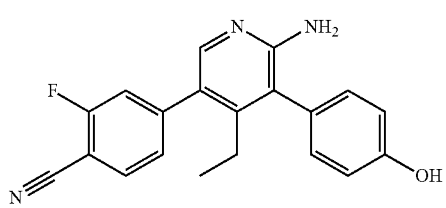 [SMILES: CCc1c(-c2ccc(C#N)c(F)c2)cnc(N)c1-c1ccc(O)cc1] | 4-[6-amino-4-ethyl-5-(4-hydroxyphenyl)-3-pyridyl]-2-fluoro-benzonitrile | 45 | |
| 68 | 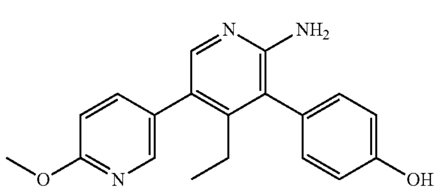 [SMILES: CCc1c(-c2ccc(OC)nc2)cnc(N)c1-c1ccc(O)cc1] | 4-[2-amino-4-ethyl-5-(6-methoxy-3-pyridyl)-3-pyridyl]phenol | >63.3 | |

TABLE 1-continued

| No. | Structure | IUPAC_Name | USP7 Ub-Rho preInc (IC50) µmol | USP7 Ub-Rho110 Fluor (IC50) µmol |
|---|---|---|---|---|
| 69 | 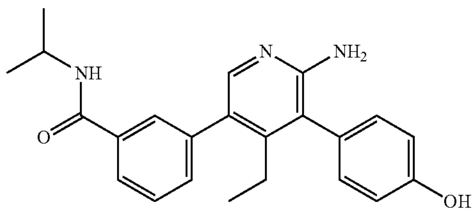 [SMILES: CCc1c(-c2cccc(C(=O)NC(C)C)c2)cnc(N)c1-c1ccc(O)cc1] | 3-[6-amino-4-ethyl-5-(4-hydroxyphenyl)-3-pyridyl]-N-isopropyl-benzamide | >63.3 | |
| 70 | 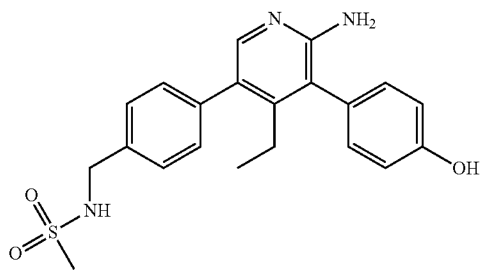 [SMILES: CCc1c(-c2ccc(CNS(C)(=O)=O)cc2)cnc(N)c1-c1ccc(O)cc1] | N-[[4-[6-amino-4-ethyl-5-(4-hydroxyphenyl)-3-pyridyl]phenyl]methyl]methanesulfonamide | 34.4 | |
| 71 | 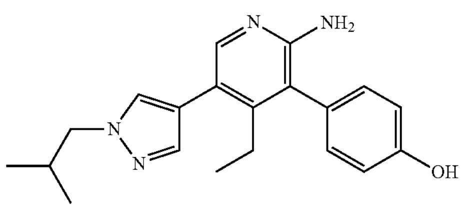 [SMILES: CCc1c(-c2cnn(CC(C)C)c2)cnc(N)c1-c1ccc(O)cc1] | 4-[2-amino-4-ethyl-5-(1-isobutylpyrazol-4-yl)-3-pyridyl]phenol | 70.6 | |
| 72 | 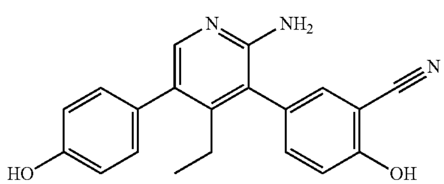 [SMILES: CCc1c(-c2ccc(O)cc2)cnc(N)c1-c1ccc(O)c(C#N)c1] | 5-[2-amino-4-ethyl-5-(4-hydroxyphenyl)-3-pyridyl]-2-hydroxy-benzonitrile | 12.5 | |
| 73 | 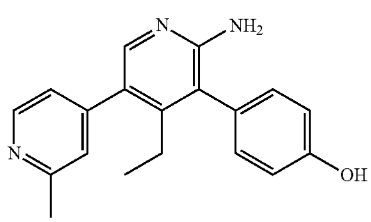 [SMILES: CCc1c(-c2ccnc(C)c2)cnc(N)c1-c1ccc(O)cc1] | 4-[2-amino-4-ethyl-5-(2-methyl-4-pyridyl)-3-pyridyl]phenol | 47.3 | |
| 74 | 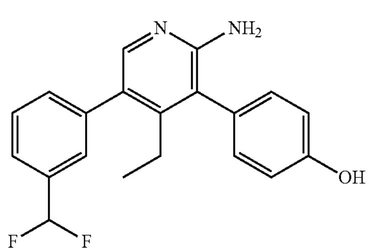 [SMILES: CCc1c(-c2cccc(C(F)F)c2)cnc(N)c1-c1ccc(O)cc1] | 4-[2-amino-5-[3-(difluoromethyl)phenyl]-4-ethyl-3-pyridyl]phenol | 7.8 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 75 | 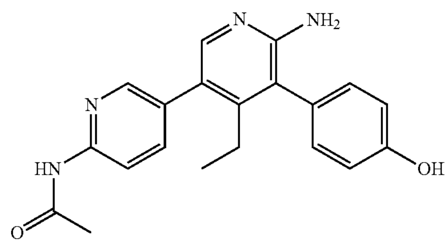 [SMILES: CCc1c(-c2ccc(NC(C)=O)nc2)cnc(N)c1-c1ccc(O)cc1] | N-[5-[6-amino-4-ethyl-5-(4-hydroxyphenyl)-3-pyridyl]-2-pyridyl]acetamide | 3.6 | |
| 76 | 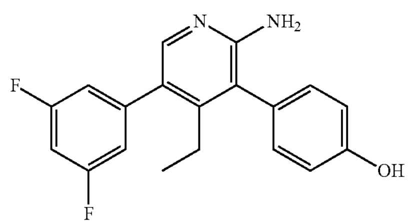 [SMILES: CCc1c(-c2cc(F)cc(F)c2)cnc(N)c1-c1ccc(O)cc1] | 4-[2-amino-5-(3,5-difluorophenyl)-4-ethyl-3-pyridyl]phenol | >20 | |
| 77 | 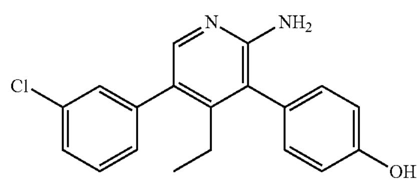 [SMILES: CCc1c(-c2cccc(Cl)c2)cnc(N)c1-c1ccc(O)cc1] | 4-[2-amino-5-(3-chlorophenyl)-4-ethyl-3-pyridyl]phenol | 11 | |
| 78 | 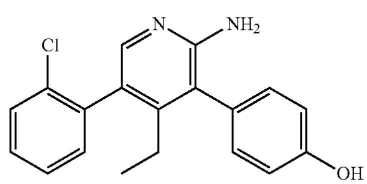 [SMILES: CCc1c(-c2ccccc2Cl)cnc(N)c1-c1ccc(O)cc1] | 4-[2-amino-5-(2-chlorophenyl)-4-ethyl-3-pyridyl]phenol | 15.7 | |
| 79 | 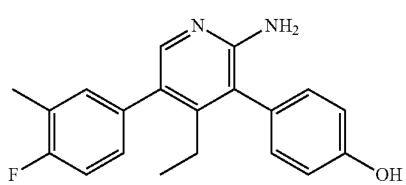 | 4-[2-amino-4-ethyl-5-(4-fluoro-3-methyl-phenyl)-3-pyridyl]phenol | >20 | |
| 80 | 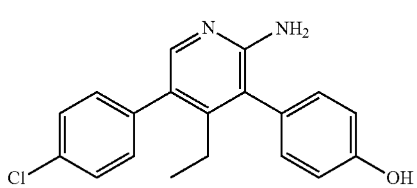 [SMILES: CCc1c(-c2ccc(Cl)cc2)cnc(N)c1-c1ccc(O)cc1] | 4-[2-amino-5-(4-chlorophenyl)-4-ethyl-3-pyridyl]phenol | 17.6 | |
| 81 | 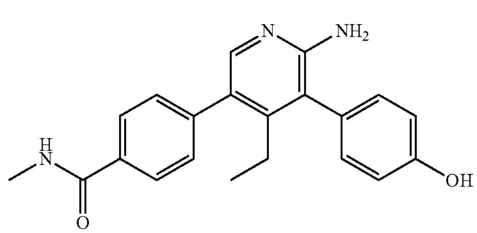 [SMILES: CCc1c(-c2ccc(C(=O)NC)cc2)cnc(N)c1-c1ccc(O)cc1] | 4-[6-amino-4-ethyl-5-(4-hydroxyphenyl)-3-pyridyl]-N-methyl-benzamide | 3.3 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 82 | 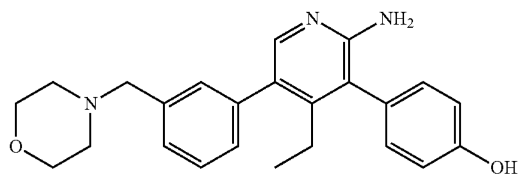 [SMILES: CCc1c(-c2cccc(CN3CCOCC3)c2)cnc(N)c1-c1ccc(O)cc1] | 4-[2-amino-4-ethyl-5-[3-(morpholinomethyl)phenyl]-3-pyridyl]phenol | 18.2 | |
| 83 | 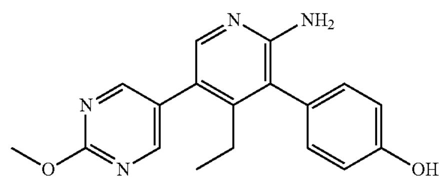 [SMILES: CCc1c(-c2cnc(OC)nc2)cnc(N)c1-c1ccc(O)cc1] | 4-[2-amino-4-ethyl-5-(2-methoxypyrimidin-5-yl)-3-pyridyl]phenol | 136 | |
| 84 | 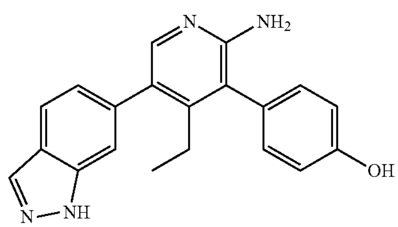 [SMILES: CCc1c(-c2ccc3cn[nH]c3c2)cnc(N)c1-c1ccc(O)cc1] | 4-[2-amino-4-ethyl-5-(1H-indazol-6-yl)-3-pyridyl]phenol | 7.2 | |
| 85 | 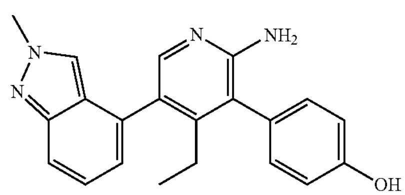 [SMILES: CCc1c(-c2cccc3nn(C)cc23)cnc(N)c1-c1ccc(O)cc1] | 4-[2-amino-4-ethyl-5-(2-methylindazol-4-yl)-3-pyridyl]phenol | 14.6 | |
| 86 | 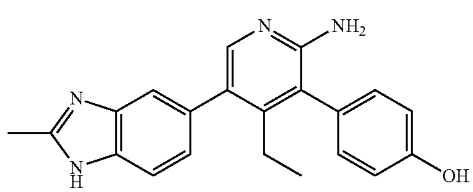 [SMILES: CCc1c(-c2ccc3[nH]c(C)nc3c2)cnc(N)c1-c1ccc(O)cc1] | 4-[2-amino-4-ethyl-5-(2-methyl-1H-benzimidazol-5-yl)-3-pyridyl]phenol | 13.5 | |
| 87 | 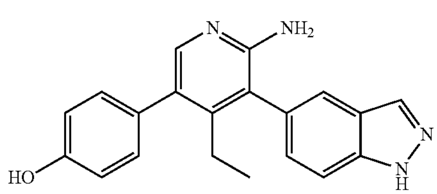 [SMILES: CCc1c(-c2ccc(O)cc2)cnc(N)c1-c1ccc2[nH]ncc2c1] | 4-[6-amino-4-ethyl-5-(1H-indazol-5-yl)-3-pyridyl]phenol | 2.1 | |
| 88 | 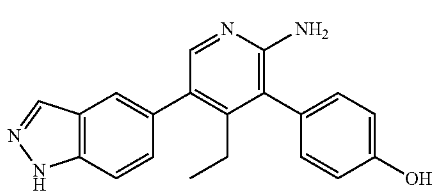 [SMILES: CCc1c(-c2ccc3[nH]ncc3c2)cnc(N)c1-c1ccc(O)cc1] | 4-[2-amino-4-ethyl-5-(1H-indazol-5-yl)-3-pyridyl]phenol | 2.1 | |

TABLE 1-continued

| No. | Structure | IUPAC_Name | USP7 Ub-Rho preInc (IC50) μmol | USP7 Ub-Rho110 Fluor (IC50) μmol |
|---|---|---|---|---|
| 89 | 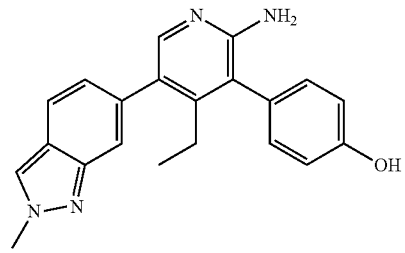 [SMILES: CCc1c(-c2ccc3cn(C)nc3c2)cnc(N)c1-c1ccc(O)cc1] | 4-[2-amino-4-ethyl-5-(2-methylindazol-6-yl)-3-pyridyl]phenol | 63.3++ | |
| 90 | 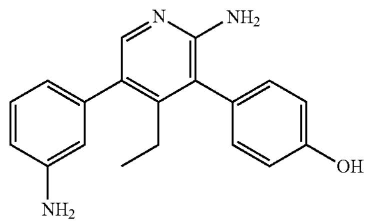 [SMILES: CCc1c(-c2cccc(N)c2)cnc(N)c1-c1ccc(O)cc1] | 4-[2-amino-5-(3-aminophenyl)-4-ethyl-3-pyridyl]phenol | 19.2 | |
| 91 | 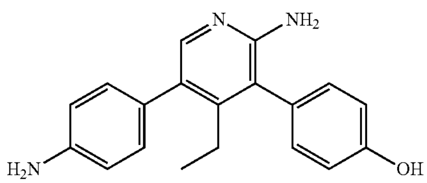 [SMILES: CCc1c(-c2ccc(N)cc2)cnc(N)c1-c1ccc(O)cc1] | 4-[2-amino-5-(4-aminophenyl)-4-ethyl-3-pyridyl]phenol | 47 | |
| 92 | 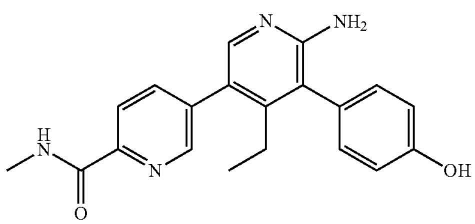 [SMILES: CCc1c(-c2ccc(C(=O)NC)nc2)cnc(N)c1-c1ccc(O)cc1] | 5-[6-amino-4-ethyl-5-(4-hydroxyphenyl)-3-pyridyl]-N-methyl-pyridine-2-carboxamide | 1.5 | |
| 93 | 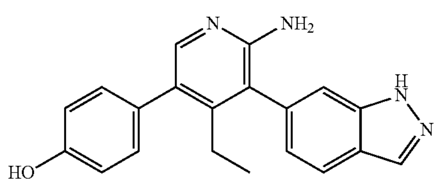 [SMILES: CCc1c(-c2ccc(O)cc2)cnc(N)c1-c1ccc2cn[nH]c2c1] | 4-[6-amino-4-ethyl-5-(1H-indazol-6-yl)-3-pyridyl]phenol | 13.8 | |
| 94 | 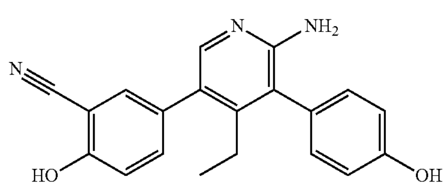 [SMILES: CCc1c(-c2ccc(O)c(C#N)c2)cnc(N)c1-c1ccc(O)cc1] | 5-[6-amino-4-ethyl-5-(4-hydroxyphenyl)-3-pyridyl]-2-hydroxy-benzonitrile | 9.6 | |
| 95 | 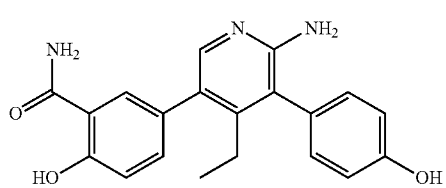 [SMILES: CCc1c(-c2ccc(O)c(C(N)=O)c2)cnc(N)c1-c1ccc(O)cc1] | 5-[6-amino-4-ethyl-5-(4-hydroxyphenyl)-3-pyridyl]-2-hydroxy-benzamide | 106 | |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with USP7 such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

Based on expression analysis, immunohistochemical analysis and on cell line profiling, malignancies of the colon, breast, cervix, stomach, lung, and multiple myeloma are most likely to respond to USP7 antagonists Pharmaceutical Formulations In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, an anti-inflammatory agent, an immunomodulatory agent, chemotherapeutic agent, an apoptosis-enhancer, a neurotropic factor, an agent for treating cardiovascular disease, an agent for treating liver disease, an antiviral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 1

4-[6-amino-5-(4-hydroxyphenyl)-4-methyl-3-pyridyl]phenol 1

Following the procedures of Examples 5-7, 1 was prepared. LCMS: (0-60, AB, 2 min), 0.927 min, MS=293.1 [M+1]. $^1$H NMR (400 MHz, MeOD-d$_4$) δ 9.55-9.37 (br, 2H), 8.14 (s, 1H), 7.08 (d, J=8.4 Hz, 4H), 7.03 (d, J=8.8 Hz, 2H), 6.88 (d, J=8.8 Hz, 2H), 6.78 (d, J=8.8 Hz, 2H), 4.96 (br, 2H), 1.80 (s, 3H).

Example 2

4-[6-amino-4-ethyl-5-(4-hydroxyphenyl)-3-pyridyl]phenol 2

Following the procedures of Examples 5-7 and 15, 2 was prepared. LCMS: (5-95, AB, 1.5 min), 0.694 min, MS=306.9 [M+1]. $^1$H NMR (400 MHz, MeOD-d$_4$) δ 8.27 (s, 1H), 7.62 (s, 1H), 7.15-7.09 (m, 4H), 6.95 (d, J=9.2 Hz, 2H), 6.83 (d, J=8.8 Hz, 2H), 2.39 (q, 2H), 0.70 (t, J=7.2 Hz, 3H)

Example 3

4-[6-amino-5-(4-hydroxyphenyl)-4-isopropyl-3-pyridyl]phenol 3

Following the procedures of Examples 5-7, 3 was prepared. LCMS: (10-80, AB, 2 min), 0.923 min, MS=321.1 [M+1]. $^1$H NMR (400 MHz, MeOD-d$_4$) δ 9.54-9.41 (br, 2H), 8.14 (s, 1H), 7.58 (s, 1H), 7.05-7.00 (m, 4H), 6.87 (d, J=8.4 Hz, 2H), 6.76 (d, J=8.4 Hz, 2H), 4.78 (s, 2H), 2.90-2.82 (m, 1H), 0.78 (t, J=7.2 Hz, 6H).

Example 4

4-[6-amino-5-(4-hydroxyphenyl)-4-methoxy-3-pyridyl]phenol 4

Following the procedures of Examples 5-7, 4 was prepared. $^1$H NMR (400 MHz, DMSO-d6) δ 9.50 (s, 1H), 9.39 (d, J=13.4 Hz, 1H), 7.82 (s, 1H), 7.29-7.21 (m, 2H), 7.17-7.08 (m, 2H), 6.90-6.75 (m, 4H), 5.18 (s, 2H), 3.09 (s, 3H). M+H (m/z) 309

Example 5

4-[6-amino-5-(4-hydroxyphenyl)-4-(trifluoromethyl)-3-pyridyl]phenol 5

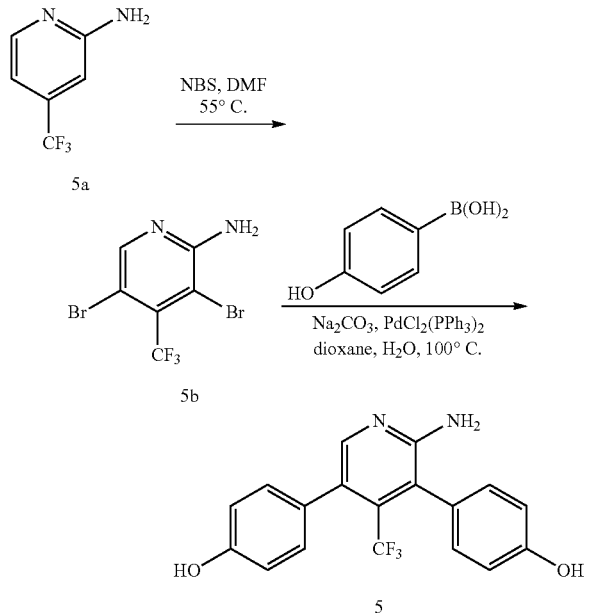

To a solution of 4-(trifluoromethyl)pyridin-2-amine 5a (1.0 g, 6.17 mmol) in DMF (20 mL) was added NBS (2.31 g, 12.95 mmol) at r.t. After the mixture was stirred overnight at 55° C., it was poured into water (50 mL), and extracted with DCM (50 mL×3). The combined organic layers was washed with brine (50 mL), and dried over Na$_2$SO$_4$, concentrated and purified by column (PE:EtOAc=5:1 to 3:1) to give 3,5-dibromo-4-(trifluoromethyl)pyridin-2-amine 5b (1.2 g, yield 61%).

To a solution of 5b (100 mg, 0.32 mmol) in dioxane (10 mL)/H$_2$O (2 mL), was added (4-hydroxyphenyl)boronic acid (108 mg, 0.78 mmol), Na$_2$CO$_3$ (331 mg, 3.13 mmol), and Pd(PPh$_3$)$_2$Cl$_2$ (32.9 mg, 0.047 mmol). The mixture was stirred at 90-100° C. for 3 h, and poured into water (10 mL). The resulting mixture was extracted with EtOAc (10 mL×2). The combined organic layers was washed with brine (10 mL), and dried over Na$_2$SO$_4$, concentrated and purified by pre-HPLC to give 5 (58.48 mg, 54%). LCMS: (5-95, AB, 1.5 min), 0.718 min, MS=346.8 [M+1]; $^1$H NMR (400 MHz, DMSO-d6) δ 9.82-9.55 (br, 2H), 7.96 (s, 1H), 7.13-7.10 (m, 4H), 6.91 (d, J=8.8 Hz, 2H), 6.81 (d, J=8.8 Hz, 2H).

Example 6

4-[6-amino-5-(4-hydroxyphenyl)-4-propyl-3-pyridyl]phenol 6

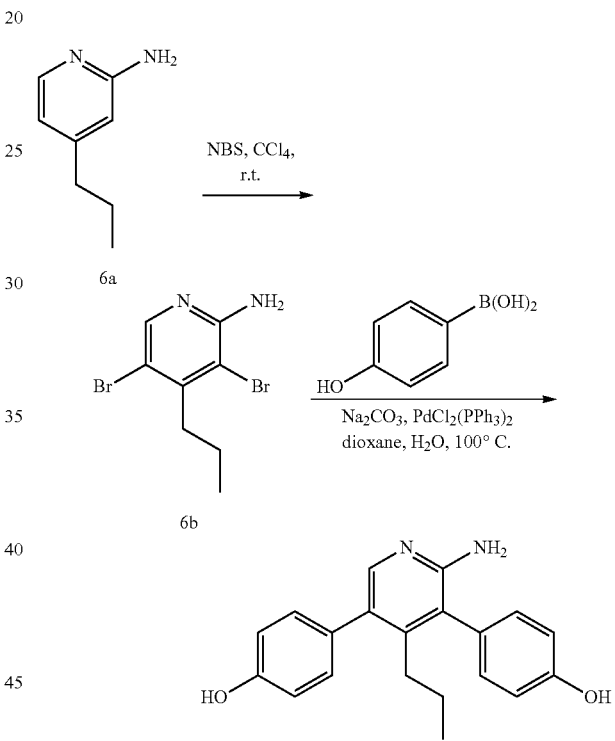

To a solution of 4-propylpyridin-2-amine 6a (500 mg, 3.67 mmol) in CCl$_4$ (10 mL) was added NBS (1.37 g, 7.71 mmol) at r.t. After the mixture was stirred overnight at r.t., it was poured into water (20 mL), and was extracted with DCM (20 mL×3). The combined organic layers was washed with brine (10 mL), and dried over Na$_2$SO$_4$, concentrated and purified by column (PE:EtOAc=5:1 to 3:1) to give 3,5-dibromo-4-propylpyridin-2-amine 6b (800 mg, yield 74%).

To a solution of 6b (100 mg, 0.34 mmol) in dioxane (10 mL)/H$_2$O (2 mL), was added (4-hydroxyphenyl)boronic acid (103 mg, 0.75 mmol), Na$_2$CO$_3$ (360 mg, 3.4 mmol), and Pd(PPh$_3$)$_2$Cl$_2$ (35.8 mg, 0.051 mmol). After the mixture was stirred at 90-100° C. for 3 hours (h), it was poured into water (10 mL). The resulting mixture was extracted with EtOAc (10 mL×2). The combined organic layers was washed with saturated NaCl (10 mL), and dried over Na$_2$SO$_4$, concentrated and purified by pre-HPLC to give 6 (22.7 mg, 21%). LCMS: (5-95, AB, 1.5 min), 0.716 min, MS=320.9 [M+1]. ¹H NMR (400 MHz, MeOD-d₄) δ 7.60 (s, 1H), 7.18-7.12 (m, 4H), 6.99-6.97 (m, 2H), 6.87-6.85 (m, 2H), 2.40-2.36 (m, 2H), 1.17-1.11 (m, 2H), 0.53-0.49 (t, J=7.4 Hz, 3H).

Example 7

4-[6-amino-4-ethyl-5-(4-hydroxyphenyl)-3-pyridyl]-3-fluoro-phenol 7

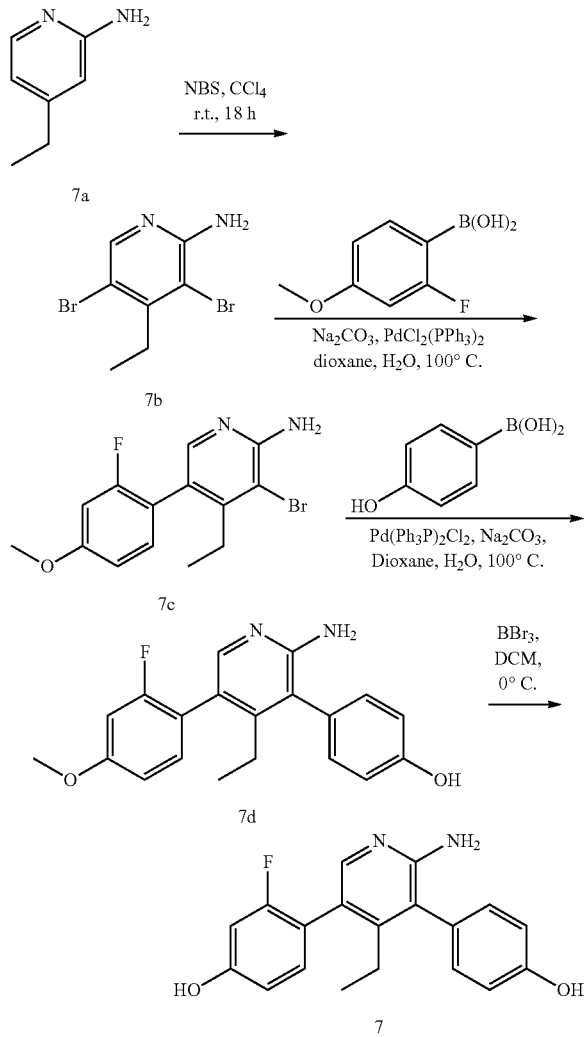

To a solution of 4-ethylpyridin-2-amine 7a (1.0 g, 8.19 mmol) in CCl₄ (20 mL) was added N-bromosuccinimide (NBS, 3.06 g, 17.19 mmol) at room temperature (r.t.). After the mixture was stirred overnight, it was put into water (50 mL), and extracted with DCM (50 mL×3). The combined organic layers was washed with brine (50 mL), dried over Na₂SO₄, concentrated and purified by column (PE:EtOAc=5:1 to 3:1) to give 3,5-dibromo-4-ethylpyridin-2-amine 7b (1.5 g, yield 65.5%).

To a solution of 7b (600 mg, 2.14 mmol) in dioxane (10 mL)/H₂O (2 mL), was added (2-fluoro-4-methoxyphenyl) boronic acid (327.8 mg, 1.93 mmol), Na₂CO₃ (681.45 mg, 6.43 mmol), and Pd(PPh₃)₂Cl₂ (150.43 mg, 0.214 mmol). Then the mixture was stirred at 90-100° C. for 3 h, and poured into water (20 mL). The mixture was extracted with EtOAc (50 mL×2). The combined organic layers was washed with sat NaCl (30 mL), and dried over Na₂SO₄, concentrated and purified by column (PE:EtOAc=3:1 to 1:1) to give 3-bromo-4-ethyl-5-(2-fluoro-4-methoxyphenyl)pyridin-2-amine 7c (300 mg, yield 63%).

To a solution of 7c (300 mg, 0.92 mmol) in dioxane (10 mL)/H₂O (2 mL), was added (4-hydroxyphenyl)boronic acid (191 mg, 1.38 mmol), Na₂CO₃ (293 mg, 2.77 mmol), and Pd(PPh₃)₂Cl₂ (65 mg, 0.092 mmol). After the mixture was stirred at 90-100° C. for 3 h, it was poured into water (20 mL). The mixture was extracted with EtOAc (50 mL×2). The combined organic layers was washed with brine (30 mL), dried over Na₂SO₄, concentrated and purified by column (PE:EtOAc=3:1 to 1:1) to give 4-(2-amino-4-ethyl-5-(2-fluoro-4-methoxyphenyl)pyridin-3-yl)phenol 7d (200 mg, yield 64%).

To a solution of 7d (200 mg, 0.59 mmol) in DCM (10 mL) was added was added BBr₃ (0.5 mL) dropwise at 0° C. with stirring. After the mixture was stirred at r.t. for 2 h, it was quenched by addition of methanol (10 mL). The pH was adjusted to about 7 with ammonium hydroxide. The residue was purified by pre-HPLC to give 7 (64.2 mg, yield 34%). LCMS: (5-95, AB, 1.5 min), 0.709 min, MS=324.9 [M+1]; ¹H NMR (400 MHz, MeOD-d₄) δ 7.66 (s, 1H), 7.17-7.12 (m, 3H), 7.00-6.97 (m, 2H), 6.72-6.70 (m, 1H), 6.65-6.61 (m, 1H), 2.35 (q, 2H), 0.73-0.70 (t, J=7.6 Hz, 3H).

Example 8

N-[3-[6-amino-4-ethyl-5-(4-hydroxyphenyl)-3-pyridyl]phenyl]acetamide 8

Following the procedure of Examples 5-7, 8 was prepared. M+H (m/z) 348.

Example 9

4-[6-amino-4-cyclopropyl-5-(4-hydroxyphenyl)-3-pyridyl]phenol 9

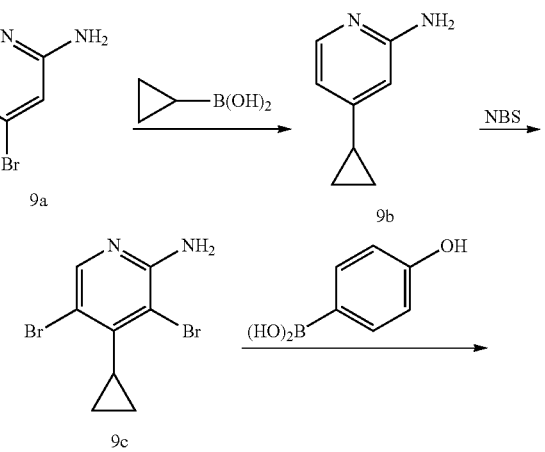

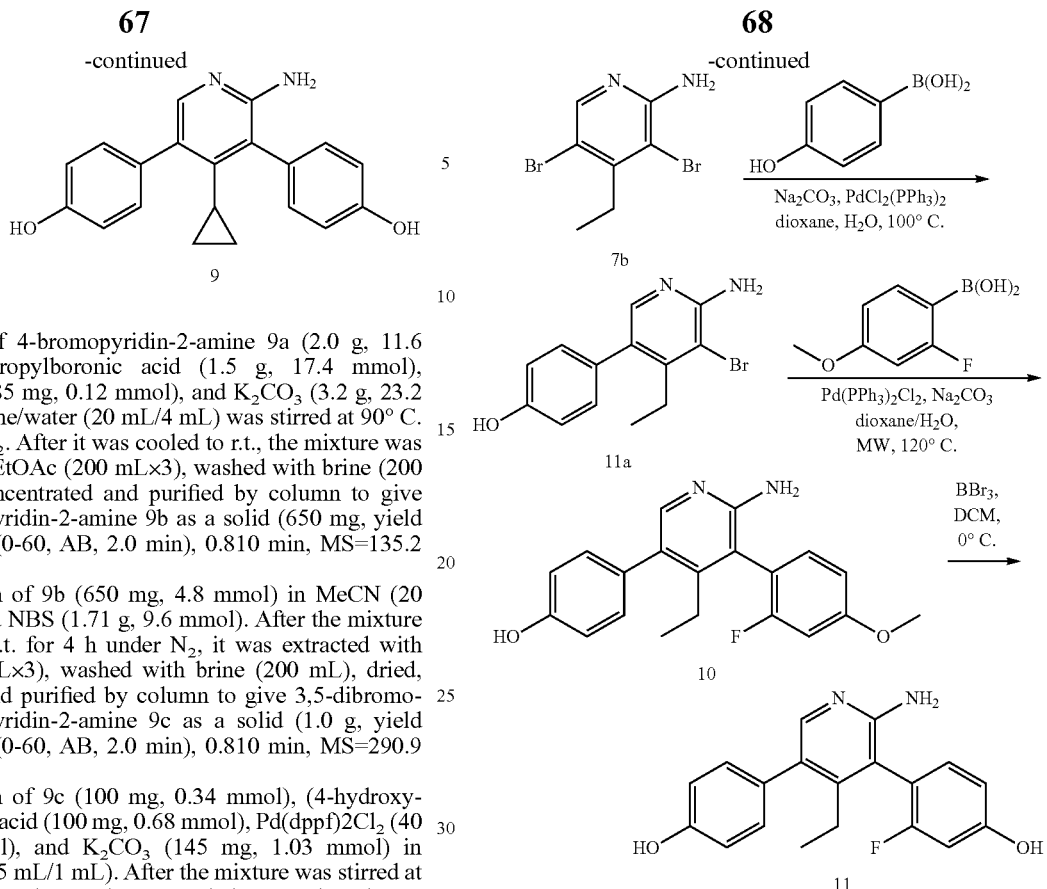

A mixture of 4-bromopyridin-2-amine 9a (2.0 g, 11.6 mmol), cyclopropylboronic acid (1.5 g, 17.4 mmol), Pd(dppf)2Cl$_2$ (85 mg, 0.12 mmol), and K$_2$CO$_3$ (3.2 g, 23.2 mmol) in dioxane/water (20 mL/4 mL) was stirred at 90° C. for 4 h under N$_2$. After it was cooled to r.t., the mixture was extracted with EtOAc (200 mL×3), washed with brine (200 mL), dried, concentrated and purified by column to give 4-cyclopropylpyridin-2-amine 9b as a solid (650 mg, yield 42%). LCMS: (0-60, AB, 2.0 min), 0.810 min, MS=135.2 [M+1]

To a solution of 9b (650 mg, 4.8 mmol) in MeCN (20 mL), was added NBS (1.71 g, 9.6 mmol). After the mixture was stirred at r.t. for 4 h under N$_2$, it was extracted with EtOAc (100 mL×3), washed with brine (200 mL), dried, concentrated and purified by column to give 3,5-dibromo-4-cyclopropylpyridin-2-amine 9c as a solid (1.0 g, yield 71%). LCMS: (0-60, AB, 2.0 min), 0.810 min, MS=290.9 [M+1]

To a solution of 9c (100 mg, 0.34 mmol), (4-hydroxyphenyl)boronic acid (100 mg, 0.68 mmol), Pd(dppf)2Cl$_2$ (40 mg, 0.05 mmol), and K$_2$CO$_3$ (145 mg, 1.03 mmol) in dioxane/water (5 mL/1 mL). After the mixture was stirred at 100° C. for 4 h under N$_2$, it was cooled to r.t. The mixture was extracted with EtOAc (20 mL×3), washed with brine (20 mL), dried, concentrated and purified by Pre-HPLC to give 9 (3.3 mg, yield: 3%). LCMS: (5-95, AB, 1.5 min), 0.810 min, MS=318.9 [M+1]. $^1$H NMR (400 MHz, Methanol-d4) δ 7.68 (s, 1H), 7.29-7.22 (m, 4H), 7.00 (d, J=8.8, 2H), 6.88 (d, J=8.8, 2H), 1.91-1.84 (m, 1H), 0.48-0.43 (m, 2H), 0.04-0.00 (m, 2H)

Example 10

4-[6-amino-4-ethyl-5-(2-fluoro-4-methoxy-phenyl)-3-pyridyl]phenol 10

Following the procedures of Example 11, 10 was prepared. LCMS: (5-95, AB, 1.5 min), 0.744 min, MS=338.8 [M+1]. $^1$H NMR (400 MHz, MeOD-d$_4$) δ 7.67 (s, 1H), 7.28-7.18 (m, 3H), 6.99-6.87 (m, 4H), 3.88 (s, 3H), 2.50-2.38 (m, 2H), 0.74-0.71 (t, J=7.4 Hz, 3H)

Example 11

4-[6-amino-4-ethyl-5-(2-fluoro-4-methoxy-phenyl)-3-pyridyl]phenol 11

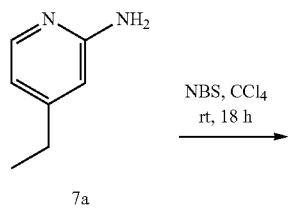

Following Example 7, to a solution of 4-ethylpyridin-2-amine 7a (1.0 g, 8.19 mmol) in CCl$_4$ (20 mL) was added NBS (3.06 g, 17.19 mmol) at r.t. After the mixture was stirred overnight, it was pour into water (50 mL), and extracted with DCM (50 mL×3). The combined organic layers was washed with brine (50 mL), dried over Na$_2$SO$_4$, concentrated and purified by column (PE:EtOAc=5:1 to 3:1) to give 3,5-dibromo-4-ethylpyridin-2-amine 7b (1.6 g, yield 70%).

To a solution of 7b (1.6 g, 5.76 mmol) in dioxane (15 mL)/H$_2$O (3 mL), was added (4-hydroxyphenyl)boronic acid (709 mg, 5.14 mmol), Na$_2$CO$_3$ (1.82 g, 17.15 mmol), and Pd(PPh$_3$)$_2$Cl$_2$ (401 mg, 0.57 mmol). After the mixture was stirred at 90-100° C. for 3 h, it was poured into water (20 mL). The resulting mixture was extracted with EtOAc (50 mL×2). The combined organic layers was washed with sat NaCl (30 mL), and dried over Na$_2$SO$_4$, concentrated and purified by pre-HPLC to give 4-(6-amino-5-bromo-4-ethyl-pyridin-3-yl)phenol 11a (380 mg, yield 22%).

To a solution of 11a (380 mg, 1.3 mmol) in dioxane (4 mL)/H$_2$O (0.5 mL), was added (2-fluoro-4-methoxyphenyl) boronic acid (330 mg, 1.94 mmol), Na$_2$CO$_3$ (412 mg, 3.89 mmol), and Pd(PPh$_3$)$_2$Cl$_2$ (91 mg, 0.061 mmol). After the mixture was purged and heated under microwave irradiation at 120° C. for 30 min, it was poured into water (20 mL). The resulting mixture was extracted with EtOAc (30 mL×2). The combined organic layers was washed with brine (20 mL), dried over Na$_2$SO$_4$, concentrated and purified by column (PE: EtOAc=3:1 to 1:1) to give 4-[2-amino-4-ethyl-5-(4-hydroxyphenyl)-3-pyridyl]-3-fluoro-phenol 10 (150 mg, yield 34%). LCMS: (5-95, AB, 1.5 min), 0.744 min, MS=338.8 [M+1]. $^1$H NMR (400 MHz, MeOD-d$_4$) δ 7.67 (s, 1H), 7.28-7.18 (m, 3H), 6.99-6.87 (m, 4H), 3.88 (s, 3H), 2.50-2.38 (m, 2H), 0.74-0.71 (t, J=7.4 Hz, 3H)

To a solution of 10 (50 mg, 0.15 mmol) in DCM (6 mL), was added was added BBr₃ (0.3 mL) dropwise with stirring at 0° C. After the mixture was stirred at r.t. for 2 h, it was quenched with methanol (10 mL). The pH was adjusted to around 7 with NH₃/H₂O (ammonium hydroxide). The residue was purified by pre-HPLC to give 11 (28 mg, yield 60%). LCMS: (5-95, AB, 1.5 min), 0.702 min, MS=324.8 [M+1]. ¹H NMR (400 MHz, MeOD-d₄) δ 7.65 (s, 1H), 7.20-7.12 (m, 3H), 6.89-6.71 (m, 4H), 2.50-2.38 (m, 2H), 0.74-0.70 (t, J=7.6 Hz, 3H)

Example 12

4-[2-amino-5-[3-[(dimethylamino)methyl]phenyl]-4-ethyl-3-pyridyl]phenol 12

Following the procedures of Examples 5-7, 12 was prepared. ¹H NMR (400 MHz, DMSO-d6) 9.57 (s, 1H), 7.74 (s, 1H), 7.49 (d, J=5.6 Hz, 3H), 7.08-7.01 (m, 2H), 6.94-6.86 (m, 2H), 5.07 (s, 2H), 4.21 (s, 2H), 2.64 (s, 6H), 0.62 (t, J=7.4 Hz, 3H). M+H (m/z) 348

Example 13

N-[3-[6-amino-4-ethyl-5-(2-thienyl)-3-pyridyl]phenyl]acetamide 13

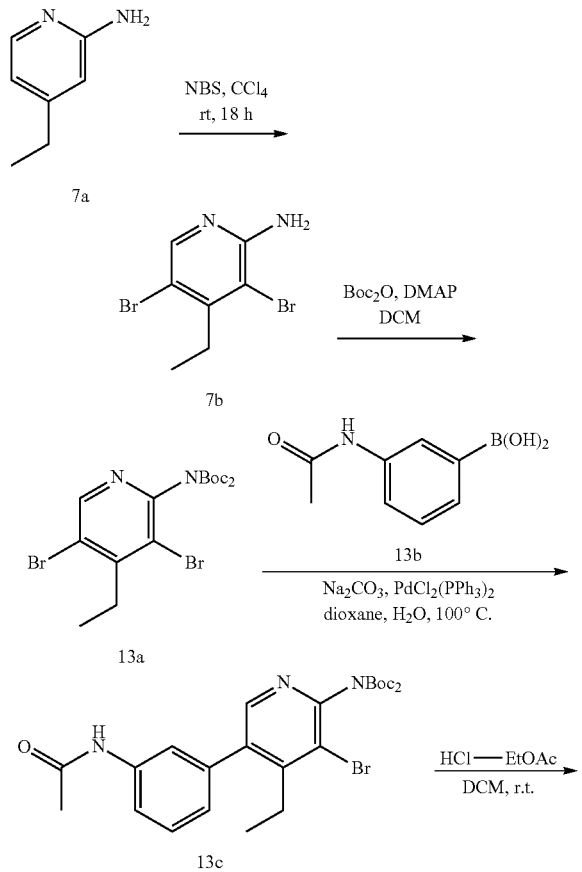

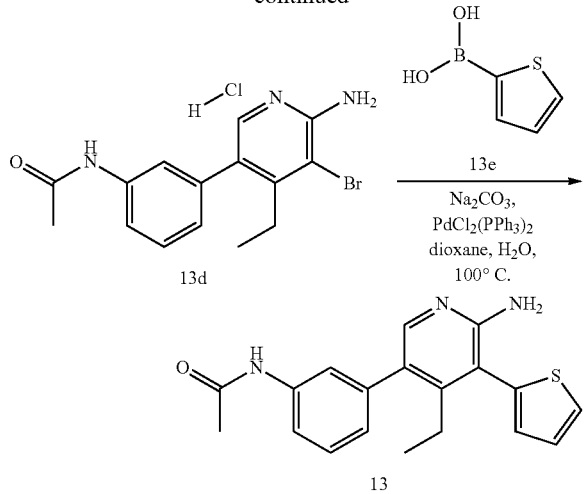

Following Example 7, to a solution of 4-ethylpyridin-2-amine 7a (4.0 g, 32.7 mmol) in CCl₄ (100 mL) was added NBS (12.2 g, 68.8 mmol) at r.t. After the mixture was stirred at r.t. overnight, it was poured into water (50 mL), extracted with DCM (100 mL×3). The combined organic layers was washed with brine (50 mL), dried over Na₂SO₄, concentrated and purified by column (PE:EtOAc=5:1 to 3:1) to give 3,5-dibromo-4-ethylpyridin-2-amine 7b (7.6 g, yield 83%).

To a solution of 7b (6.9 g 24.7 mmol) in THF (100 mL) was added DMAP (3.01 g, 24.7 mmol), and (Boc)₂O (16.1 g, 73.9 mmol). After the mixture was stirred at r.t. for 5 h, it was poured into water (100 mL). It was extracted with EtOAc (100 mL×2) and the combined organic layers was washed with brine (30 mL), dried over Na₂SO₄, concentrated and purified by column (PE:EtOAc=50:1 to 10:1) to give 3,5-dibromo-4-ethylpyridin-2-(bis-tert-butyloxycarbonyl)amine 13a. (10 g, yield 85%).

To a solution of 13a (600 mg, 1.25 mmol) in dioxane (10 mL)/H₂O (2 mL), was added (3-acetamidophenyl)boronic acid 13b (224 mg, 1.25 mmol), Na₂CO₃ (397 mg, 3.75 mmol), and Pd(PPh₃)₂Cl₂ (87.7 mg, 0.12 mmol). After the mixture was stirred at 90-100° C. for 3 h under N₂, it was poured into water (10 mL), and extracted with EtOAc (20 mL×2). The combined organic layers was washed with brine (10 mL), and dried over Na₂SO₄, concentrated and purified by column (PE:EtOAc=3:1 to 1:1) to give N-(3-(6-(bis-tert-butyloxycarbonyl)amino-5-bromo-4-ethylpyridin-3-yl)phenyl)acetamide 13c (370 mg, yield 55%).

To a solution of compound 13c (370 mg, 0.69 mmol) in DCM (10 mL) was added HCl-EtOAc (5 mL) at r.t. After the mixture was stirred at r.t. for 1 h, it was concentrated to give crude N-(3-(6-amino-5-bromo-4-ethylpyridin-3-yl)phenyl)acetamide 13d, which was used for the next step directly (200 mg, 87%)

To a solution of 13d (100 mg, 0.3 mmol) in dioxane/H₂O (3 mL) was added thiophen-2-ylboronic acid 13e (76.6 mg, 0.6 mmol), Na₂CO₃ (159, 1.5 mmol), PdCl₂(PPh₃)₂ (21 mg, 0.03 mmol) at r.t. It was purged and heated under microwave irradiation at 120° C. for 30 min. The reaction mixture was poured into water (10 mL) and was extracted with EtOAc (15 mL×3). The combined organic layers was washed with brine (10 mL), dried over Na₂SO₄, concentrated and purified by prep-HPLC to give 13 (23 mg, yield 24%). LCMS: (5-95, AB, 1.5 min), 0.735 min, MS=337.8 [M+1]. ¹H NMR (400 MHz, MeOD-d₄) δ 7.75-7.73 (m, 3H), 7.53-7.50 (m, 1H), 7.44-7.40 (m, 1H), 7.28-7.26 (m, 1H), 7.20-7.19 (m, 1H), 7.12-7.10 (m, 1H), 2.56-2.51 (m, 2H), 2.13 (s, 3H), 0.82 (t, J=7.6 Hz, 3H).

Example 14

N-[3-[6-amino-4-ethyl-5-(1H-indazol-6-yl)-3-pyridyl]phenyl]acetamide 14

Following the procedures of Example 13, 14 was prepared. LCMS: (5-95, AB, 1.5 min), 0.731 min, MS=371.9 [M+1]. $^1$H NMR (400 MHz, MeOD-d$_4$) δ 8.21 (s, 1H), 8.02 (d, J=8.4 Hz, 1H), 7.83 (s, 1H), 7.76 (s, 1H), 7.61 (s, 1H), 7.48-7.41 (m, 2H), 7.15-7.10 (m, 2H), 2.51-2.44 (m, 2H), 2.14 (s, 3H), 0.75 (t, J=7.6 Hz, 3H)

Example 15

4-[4-ethyl-5-(4-hydroxyphenyl)-6-(propylamino)-3-pyridyl]phenol 15

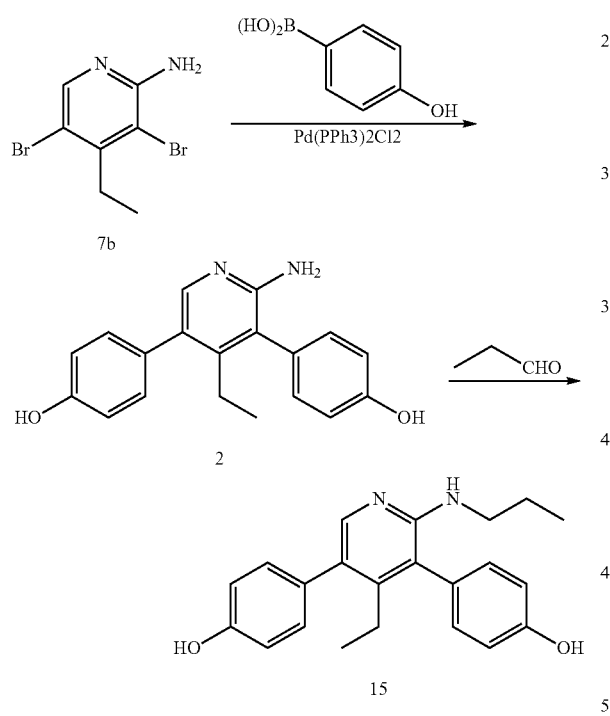

To solution of 3,5-dibromo-4-ethylpyridin-2-amine 7b (600 mg, 2.14 mmol) in dioxane/H$_2$O (15 mL/5 mL) was added (4-hydroxyphenyl)boronic acid (621 mg, 4.50 mmol), Na$_2$CO$_3$ (1.80 g, 17.2 mmol), and Pd(PPh$_3$)$_2$Cl$_2$ (150 mg, 0.21 mmol) under N$_2$. After the reaction mixture was stirred at 100° C. for 5 h under N$_2$, it was concentrated and poured into water. It was extracted with EtOAc (20 mL×3). The organic layer was evaporated and purified by column chromatography on silica gel (PE:EtOAc=3:1) to give 4-[6-amino-4-ethyl-5-(4-hydroxyphenyl)-3-pyridyl]phenol 2 (450 mg yield: 69%).

To a stirred solution of 3 (50 mg, 0.16 mmol) in DCE (3.0 mL) was added propionaldehyde (10.4 mg 0.179 mmol). After the reaction mixture was stirred at 40° C. for 16 h, NaBH(OAc)$_3$ (69.18 mg, 0.326 mmol) was added. The reaction mixture was stirred at 40° C. for 0.5 h, and was concentrated, purified by prep-HPLC to give 15 (3.0 mg, yield: 5%). LCMS: (5-95, AB, 1.5 min), 0.753 min, MS=348.9 [M+1]. $^1$H NMR (400 MHz, Methanol-d4) δ 7.53 (s, 1H), 7.20 (d, J=8.4 Hz, 2H), 7.19 (d, J=8.4 Hz, 2H), 7.01 (d, J=8.8 Hz, 2H), 6.89 (d, J=8.4 Hz, 2H), 3.31-3.29 (m, 2H), 2.45-2.39 (m, 2H), 1.64-1.59 (m, 2H), 0.96-0.92 (t, J=5.2 Hz, 3H), 0.74-0.70 (t, J=7.6 Hz, 3H)

Example 16

4-(6-amino-4-ethyl-5-phenyl-3-pyridyl)phenol 16

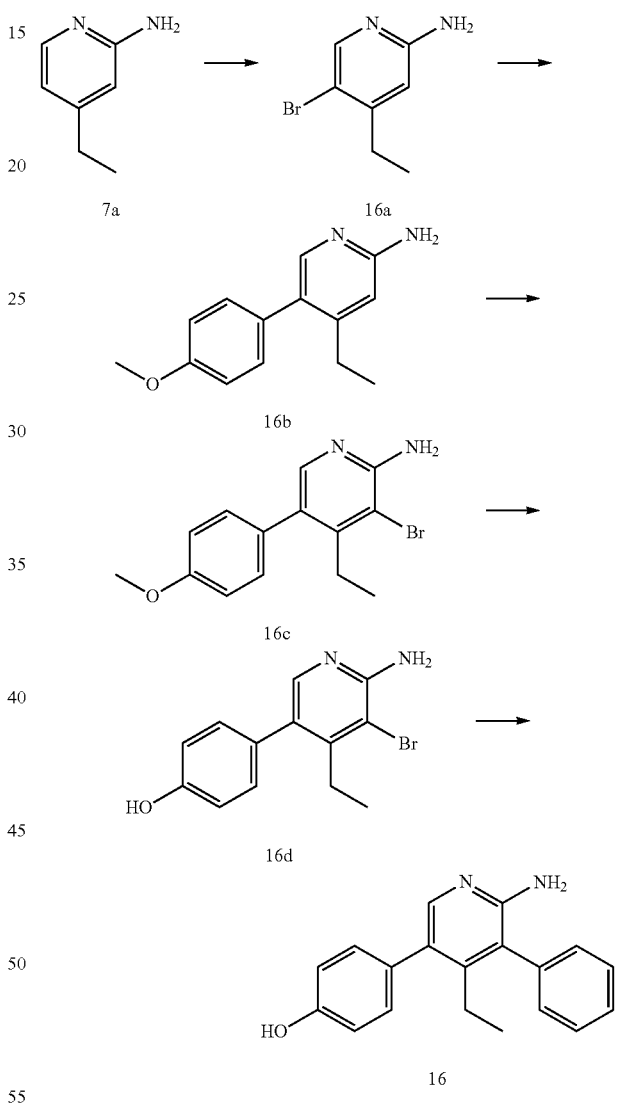

A solution of 4-ethyl-pyridine-2-amine 7a (10 g, 82 mmol) in 300 ml of THF was cooled to 0° C. and charged with N-Bromosuccinimide (14.7 g, 82 mmol). The mixture was then stirred at 0° C. for an additional 15 minutes. The mixture was then concentrated down and the residue was purified by silica-gel chromatography (0-5% MeOH in DCM) to afford 5-bromo-4-ethylpyridin-2-amine 16a (12 g, 72% yield). M+H (m/z)=201

A solution of 16a (1.0 g, 5.0 mmol) in 12 ml of acetonitrile was charged with 4-methoxy-boronic acid (907 mg, 6.0 mmol), bis(diphenylphosphino)ferrocene]dichloropalladium(II) (364 mg, 0.5 mmol), and 12 ml of 1M Potassium Carbonate. The mixture was then heated at 120° C. for 5 minutes. The mixture was then diluted with ethyl acetate and water. The layers were separated aqueous and the organic layer was washed once with water, dried over $Na_2SO_4$, filtered, and concentrated in vacuo. The residue was then purified by silica-gel chromatography (1-15% MeOH in DCM) to afford 4-ethyl-5-(4-methoxyphenyl)pyridin-2-amine 16b (900 mg, 3.9 mmol). M+H (m/z)=229

A solution of 16b (9.5 g, 42 mmol) in 100 ml of THF was charged with N-Bromosuccinimide (7.5 g, 42 mmol) and stirred at room temperature for 15 minutes. The mixture was then concentrated in vacuo and the residue was purified by silica-gel chromatography (0-5% MeOH in DCM) to afford 3-bromo-2-ethyl-4'-methoxybiphenyl-4-amine 16c (8.6 g, 67% yield). M+H (m/z)=306

A solution of 16c (6.6 g, 21 mmol) in 40 ml of THF was charged with 64 ml of 1M Boron Tribromide in DCM. After stirring at room temperature for 15 minutes, the mixture was then cooled 0° C. and charged with 100 ml of saturated sodium carbonate. The layers were separated and the organic was dried over $Mg_2SO_4$, filtered, and concentrated in vacuo to afford 4-(6-amino-5-bromo-4-ethylpyridin-3-yl)phenol 16d (5.7 g, 90% yield). M+H (m/z)=293

A solution of 16d (59 mg, 0.2 mmol) in 0.5 ml of 1,4-dioxane was charged with phenylboronic acid (36 mg, 0.3 mmol), bis(diphenylphosphino)ferrocene]dichloropalladium(II) (14 mg, 0.02 mmol), and 0.5 ml of 1M $K_2CO_3$. The mixture was then heated at 120° C. for 5 minutes. The mixture was then diluted with ethyl acetate and water. The layers were separated and the organic layer was washed once with water, dried over $Na_2SO_4$, filtered, and concentrated in vacuo. The residue was then purified by reverse-phase preparatory HPLC to afford 16 (29 mg, 50% yield). $^1$H NMR (400 MHz, DMSO-$d_6$) δ 9.39 (s, 1H), 7.70 (s, 1H), 7.56-7.46 (m, 2H), 7.46-7.35 (m, 1H), 7.30-7.22 (m, 2H), 7.14-7.06 (m, 2H), 6.84-6.75 (m, 2H), 4.90 (s, 2H), 2.22 (q, J=7.5 Hz, 2H), 0.61 (t, J=7.4 Hz, 3H). M+H (m/z)=291.

Example 17

4-[6-amino-4-ethyl-5-(m-tolyl)-3-pyridyl]phenol 17

Following the procedures of Example 16, 17 was prepared. $^1$H NMR (400 MHz, DMSO-$d_6$) δ 9.39 (s, 1H), 7.69 (s, 1H), 7.39 (t, J=7.6 Hz, 1H), 7.26-7.18 (m, 1H), 7.14-7.01 (m, 4H), 6.84-6.75 (m, 2H), 4.89 (s, 2H), 2.36 (s, 3H), 2.28-2.17 (m, 2H), 0.62 (t, J=7.5 Hz, 3H). M+H (m/z) 305

Example 18

4-[6-amino-5-(3,4-difluorophenyl)-4-ethyl-3-pyridyl]phenol 18

Following the procedures of Example 16, 18 was prepared. $^1$H NMR (400 MHz, DMSO-$d_6$) δ 9.40 (s, 1H), 7.70 (s, 1H), 7.53 (dt, J=10.9, 8.5 Hz, 1H), 7.36 (ddd, J=11.4, 7.9, 2.1 Hz, 1H), 7.14-7.04 (m, 3H), 6.84-6.75 (m, 2H), 5.17 (s, 2H), 2.22 (q, J=7.5 Hz, 2H), 0.63 (t, J=7.4 Hz, 3H). M+H (m/z) 327

Example 19

3-[2-amino-4-ethyl-5-(4-hydroxyphenyl)-3-pyridyl]benzonitrile 19

Following the procedures of Example 16, 19 was prepared. $^1$H NMR (400 MHz, DMSO-$d_6$) δ 9.40 (s, 1H), 7.87 (dt, J=7.8, 1.4 Hz, 1H), 7.77-7.63 (m, 3H), 7.60 (dt, J=7.8, 1.5 Hz, 1H), 7.14-7.05 (m, 2H), 6.85-6.76 (m, 2H), 5.16 (s, 2H), 2.18 (q, J=7.5 Hz, 2H), 0.60 (t, J=7.4 Hz, 3H). M+H (m/z) 316

Example 20

4-[6-amino-4-ethyl-5-(4-methyl sulfonylphenyl)-3-pyridyl]phenol 20

Following the procedures of Example 16, 20 was prepared. $^1$H NMR (400 MHz, DMSO-$d_6$) δ 9.41 (s, 1H), 8.03 (d, J=8.3 Hz, 2H), 7.74 (s, 1H), 7.55 (d, J=8.3 Hz, 2H), 7.10 (d, J=8.5 Hz, 2H), 6.84-6.77 (m, 2H), 5.11 (d, J=5.3 Hz, 2H), 2.21 (q, J=7.5 Hz, 2H), 0.62 (t, J=7.5 Hz, 3H). M+H (m/z) 369

Example 21 tert-butyl N-[4-[2-amino-4-ethyl-5-(4-hydroxyphenyl)-3-pyridyl]phenyl]carbamate 21

Following the procedures of Example 16, 21 was prepared. $^1$H NMR (400 MHz, DMSO-$d_6$) δ 9.44 (s, 1H), 9.38 (s, 1H), 7.67 (s, 1H), 7.61-7.41 (m, 3H), 7.17-7.04 (m, 4H), 6.79 (d, J=8.5 Hz, 2H), 4.90 (s, 2H), 3.27 (s, 1H), 2.23 (q, J=7.4 Hz, 2H), 1.48 (d, J=8.3 Hz, 9H), 0.61 (t, J=7.4 Hz, 3H). M+H (m/z) 406

Example 22

4-[6-amino-4-ethyl-5-(3-morpholinophenyl)-3-pyridyl]phenol 22

Following the procedures of Example 16, 22 was prepared. $^1$H NMR (400 MHz, DMSO-$d_6$) δ 9.38 (s, 1H), 7.68 (s, 1H), 7.35 (dd, J=8.4, 7.4 Hz, 1H), 7.13-7.06 (m, 2H), 6.97 (dd, J=8.4, 2.2 Hz, 1H), 6.85-6.75 (m, 3H), 6.68 (dt, J=7.4, 1.1 Hz, 1H), 4.89 (s, 2H), 3.73 (t, J=4.8 Hz, 5H), 3.21-3.05 (m, 3H), 2.32-2.18 (m, 2H), 0.64 (t, J=7.4 Hz, 3H). M+H (m/z) 376

Example 23 tert-butyl N-[[3-[2-amino-4-ethyl-5-(4-hydroxyphenyl)-3-pyridyl]phenyl]methyl]carbamate 23

Following the procedures of Example 16, 23 was prepared. $^1$H NMR (400 MHz, DMSO-$d_6$) δ 9.39 (s, 1H), 7.69 (s, 1H), 7.45 (t, J=7.5 Hz, 1H), 7.36 (s, 1H), 7.33-7.19 (m, 1H), 7.16-7.05 (m, 4H), 6.80 (d, J=8.4 Hz, 2H), 4.91 (s, 2H), 4.18 (d, J=6.0 Hz, 2H), 2.22 (q, J=7.3 Hz, 2H), 1.37 (s, 9H), 0.61 (t, J=7.4 Hz, 3H). M+H (m/z) 421

Example 24

4-[6-amino-4-ethyl-5-[3-(methoxymethyl)phenyl]-3-pyridyl]phenol 24

Following the procedures of Example 16, 24 was prepared. $^1$H NMR (400 MHz, DMSO-$d_6$) δ 9.39 (s, 1H), 7.70 (s, 1H), 7.49 (t, J=7.9 Hz, 1H), 7.36 (dt, J=7.6, 1.4 Hz, 1H), 7.19 (s, 1H), 7.22-7.15 (m, 1H), 7.14-7.06 (m, 2H), 6.84-6.75 (m, 2H), 4.90 (s, 2H), 4.47 (s, 2H), 3.29 (d, J=13.5 Hz, 3H), 2.22 (qd, J=7.5, 1.9 Hz, 2H), 0.61 (t, J=7.5 Hz, 3H). M+H (m/z) 335

Example 25

4-[6-amino-4-ethyl-5-[4-(methoxymethyl)phenyl]-3-pyridyl]phenol 25

Following the procedures of Example 16, 25 was prepared. $^1$H NMR (400 MHz, DMSO-d$_6$) δ 9.39 (s, 1H), 7.69 (s, 1H), 7.44 (d, J=8.1 Hz, 2H), 7.24 (d, J=8.0 Hz, 2H), 7.10 (d, J=8.5 Hz, 2H), 6.83-6.76 (m, 2H), 4.90 (s, 2H), 4.48 (s, 2H), 3.31 (d, J=27.5 Hz, 3H), 2.22 (q, J=7.4 Hz, 2H), 0.61 (t, J=7.5 Hz, 3H). M+H (m/z) 335

Example 26

4-[6-amino-4-ethyl-5-[3-(morpholinomethyl)phenyl]-3-pyridyl]phenol 26

Following the procedures of Example 16, 26 was prepared. $^1$H NMR (400 MHz, DMSO-d$_6$) δ 9.39 (s, 1H), 7.70 (s, 1H), 7.46 (t, J=7.5 Hz, 1H), 7.34 (dt, J=7.7, 1.4 Hz, 1H), 7.22-7.05 (m, 4H), 6.83-6.76 (m, 2H), 4.91 (s, 2H), 3.60-3.46 (m, 6H), 2.37 (t, J=4.5 Hz, 2H), 2.21 (dt, J=8.2, 6.4 Hz, 2H), 0.60 (t, J=7.4 Hz, 3H). M+H (m/z) 390

Example 27

2-[3-[2-amino-4-ethyl-5-(4-hydroxyphenyl)-3-pyridyl]phenyl]acetonitrile 27

Following the procedures of Example 16, 27 was prepared. $^1$H NMR (400 MHz, DMSO-d$_6$) δ 9.40 (s, 1H), 7.71 (s, 1H), 7.54 (t, J=7.8 Hz, 1H), 7.40 (dt, J=7.6, 1.3 Hz, 1H), 7.23 (dq, J=4.2, 1.5 Hz, 2H), 7.14-7.07 (m, 2H), 6.84-6.76 (m, 2H), 4.97 (s, 2H), 4.10 (s, 2H), 2.21 (q, J=7.5 Hz, 2H), 0.62 (t, J=7.4 Hz, 3H). M+H (m/z) 330

Example 28 tert-butyl N-[4-[2-amino-4-ethyl-5-(4-hydroxyphenyl)-3-pyridyl]phenyl]-N-methyl-carbamate 28

Following the procedures of Example 16, 28 was prepared. $^1$H NMR (400 MHz, DMSO-d$_6$) δ 9.39 (s, 1H), 7.70 (s, 1H), 7.53 (s, 2H), 7.41 (d, J=8.0 Hz, 2H), 7.10 (d, J=8.0 Hz, 2H), 6.80 (d, J=8.0 Hz, 2H), 4.92 (s, 2H), 3.26 (d, J=12.4 Hz, 3H), 2.27-2.19 (m, 2H), 1.41 (s, 9H), 0.62 (t, J=7.4 Hz, 3H). M+H (m/z) 421

Example 29

5-[2-amino-4-ethyl-5-(4-hydroxyphenyl)-3-pyridyl]pyridine-3-carbonitrile 29

Following the procedures of Example 16, 29 was prepared. $^1$H NMR (400 MHz, DMSO-d$_6$) δ 9.42 (s, 1H), 9.04 (d, J=2.0 Hz, 1H), 8.73 (d, J=2.1 Hz, 1H), 8.33-8.27 (m, 1H), 7.76 (s, 1H), 7.14-7.05 (m, 2H), 6.85-6.76 (m, 2H), 5.43 (s, 2H), 2.17 (q, J=7.5 Hz, 2H), 0.61 (t, J=7.5 Hz, 3H). M+H (m/z) 317

Example 30

N-[4-[2-amino-4-ethyl-5-(4-hydroxyphenyl)-3-pyridyl]phenyl]methanesulfonamide 30

Following the procedures of Example 16, 30 was prepared. $^1$H NMR (400 MHz, DMSO-d$_6$) δ 9.81 (s, 1H), 9.39 (s, 1H), 7.68 (s, 1H), 7.32 (d, J=8.6 Hz, 2H), 7.26-7.18 (m, 2H), 7.12-7.05 (m, 2H), 6.83-6.76 (m, 2H), 4.99 (s, 2H), 3.04 (s, 3H), 2.23 (q, J=7.3 Hz, 2H), 0.62 (t, J=7.5 Hz, 3H). M+H (m/z) 384

Example 31 tert-butyl N-[3-[2-amino-4-ethyl-5-(4-hydroxyphenyl)-3-pyridyl]phenyl]carbamate 31

Following the procedures of Example 16, 31 was prepared. $^1$H NMR (400 MHz, DMSO-d$_6$) δ 9.41 (d, J=17.0 Hz, 2H), 7.69 (s, 1H), 7.60-7.44 (m, 2H), 7.50 (s, 2H), 7.10 (d, J=8.4 Hz, 2H), 6.82 (dd, J=18.5, 8.0 Hz, 2H), 4.92 (s, 2H), 2.22 (q, J=7.4 Hz, 2H), 1.47 (s, 9H), 0.64 (t, J=7.5 Hz, 3H). M+H (m/z) 406

Example 32

4-(2-amino-4-ethyl-5-pyrimidin-5-yl-3-pyridyl)phenol 32

Following the procedures of Example 89, 32 was prepared. $^1$H NMR (400 MHz, DMSO-d$_6$) δ 9.51 (s, 1H), 7.59 (s, 1H), 7.33-7.17 (m, 3H), 7.18-7.05 (m, 2H), 7.05 (dt, J=9.2, 2.0 Hz, 2H), 6.92-6.85 (m, 2H), 4.93 (s, 2H), 3.27 (s, 3H), 2.07 (s, 3H), 1.99-1.85 (m, 1H), 0.55 (t, J=7.5 Hz, 3H). M+H (m/z) 293

Example 33

4-[2-amino-4-ethyl-5-(o-tolyl)-3-pyridyl]phenol 33

Following the procedures of Example 89, 33 was prepared. $^1$H NMR (400 MHz, DMSO-d$_6$) δ 9.51 (s, 1H), 7.59 (s, 1H), 7.33-7.17 (m, 3H), 7.18-7.05 (m, 2H), 7.05 (dt, J=9.2, 2.0 Hz, 2H), 6.92-6.85 (m, 2H), 4.93 (s, 2H), 3.27 (s, 3H), 2.07 (s, 3H), 0.55 (t, J=7.5 Hz, 3H). M+H (m/z) 305

Example 34

4-[2-amino-4-ethyl-5-(4-fluorophenyl)-3-pyridyl]phenol 34

Following the procedures of Example 89, 34 was prepared. $^1$H NMR (400 MHz, DMSO-d$_6$) δ 9.52 (s, 1H), 7.69 (s, 1H), 7.39-7.30 (m, 2H), 7.28-7.18 (m, 2H), 7.09-7.01 (m, 2H), 6.92-6.85 (m, 2H), 4.99 (s, 2H), 3.27 (s, 2H), 2.23 (q, J=7.4 Hz, 2H), 0.61 (t, J=7.5 Hz, 3H). M+H (m/z) 309

Example 35

4-[2-amino-4-ethyl-5-(6-methyl-3-pyridyl)-3-pyridyl]phenol 35

Following the procedures of Example 89, 35 was prepared. $^1$H NMR (400 MHz, DMSO-d$_6$) δ 9.52 (s, 1H), 8.38 (d, J=2.2 Hz, 1H), 7.70 (s, 1H), 7.64 (dd, J=7.9, 2.4 Hz, 1H), 7.29 (d, J=7.9 Hz, 1H), 7.11-7.01 (m, 2H), 6.93-6.84 (m, 2H), 5.05 (s, 2H), 3.27 (s, 3H), 2.23 (q, J=7.4 Hz, 2H), 0.61 (t, J=7.4 Hz, 3H). M+H (m/z) 306

Example 36

4-[2-amino-4-ethyl-5-(p-tolyl)-3-pyridyl]phenol 36

Following the procedures of Example 89, 36 was prepared. $^1$H NMR (400 MHz, DMSO-d$_6$) δ 9.51 (s, 1H), 7.67

(s, 1H), 7.26-7.11 (m, 4H), 7.13-7.01 (m, 2H), 6.92-6.84 (m, 2H), 4.97 (s, 2H), 3.27 (s, 1H), 2.34 (s, 3H), 2.25 (q, J=7.4 Hz, 2H), 0.61 (t, J=7.4 Hz, 3H). M+H (m/z) 305

Example 37

4-(2-amino-4-ethyl-5-phenyl-3-pyridyl)phenol 37

Following the procedures of Example 89, 37 was prepared. ¹H NMR (400 MHz, DMSO-d₆) δ 9.52 (s, 1H), 7.70 (s, 1H), 7.46-7.27 (m, 5H), 7.06 (d, J=8.5 Hz, 2H), 6.92-6.85 (m, 2H), 5.01 (s, 2H), 3.27 (s, 2H), 2.26 (q, J=7.5 Hz, 2H), 0.61 (t, J=7.4 Hz, 3H). M+H (m/z) 291

Example 38

4-[2-amino-4-ethyl-5-(4-pyridyl)-3-pyridyl]phenol 38

Following the procedures of Example 89, 38 was prepared. ¹H NMR (400 MHz, DMSO-d₆) δ 9.52 (d, J=12.2 Hz, 1H), 8.62-8.56 (m, 1H), 7.75 (s, 1H), 7.40-7.33 (m, 1H), 7.13-6.95 (m, 2H), 6.93-6.77 (m, 2H), 5.16 (s, 2H), 2.25 (dq, J=32.3, 7.5 Hz, 2H), 0.95 (t, J=7.5 Hz, 1H), 0.63 (t, J=7.5 Hz, 3H). M+H (m/z) 292

Example 39

4-[2-amino-4-ethyl-5-(3-pyridyl)-3-pyridyl]phenol 39

Following the procedures of Example 89, 39 was prepared. M+H (m/z) 292

Example 40

4-[6-(cyclopropylmethylamino)-4-ethyl-5-(4-hydroxyphenyl)-3-pyridyl]phenol 40

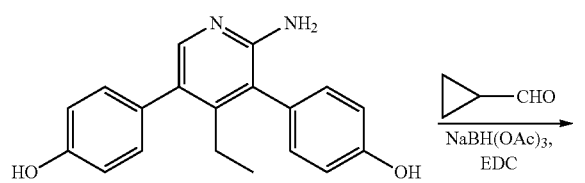

To a stirred solution of 4-[6-amino-4-ethyl-5-(4-hydroxyphenyl)-3-pyridyl]phenol 2 (50 mg, 0.163 mmol) in DCE (3.0 mL) was added cyclopropanecarbaldehyde (22.9 mg 0.36 mmol). After the reaction mixture was stirred at 40° C. for 16 h, NaBH(OAc)₃ (69.2 mg, 0.33 mmol) was added. After the reaction mixture was stirred at 40° C. for 0.5 h, it was concentrated and purified by prep-HPLC to give 40 (7.1 mg, yield: 12%). LCMS: (5-95, AB, 1.5 min), 0.747 min, MS=360.9 [M+1]. ¹H NMR (400 MHz, Methanol-d4) δ 7.54 (s, 1H), 7.20-7.13 (m, 4H), 7.01 (d, J=8.4 Hz, 2H), 6.88 (d, J=8.4 Hz, 2H), 3.24 (d, J=6.8 Hz, 2H), 2.46-2.40 (m, 2H), 1.14-1.11 (m, 1H), 0.74-0.70 (t, J=7.6 Hz, 3H), 0.57-0.52 (m, 2H), 0.27-0.25 (m, 2H)

Example 41

N-[3-[2-amino-4-ethyl-5-(4-hydroxyphenyl)-3-pyridyl]phenyl]methanesulfonamide 41

Following the procedures of Example 16, 41 was prepared. ¹H NMR (400 MHz, DMSO-d₆) δ 9.80 (s, 1H), 9.37 (d, J=13.9 Hz, 1H), 7.70 (s, 1H), 7.46 (t, J=7.9 Hz, 2H), 7.25 (ddd, J=8.2, 2.4, 1.0 Hz, 2H), 7.18-6.95 (m, 2H), 6.79 (dd, J=8.5, 6.5 Hz, 2H), 5.73 (d, J=14.3 Hz, 1H), 3.00 (d, J=4.6 Hz, 3H), 2.22 (q, J=7.5 Hz, 2H), 0.73-0.59 (m, 3H). M+H (m/z) 384

Example 42

4-[2-amino-4-ethyl-5-(3-piperazin-1-ylphenyl)-3-pyridyl]phenol 42

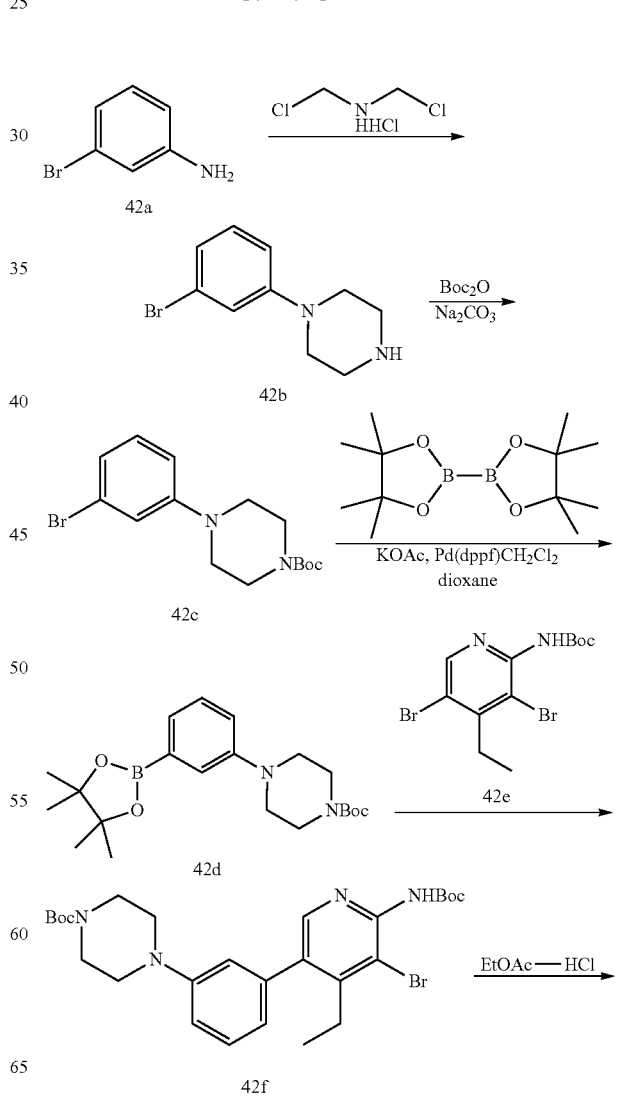

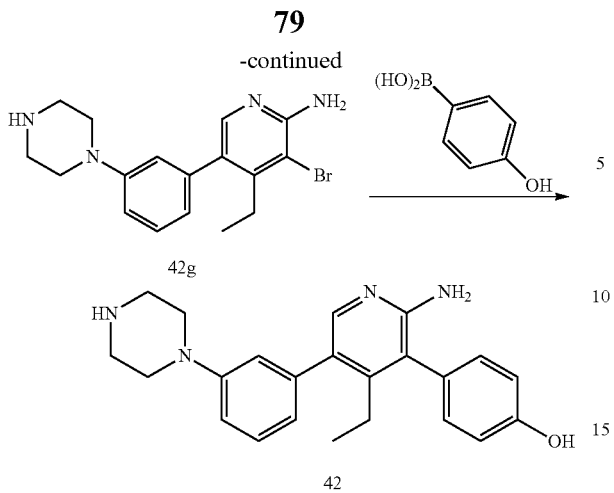

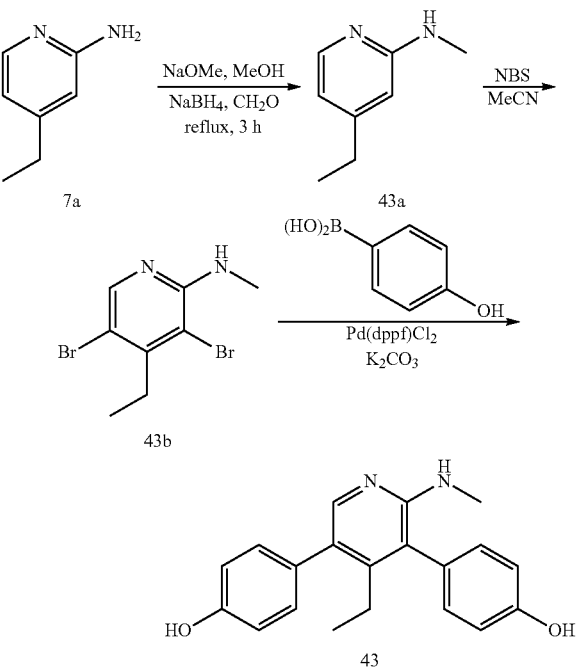

A mixture of 3-bromoaniline 42a (5.0 g, 28.0 mmol) and bis(chloromethyl)amine hydrochloride (4.82 g, 28.01 mmol) in n-BuOH (60 mL) was heated at 118° C. for 48 h. After it was cooled to 25° C., the reaction mixture containing 1-(3-bromophenyl)piperazine 42b was used in next step directly. LCMS: (5-95, AB, 1.5 min), 0.608 min, MS=240.7 [M+1]

To the solution of 42b (6.25 g, 25.9 mmol) in THF—$H_2O$ (1:1, 40 mL) was added $Na_2CO_3$ until basic. $Boc_2O$ (6.79 g, 31.1 mmol) was added, and the reaction mixture was stirred at 25° C. for 10 h. Water (15 mL) was added to the reaction mixture and it was extracted with EtOAc (3×20 mL), dried over $Na_2SO_4$, and purified by column (PE:EtOAc=30:1) to give tert-butyl 4-(3-bromophenyl)piperazine-1-carboxylate 42c (1.94 g, yield: 21.9%)

To a solution of 42c (0.94 g, 2.75 mmol) in dioxane (30 mL) was added 4,4,4',4',5,5,5',5'-octamethyl-2,2'-bi(1,3,2-dioxaborolane) (1.40 g, 5.51 mmol), KOAc (811 mg, 8.26 mmol), Pd(dppf)Cl₂ (0.27 mmol), and dioxane (15 mL). The reaction system was purged and stirred at 110° C. for 5 h. The reaction mixture was cooled to 25° C. and poured into water (15 mL), extracted with EtOAc (20 mL×3). The organic layer was dried over $Na_2SO_4$, concentrated, and by purified by column (PE:EtOAc=15:1-10:1) to give tert-butyl 4-(3-(4,4,5,5-tetramethyl-1,3,2-dioxaborolan-2-yl)phenyl) piperazine-1-carboxylate 42d (0.89 g, yield: 83.2%). LCMS: (5-95, AB, 1.5 min), 1.015 min, MS=388.8 [M+1]

To a solution of 42d (400 mg, 1.03 mmol) in dioxane-$H_2O$ (5 mL) was added tert-butyl (3,5-dibromo-4-ethylpyridin-2-yl)carbamate 42e (391 mg, 1.0 mmol), $K_2CO_3$ (427 mg, 3.09 mmol) and Pd(dppf)Cl₂ (45 mg). The reaction mixture was purged with $N_2$ and heated with microwave irradiation at 120° C. for 50 min. The reaction mixture was cooled to 25° C. then poured to water (15 mL). It was extracted with EtOAc (3×20 mL) and the organic layer was dried over $Na_2SO_4$, concentrated it and purified by column (PE: EtOAc=20:1-5:1) to give tert-butyl 4-(3-(5-bromo-6-((tert-butoxycarbonyl)amino)-4-ethylpyridin-3-yl)phenyl)piperazine-1-carboxylate 42f (250 mg, yield: 43.2%)

To the mixture of 42f (250 mg, 0.445 mmol) in EtOAc (5 mL) was added HCl/EtOAc (10 mL) and stirred at 25° C. for 3 h. It was concentrated to give 3-bromo-4-ethyl-5-(3-(piperazin-1-yl)phenyl)pyridin-2-amine 42g which was used in the next step directly. LCMS: (5-95, AB, 1.5 min), 0.673 min, MS=362.7 [M+1]

To the solution of 42g (140 mg, 0.387 mol) in dioxane-$H_2O$ (5:1, 2.5 mL) added (4-hydroxyphenyl)boronic acid (53 mg, 0.387 mmol), $Na_2CO_3$ (205 mg, 1.94 mmol) and Pd(dppf)Cl₂ (35 mg). The mixture was purged with nitrogen and heated under microwave irradiation at 120° C. for 50 min. The mixture was cooled to 25° C., and added to water (20 mL). It was extracted with EtOAc (30 mL×3), dried over $Na_2SO_4$, concentrated and purified by pre-HPLC to give 42 (48 mg, yield: 33.1%) as white solid. LCMS: (5-95, AB, 1.5 min), 0.669 min, MS=374.9 [M+1]. $^1$H NMR (400 MHz, $CD_3OD$): δ 7.67 (s, 1H), 7.39-7.36 (m, 2H), 7.12-7.10 (d, J=8.4 Hz, 2H), 6.97-6.96 (m, 1H), 6.96-6.94 (m, 3H), 6.91-6.90 (d, J=4.0 Hz, 1H), 3.45-3.36 (m, 4H), 3.31 (s, 4H), 2.42-2.36 (m, 2H), 0.73-0.70 (t, J=7.2 Hz, 3H)

Example 43

4-[4-ethyl-5-(4-hydroxyphenyl)-6-(methyl amino)-3-pyridyl]phenol 43

A solution of 4-ethylpyridin-2-amine 7a (600 mg, 4.92 mmol), formaldehyde, HCHO (590 mg, 19.67 mmol), sodium methoxide, NaOMe (1.3 g, 24.6 mmol) in methanol, MeOH (30 ml) was heated to reflux for 2 h. The mixture was cooled to 0° C. with an ice bath, and NaBH₄ (747 mg, 19.7 mmol) was added. The mixture heated at reflux for 2 h and poured to crushed ice. The mixture was extracted with EtOAc (20 mL×3), and washed with water. The combined extracts was washed with brine, dried over $Na_2SO_4$, and concentrated in vacuum to give 4-ethyl-N-methylpyridin-2-amine 43a as a solid, which was used to next step directly (420 mg, yield 63%)

To a solution of 43a (320 mg, 2.36 mmol) in MeCN (20 mL) was added NBS (1.6 g, 9.4 mmol). The reaction mixture was stirred at r.t. for 4 h under $N_2$. The mixture was extracted with EtOAc (30 mL×3). The combined extracts was washed with brine (30 mL), dried over $Na_2SO_4$, concentrated and purified by column to give 3,5-dibromo-4-ethyl-N-methyl-pyridin-2-amine 43b (EtOAc/PE=1:40) (420 mg, 44%)

To a solution of 43b (100 mg, 0.34 mmol), (4-hydroxy-phenyl)boronic acid (57 mg, 0.41 mmol), Pd(dppf)Cl₂ (5 mg, 0.0068 mmol), and K$_2$CO$_3$ (95 mg, 0.68 mmol) in dioxane/H$_2$O (10 ml/1 mL). The mixture was stirred at 90° C. for 5 h under N$_2$. The mixture was extracted with EtOAc (15×3), washed with brine (20 mL), dry over Na$_2$SO$_4$, concentrated, and purified by pre-HPLC to give 43 (52.1 mg, 47%). LCMS: (5-95, AB, 1.5 min), 0.724 min, MS=320.9 [M+1]. $^1$H NMR (400 MHz, Methanol-d4) δ 7.56 (s, 1H), 7.19 (d, J=8.4 Hz, 2H), 7.13 (d, J=8.4 Hz, 2H), 7.01 (d, J=8.4 Hz, 2H), 6.90 (d, J=8.4 Hz, 2H), 2.97 (s, 3H), 2.46-2.40 (m, 2H), 0.72 (t, J=7.6 Hz, 3H)

Example 44

4-[2-amino-5-(4-chloro-3-methyl-phenyl)-4-ethyl-3-pyridyl]phenol 44

Following the procedures of Example 89, 44 was prepared. $^1$H NMR (400 MHz, DMSO-d$_6$) δ 9.53 (s, 1H), 7.69 (s, 1H), 7.43 (d, J=8.2 Hz, 1H), 7.30 (d, J=2.5 Hz, 1H), 7.16 (dd, J=8.1, 2.2 Hz, 1H), 7.09-7.00 (m, 2H), 6.93-6.85 (m, 2H), 5.01 (s, 2H), 2.36 (s, 3H), 2.24 (q, J=7.4 Hz, 2H), 0.62 (t, J=7.4 Hz, 3H). M+H (m/z) 340

Example 45

4-[6-amino-4-ethyl-5-(4-hydroxyphenyl)-3-pyridyl]benzamide 45

Following the procedures of Example 89, 45 was prepared. $^1$H NMR (400 MHz, DMSO-d$_6$) δ 9.53 (s, 1H), 7.97 (s, 1H), 7.91 (d, J=8.3 Hz, 2H), 7.72 (s, 1H), 7.39 (d, J=8.3 Hz, 2H), 7.33 (s, 1H), 7.10-7.02 (m, 2H), 6.93-6.85 (m, 2H), 5.04 (s, 2H), 2.27 (q, J=7.4 Hz, 2H), 0.61 (t, J=7.4 Hz, 3H). M+H (m/z) 334

Example 46

3-[6-amino-4-ethyl-5-(4-hydroxyphenyl)-3-pyridyl]benzamide 46

Following the procedures of Example 89, 46 was prepared. $^1$H NMR (400 MHz, DMSO-d$_6$) δ 9.53 (s, 1H), 7.99 (s, 1H), 7.84 (dtd, J=7.1, 3.6, 1.9 Hz, 2H), 7.73 (s, 1H), 7.54-7.45 (m, 2H), 7.35 (s, 1H), 7.13-6.94 (m, 2H), 6.93-6.74 (m, 2H), 5.02 (s, 2H), 2.23 (dq, J=20.9, 7.4 Hz, 2H), 0.61 (t, J=7.5 Hz, 3H). M+H (m/z) 334

Example 47

4-[2-amino-4-ethyl-5-(3-isopropylphenyl)-3-pyridyl]phenol 47

Following the procedures of Example 89, 47 was prepared. $^1$H NMR (400 MHz, DMSO-d$_6$) δ 9.51 (s, 1H), 7.70 (s, 1H), 7.32 (t, J=7.6 Hz, 1H), 7.25-7.13 (m, 2H), 7.14-7.01 (m, 3H), 6.93-6.84 (m, 2H), 4.94 (s, 2H), 2.92 (hept, J=6.9 Hz, 1H), 2.24 (q, J=7.4 Hz, 2H), 1.22 (d, J=6.9 Hz, 6H), 0.63 (t, J=7.4 Hz, 3H). M+H (m/z) 333

Example 48

4-[2-amino-5-(3,4-difluorophenyl)-4-ethyl-3-pyridyl]phenol 48

Following the procedures of Example 89, 48 was prepared. $^1$H NMR (400 MHz, DMSO-d$_6$) δ 9.53 (s, 1H), 7.71 (s, 1H), 7.57-7.42 (m, 1H), 7.46-7.36 (m, 1H), 7.21-7.12 (m, 1H), 7.12-7.00 (m, 2H), 6.93-6.85 (m, 2H), 5.06 (s, 2H), 2.25 (q, J=7.4 Hz, 2H), 0.62 (t, J=7.4 Hz, 3H). M+H (m/z) 327

Example 49

3-[6-amino-4-ethyl-5-(4-hydroxyphenyl)-3-pyridyl]benzonitrile 49

Following the procedures of Example 89, 49 was prepared. M+H (m/z) 316

Example 50

4-[2-amino-4-ethyl-5-(2-fluorophenyl)-3-pyridyl]phenol 50

Following the procedures of Example 89, 50 was prepared. $^1$H NMR (400 MHz, DMSO-d$_6$) δ 9.53 (s, 1H), 7.69 (s, 1H), 7.47-7.22 (m, 4H), 7.10-7.02 (m, 2H), 6.93-6.85 (m, 2H), 5.06 (s, 2H), 2.14 (q, J=7.4 Hz, 2H), 0.59 (t, J=7.5 Hz, 3H). M+H (m/z) 333

Example 51

4-[6-amino-4-ethyl-5-(4-hydroxyphenyl)-3-pyridyl]benzonitrile 51

Following the procedures of Example 89, 51 was prepared. $^1$H NMR (400 MHz, DMSO-d$_6$) δ 9.54 (s, 1H), 7.87 (d, J=8.2 Hz, 2H), 7.73 (s, 1H), 7.58-7.51 (m, 2H), 7.11-7.02 (m, 2H), 6.93-6.85 (m, 2H), 5.14 (s, 2H), 2.26 (q, J=7.5 Hz, 2H), 0.61 (t, J=7.5 Hz, 3H). M+H (m/z) 316

Example 52

4-[2-amino-4-ethyl-5-(3-methoxyphenyl)-3-pyridyl]phenol 52

Following the procedures of Example 89, 52 was prepared. $^1$H NMR (400 MHz, DMSO-d$_6$) δ 9.52 (s, 1H), 7.73-7.52 (m, 1H), 7.37-7.28 (m, 1H), 7.09-7.02 (m, 2H), 6.95-6.76 (m, 5H), 4.96 (s, 2H), 3.77 (s, 3H), 2.27 (q, J=7.5 Hz, 2H), 0.64 (t, J=7.4 Hz, 3H). M+H (m/z) 321

Example 53

4-[2-amino-4-ethyl-5-(4-methoxyphenyl)-3-pyridyl]phenol 53

Following the procedures of Example 89, 53 was prepared. $^1$H NMR (400 MHz, DMSO-d$_6$) δ 9.51 (s, 1H), 7.67 (s, 1H), 7.25-7.18 (m, 2H), 7.09-7.01 (m, 2H), 7.01-6.93 (m, 2H), 6.92-6.84 (m, 2H), 4.91 (s, 2H), 3.78 (s, 3H), 2.24 (q, J=7.4 Hz, 2H), 0.62 (t, J=7.5 Hz, 3H). M+H (m/z) 321

Example 54

3-[6-amino-4-ethyl-5-(4-hydroxyphenyl)-3-pyridyl]-N,N-dimethyl-benzamide 54

Following the procedures of Example 89, 54 was prepared. M+H (m/z) 362

Example 55

4-[2-amino-4-ethyl-5-[4-(hydroxymethyl)phenyl]-3-pyridyl]phenol 55

Following the procedures of Example 89, 55 was prepared. $^1$H NMR (400 MHz, DMSO-d$_6$) δ 9.51 (d, J=8.5 Hz, 1H), 7.68 (s, 1H), 7.48-7.32 (m, 2H), 7.29-7.18 (m, 2H), 7.13-6.76 (m, 3H), 5.17 (t, J=5.7 Hz, 2H), 4.95 (s, 1H), 4.53 (d, J=5.7 Hz, 2H), 2.23 (dq, J=20.9, 7.5 Hz, 2H), 0.61 (t, J=7.4 Hz, 3H). M+H (m/z) 321

Example 56

4-[6-amino-4-ethyl-5-(4-hydroxyphenyl)-3-pyridyl]-N,N-dimethyl-benzamide 56

Following the procedures of Example 89, 56 was prepared. M+H (m/z) 362

Example 57

4-[2-amino-4-ethyl-5-(m-tolyl)-3-pyridyl]phenol 57

Following the procedures of Example 89, 57 was prepared. M+H (m/z) 305

Example 58

5-[6-amino-4-ethyl-5-(4-hydroxyphenyl)-3-pyridyl]-1H-pyridin-2-one 58

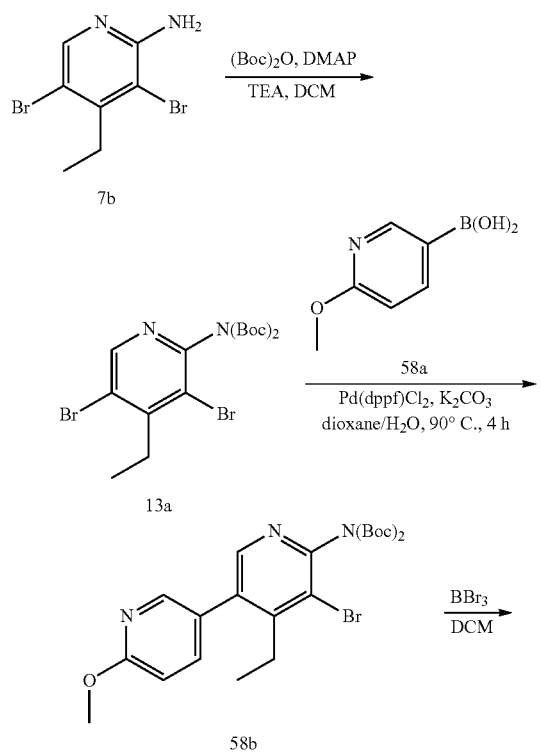
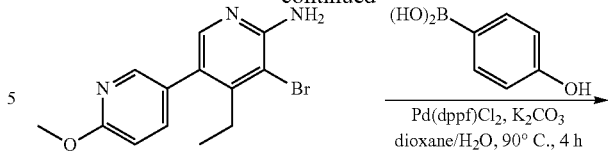
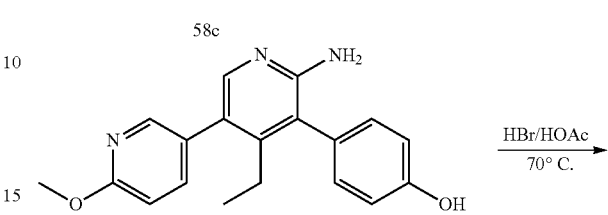

A solution of 3,5-dibromo-4-ethylpyridin-2-amine 7b (1.0 g, 3.57 mmol), Boc$_2$O (1.6 g, 7.14 mmol), DMAP (1.1 g, 8.93 mmol), TEA (1 g, 10.71 mmol) in DCM (30 mL) was stirred at r.t. for 5 h. The mixture was diluted with water and extracted in EtOAc (30 mL×3). The combined extracts were washed with brine, dried over Na$_2$SO$_4$, concentrated and purified by column (ETOAc/PE=1:50) to give 3,5-dibromo-4-ethylpyridin-2-(bis-tert-butyloxycarbonyl)amine 13a as solid (1.5 g, yield 63%). $^1$H NMR (400 MHz, Methanol-d4) δ 8.50 (s, 1H), 3.10-3.04 (m, 2H), 18 (s, 18H), 1.19 (t, 3H).

A solution of 13a (500 mg, 1.04 mmol), (6-methoxypyridin-3-yl)boronic acid 58a (185 mg, 1.25 mmol), Pd(dppf)Cl$_2$ (15 mg, 0.02 mmol), and K$_2$CO$_3$ (290 mg, 2.08 mmol) in dioxane/water (40 mL/8 mL) was stirred at 90° C. for 5 h under N$_2$. The mixture was cooled to r.t., extracted with EtOAc (30 mL×3), washed with brine (20 mL), dried over Na$_2$SO$_4$, and concentrated in vacuum to give crude product, which was purified by column (EtOAc/PE=1:10) to give 5-bromo-4-ethyl-6'-methoxy-[3,3'-bipyridin]-6-(bis-tert-butoxycarbonyl)amine 58b as solid (450 mg, yield 85%).

To a solution of 58b (400 mg, 0.79 mmol) in DCM (20 mL) was added BBr$_3$ (0.6 mL) dropwise at 0° C. The mixture was stirred at 15° C.-18° C. for 2 h. The mixture containing 5-bromo-4-ethyl-6'-methoxy-[3,3'-bipyridin]-6-amine 58c was concentrated and used in the next to step (400 mg, 100%).

A solution of 58c (250 mg, 0.81 mmol), (4-hydroxyphenyl)boronic acid (135 mg, 0.98 mmol), Pd(dppf)Cl$_2$ (12 mg, 0.02 mmol), and K$_2$CO$_3$ (225 mg, 1.62 mmol) in dioxane/water (20 mL/4 mL) was stirred at 90° C. for 5 h under N$_2$. The mixture was cooled to r.t. and extracted with EtOAc (30 mL×3), washed with brine (20 mL), dried over Na$_2$SO$_4$, concentrated and purified by column (EtOAc/PE=1:1) to give 4-(6-amino-4-ethyl-6'-methoxy-[3,3'-bipyridin]-5-yl) phenol 58d (100 mg, 42%).

A solution of 58d (100 mg, 0.31 mmol) in HBr/HOAc (5 mL) was stirred at 70° C. for 8 h. The reaction mixture was concentrated under reduced pressure and purified by pre- HPLC to give 58 (39.2 mg, yield: 41%). $^1$H NMR (400 MHz, Methanol-d4) δ 8.10-8.02 (m, 2H), 7.83 (s, 1H), 7.17 (d, J=8.8 Hz, 2H), 7.07-7.00 (m, 3H), 2.47-2.42 (m, 2H), 0.80 (t, 3H)

Example 59

4-[6-amino-4-ethyl-5-(3-methyl-1H-indazol-5-yl)-3-pyridyl]phenol 59

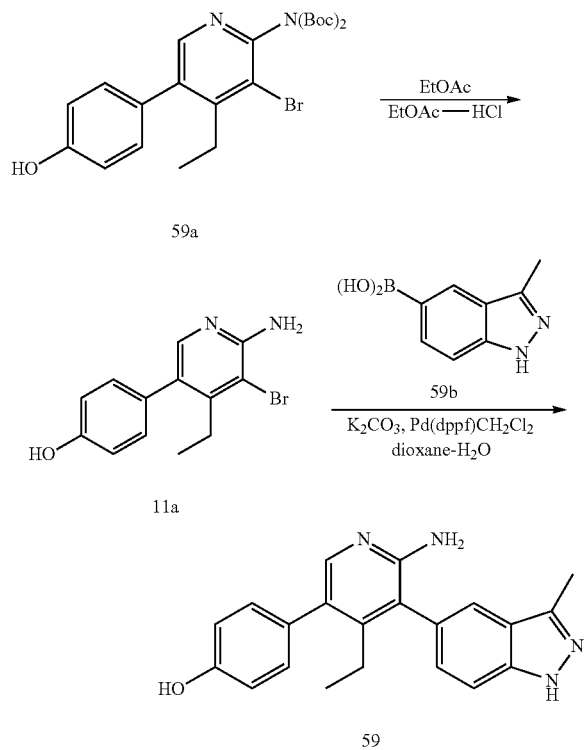

To the solution of 4-(6-bis(tert-butoxycarbonyl)amino-5-bromo-4-ethylpyridin-3-yl)phenol 59a (1.45 g, 2.94 mmol) in EtOAc (15 mL) was added HCl/EtOAc (15 mL), and the mixture was stirred at 25° C. for 3 h. Solvent was removed and water (10 mL) was added. The pH was adjusted to 9 with NaHCO$_3$, and extracted with EtOAc (15 mL×3), dried over Na$_2$SO$_4$, filtered and concentrated to give 4-(6-amino-5-bromo-4-ethylpyridin-3-yl)phenol 11a (1.02 g)

A microwave reaction tube containing 11a (80.0 mg, 0.272 mmol), (3-methyl-1H-indazol-5-yl)boronic acid 59b (48.0 mg, 0.27 mmol), K$_2$CO$_3$ (188 mg, 1.36 mmol), dioxane-H$_2$O (5:1, 2.5 mL) and Pd(dppf)Cl$_2$ (25.00 mg) was purged with nitrogen and heated under microwave irradiation at 120° C. for 50 min. It was cooled to 25° C., added water (5 mL) was added. It was extracted with EtOAc (15 mL×3), dried over Na$_2$SO$_4$. It was concentrated and purified by pre-HPLC to 59 (42.5 mg, yield: 45%) as white solid. LCMS: (5-95, AB, 1.5 min), 0.713 min, MS=344.9 [M+1]. $^1$H NMR (400 MHz, CD$_3$OD) δ 8.30 (br, 1H), 7.69 (s, 2H), 7.66-7.64 (d, J=8.0 Hz, 1H), 7.30-7.27 (m, 1H), 7.18-7.16 (d, J=8.0 Hz, 2H), 6.87-6.86 (d, J=8.0 Hz, 2H), 2.59 (s, 3H), 2.46-2.37 (m, 2H), 0.73-0.69 (t, J=7.6 Hz, 3H)

Example 60

[4-[6-amino-4-ethyl-5-(4-hydroxyphenyl)-3-pyridyl]phenyl]-morpholino-methanone 60

Following the procedures of Example 89, 60 was prepared. $^1$H NMR (400 MHz, DMSO-d$_6$) δ 9.50 (s, 1H), 7.72 (s, 1H), 7.45 (d, J=8.3 Hz, 2H), 7.42-7.31 (m, 2H), 7.12-7.02 (m, 2H), 6.93-6.85 (m, 2H), 5.03 (s, 2H), 3.62 (s, 4H), 2.27 (q, J=7.5 Hz, 2H), 0.63 (t, J=7.4 Hz, 3H). M+H (m/z) 404

Example 61

4-[2-amino-5-(3-benzyloxyphenyl)-4-ethyl-3-pyridyl]phenol 61

Following the procedures of Example 89, 61 was prepared. $^1$H NMR (400 MHz, DMSO-d$_6$) δ 9.50 (s, 1H), 7.69 (s, 1H), 7.52-7.37 (m, 4H), 7.41-7.27 (m, 4H), 7.10-6.93 (m, 3H), 6.95-6.84 (m, 4H), 5.14 (s, 2H), 4.96 (s, 2H), 2.24 (q, J=7.4 Hz, 2H), 0.59 (t, J=7.4 Hz, 3H). M+H (m/z) 397

Example 62

5-[6-amino-4-ethyl-5-(4-hydroxyphenyl)-3-pyridyl]pyridine-2-carbonitrile 62

Following the procedures of Example 89, 62 was prepared. $^1$H NMR (400 MHz, DMSO-d$_6$) δ 9.56 (s, 1H), 8.75 (dd, J=2.1, 1.1 Hz, 1H), 8.14-8.02 (m, 2H), 7.79 (s, 1H), 7.13-7.01 (m, 2H), 6.94-6.86 (m, 2H), 5.26 (s, 2H), 2.26 (q, J=7.5 Hz, 2H), 0.61 (t, J=7.4 Hz, 3H). M+H (m/z) 317

Example 63

5-[6-amino-4-ethyl-5-(4-hydroxyphenyl)-3-pyridyl]pyridine-3-carbonitrile 63

Following the procedures of Example 89, 63 was prepared. $^1$H NMR (400 MHz, DMSO-d$_6$) δ 9.56 (s, 1H), 8.84 (d, J=2.2 Hz, 1H), 8.35 (t, J=2.1 Hz, 1H), 7.78 (s, 1H), 7.11-6.95 (m, 2H), 6.94-6.83 (m, 2H), 5.22 (s, 2H), 2.22 (dq, J=15.3, 7.5 Hz, 2H), 0.61 (t, J=7.5 Hz, 3H). M+H (m/z) 317

Example 64

[3-[6-amino-4-ethyl-5-(4-hydroxyphenyl)-3-pyridyl]phenyl]-pyrrolidin-1-yl-methanone 64

Following the procedures of Example 89, 64 was prepared. M+H (m/z) 388

Example 65

4-[6-amino-4-ethyl-5-(4-hydroxyphenyl)-3-pyridyl]-N-cyclopropyl-benzamide 65

Following the procedures of Example 89, 65 was prepared. M+H (m/z) 374

Example 66

2-[3-[6-amino-4-ethyl-5-(4-hydroxyphenyl)-3-pyridyl]phenyl]acetonitrile 66

Following the procedures of Example 89, 66 was prepared. M+H (m/z) 330

Example 67

4-[6-amino-4-ethyl-5-(4-hydroxyphenyl)-3-pyridyl]-2-fluoro-benzonitrile 67

Following the procedures of Example 89, 67 was prepared. $^1$H NMR (400 MHz, DMSO-$d_6$) δ 9.55 (s, 1H), 7.99-7.91 (m, 1H), 7.76 (s, 1H), 7.55 (dd, J=10.6, 1.5 Hz, 1H), 7.40 (dd, J=8.0, 1.5 Hz, 1H), 7.10-7.00 (m, 2H), 6.93-6.85 (m, 2H), 5.21 (s, 2H), 3.27 (s, 2H), 2.29 (q, J=7.7 Hz, 2H), 0.62 (t, J=7.5 Hz, 3H). M+H (m/z) 334

Example 68

4-[2-amino-4-ethyl-5-(6-methoxy-3-pyridyl)-3-pyridyl]phenol 68

Following the procedures of Example 89, 68 was prepared. $^1$H NMR (400 MHz, DMSO-$d_6$) δ 9.53 (s, 1H), 8.10 (d, J=1.8 Hz, 1H), 7.73-7.64 (m, 2H), 7.08-7.01 (m, 2H), 6.95-6.76 (m, 2H), 5.02 (s, 2H), 3.88 (s, 3H), 2.22 (q, J=7.5 Hz, 2H), 0.63 (t, J=7.5 Hz, 3H). M+H (m/z) 322

Example 69

3-[6-amino-4-ethyl-5-(4-hydroxyphenyl)-3-pyridyl]-N-isopropyl-benzamide 69

Following the procedures of Example 89, 69 was prepared. $^1$H NMR (400 MHz, DMSO-$d_6$) δ 9.53 (s, 1H), 8.23 (d, J=7.8 Hz, 1H), 7.86-7.77 (m, 2H), 7.74 (s, 1H), 7.53-7.42 (m, 2H), 7.09-7.02 (m, 2H), 6.93-6.86 (m, 2H), 5.02 (s, 2H), 4.18-4.04 (m, 1H), 2.25 (q, J=7.4 Hz, 2H), 1.17 (d, J=6.6 Hz, 6H), 0.62 (t, J=7.5 Hz, 3H). M+H (m/z) 376

Example 70

N-[[4-[6-amino-4-ethyl-5-(4-hydroxyphenyl)-3-pyridyl]phenyl]methyl]methanesulfonamide 70

Following the procedures of Example 89, 70 was prepared. $^1$H NMR (400 MHz, DMSO-$d_6$) δ 9.52 (s, 1H), 7.68 (s, 1H), 7.56 (s, 2H), 7.47-7.35 (m, 3H), 7.09-7.02 (m, 2H), 6.92-6.85 (m, 2H), 4.97 (s, 2H), 4.20 (d, J=5.8 Hz, 2H), 2.88 (d, J=3.1 Hz, 3H), 2.25 (q, J=7.4 Hz, 2H), 0.61 (t, J=7.5 Hz, 3H). M+H (m/z) 398

Example 71

4-[2-amino-4-ethyl-5-(1-isobutylpyrazol-4-yl)-3-pyridyl]phenol 71

Following the procedures of Example 89, 71 was prepared. $^1$H NMR (400 MHz, DMSO-$d_6$) δ 9.51 (s, 1H), 7.82-7.74 (m, 2H), 7.08-6.96 (m, 2H), 6.92-6.84 (m, 2H), 4.88 (s, 2H), 3.93 (d, J=7.2 Hz, 2H), 2.13 (hept, J=6.9 Hz, 1H), 0.84 (d, J=6.7 Hz, 6H), 0.74 (t, J=7.4 Hz, 3H). M+H (m/z) 337

Example 72

5-[2-amino-4-ethyl-5-(4-hydroxyphenyl)-3-pyridyl]-2-hydroxy-benzonitrile 72

Following the procedure of Example 16, 72 was prepared. 1H NMR (400 MHz, DMSO-d6) δ 11.11 (s, 1H), 9.39 (s, 1H), 7.68 (s, 1H), 7.46 (d, J=2.2 Hz, 1H), 7.35 (dd, J=8.5, 2.2 Hz, 1H), 7.15-7.04 (m, 2H), 6.84-6.75 (m, 2H), 5.11 (s, 2H), 2.21 (q, J=7.4 Hz, 2H), 0.62 (t, J=7.4 Hz, 3H). M+H (m/z) 332

Example 73

4-[2-amino-4-ethyl-5-(2-methyl-4-pyridyl)-3-pyridyl]phenol 73

Following the procedures of Example 89, 73 was prepared. $^1$H NMR (400 MHz, DMSO-$d_6$) δ 9.54 (s, 1H), 8.45 (d, J=5.0 Hz, 1H), 7.72 (s, 1H), 7.25-7.19 (m, 1H), 7.15 (dd, J=5.0, 1.8 Hz, 1H), 7.12-7.01 (m, 2H), 6.93-6.83 (m, 2H), 5.12 (s, 2H), 3.27 (s, 3H), 2.28 (q, J=7.5 Hz, 2H), 0.63 (t, J=7.5 Hz, 3H). M+H (m/z) 306

Example 74

4-[2-amino-5-[3-(difluoromethyl)phenyl]-4-ethyl-3-pyridyl]phenol 74

Following the procedures of Example 89, 74 was prepared. $^1$H NMR (400 MHz, DMSO-$d_6$) δ 9.53 (s, 1H), 7.72 (s, 1H), 7.68-7.52 (m, 2H), 7.50 (dd, J=4.6, 3.1 Hz, 2H), 7.14-7.02 (m, 3H), 6.95-6.85 (m, 2H), 5.04 (s, 2H), 2.24 (q, J=7.4 Hz, 2H), 0.61 (t, J=7.4 Hz, 3H). M+H (m/z) 341

Example 75

N-[5-[6-amino-4-ethyl-5-(4-hydroxyphenyl)-3-pyridyl]-2-pyridyl]acetamide 75

Following the procedures of Example 89, 75 was prepared. $^1$H NMR (400 MHz, DMSO-$d_6$) δ 10.50 (s, 1H), 9.51 (d, J=15.1 Hz, 1H), 8.23 (dd, J=2.5, 0.9 Hz, 1H), 8.10 (d, J=8.5 Hz, 1H), 7.78-7.68 (m, 1H), 7.13-7.01 (m, 2H), 6.93-6.74 (m, 2H), 5.05 (s, 2H), 2.22 (dq, J=15.1, 7.4 Hz, 2H), 2.11 (s, 3H), 0.63 (t, J=7.5 Hz, 3H). M+H (m/z) 349

Example 76

4-[2-amino-5-(3,5-difluorophenyl)-4-ethyl-3-pyridyl]phenol 76

Following the procedures of Example 89, 76 was prepared. $^1$H NMR (400 MHz, DMSO-$d_6$) δ 9.55 (s, 1H), 7.74 (s, 1H), 7.21 (tt, J=9.4, 2.4 Hz, 1H), 7.13-7.00 (m, 4H), 6.93-6.85 (m, 2H), 5.11 (s, 2H), 2.28 (q, J=7.5 Hz, 2H), 0.63 (t, J=7.5 Hz, 3H). M+H (m/z) 327

Example 77

4-[2-amino-5-(3-chlorophenyl)-4-ethyl-3-pyridyl]phenol 77

Following the procedures of Example 89, 77 was prepared. $^1$H NMR (400 MHz, DMSO-$d_6$) δ 9.53 (s, 1H), 7.72 (s, 1H), 7.51-7.33 (m, 3H), 7.29 (dt, J=7.1, 1.6 Hz, 1H), 7.13-7.01 (m, 2H), 6.93-6.85 (m, 2H), 5.09 (s, 2H), 2.25 (q, J=7.5 Hz, 2H), 0.62 (t, J=7.5 Hz, 3H). M+H (m/z) 326

Example 78

4-[2-amino-5-(2-chlorophenyl)-4-ethyl-3-pyridyl]phenol 78

Following the procedures of Example 89, 78 was prepared. $^1$H NMR (400 MHz, DMSO-$d_6$) δ 9.56 (s, 1H), 7.62

(s, 1H), 7.60-7.51 (m, 1H), 7.45-7.33 (m, 3H), 7.10-7.00 (m, 2H), 6.93-6.85 (m, 2H), 5.05 (s, 2H), 2.10-1.95 (m, 2H), 0.58 (t, J=7.5 Hz, 3H). M+H (m/z) 326

Example 79

4-[2-amino-4-ethyl-5-(4-fluoro-3-methyl-phenyl)-3-pyridyl]phenol 79

Following the procedures of Example 89, 79 was prepared. $^1$H NMR (400 MHz, DMSO-d$_6$) δ 9.52 (s, 1H), 8.13 (s, 1H), 7.68 (s, 1H), 7.22 (dd, J=7.7, 1.9 Hz, 1H), 7.21-7.11 (m, 2H), 7.15-7.00 (m, 2H), 6.93-6.84 (m, 2H), 4.97 (s, 2H), 2.31-2.18 (m, 5H), 0.62 (t, J=7.5 Hz, 3H). M+H (m/z) 323

Example 80

4-[2-amino-5-(4-chlorophenyl)-4-ethyl-3-pyridyl]phenol 80

Following the procedures of Example 89, 80 was prepared. $^1$H NMR (400 MHz, DMSO-d$_6$) δ 9.53 (s, 1H), 8.15 (s, 1H), 7.70 (s, 1H), 7.51-7.42 (m, 2H), 7.13-7.01 (m, 2H), 6.93-6.84 (m, 2H), 5.02 (s, 2H), 2.24 (q, J=7.4 Hz, 2H), 0.61 (t, J=7.5 Hz, 3H). M+H (m/z) 326

Example 81

4-[6-amino-4-ethyl-5-(4-hydroxyphenyl)-3-pyridyl]-N-methyl-benzamide 81

Following the procedures of Example 89, 81 was prepared. M+H (m/z) 348

Example 82

4-[2-amino-4-ethyl-5-[3-(morpholinomethyl)phenyl]-3-pyridyl]phenol 82

Following the procedures of Example 89, 82 was prepared. $^1$H NMR (400 MHz, DMSO-d$_6$) δ 9.51 (s, 1H), 7.70 (s, 1H), 7.37 (t, J=7.5 Hz, 1H), 7.30-7.13 (m, 3H), 7.09-7.02 (m, 2H), 6.88 (d, J=8.5 Hz, 2H), 4.96 (s, 2H), 3.60-3.48 (m, 6H), 2.36 (s, 3H), 2.36 (d, J=9.5 Hz, 1H), 2.24 (q, J=7.4 Hz, 2H), 0.61 (t, J=7.5 Hz, 3H). M+H (m/z) 390

Example 83

4-[2-amino-4-ethyl-5-(2-methoxypyrimidin-5-yl)-3-pyridyl]phenol 83

Following the procedures of Example 89, 83 was prepared. M+H (m/z) 323

Example 84

4-[2-amino-4-ethyl-5-(1H-indazol-6-yl)-3-pyridyl]phenol 84

Following the procedures of Example 89, 84 was prepared. M+H (m/z) 331

Example 85

4-[2-amino-4-ethyl-5-(2-methylindazol-4-yl)-3-pyridyl]phenol 85

Following the procedures of Example 89, 85 was prepared. $^1$H NMR (400 MHz, DMSO-d$_6$) δ 9.52 (s, 1H), 8.10

(d, J=16.8 Hz, 1H), 7.81-7.73 (m, 2H), 7.55 (d, J=8.7 Hz, 1H), 7.43-7.23 (m, 3H), 7.14-7.02 (m, 2H), 6.93-6.86 (m, 2H), 5.01 (d, J=14.3 Hz, 2H), 4.15 (d, J=15.6 Hz, 3H), 2.32-2.17 (m, 2H), 0.54 (t, J=7.5 Hz, 3H). M+H (m/z) 345

Example 86

4-[2-amino-4-ethyl-5-(2-methyl-1H-benzimidazol-5-yl)-3-pyridyl]phenol 86

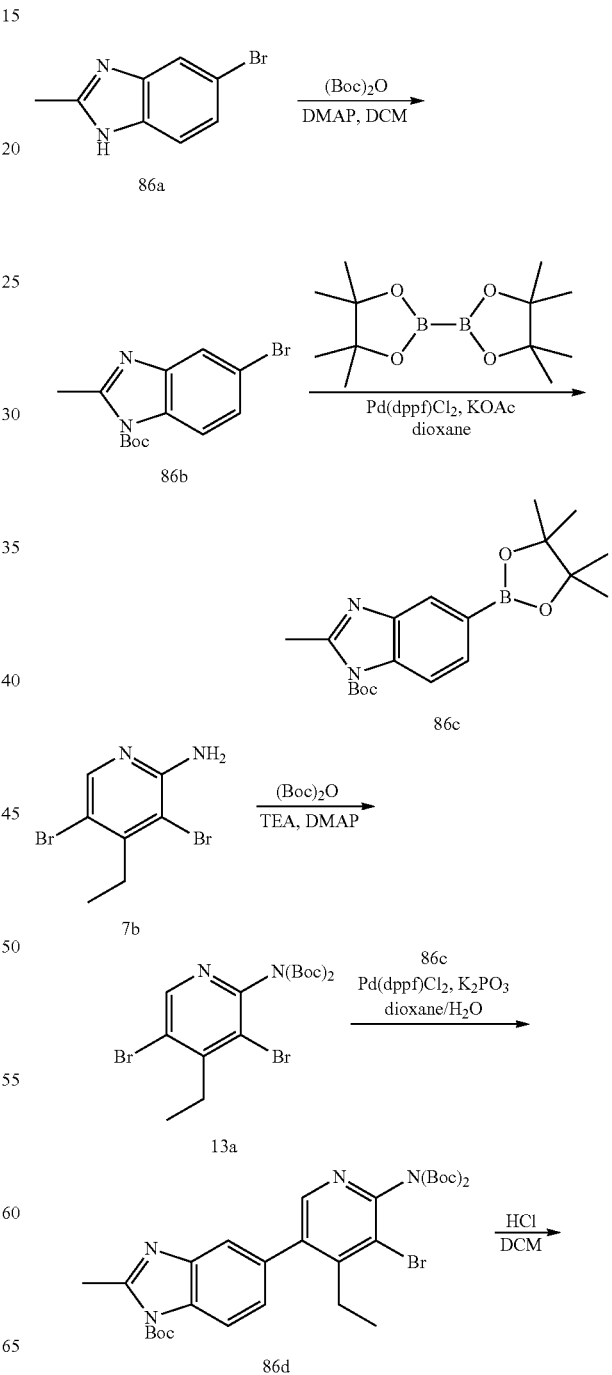

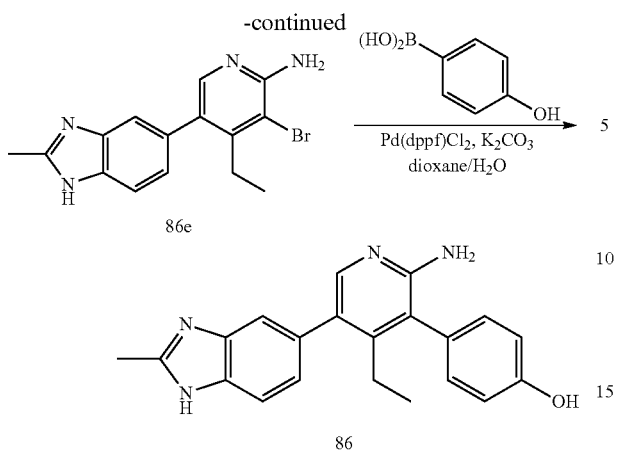

A solution of 5-bromo-2-methyl-1H-benzo[d]imidazole 86a (200 mg, 0.95 mmol), Boc₂O (415 mg, 1.90 mmol), DMAP (232 mg, 1.90 mmol) in DCM (20 mL) was stirred at r.t. for 5 h. The mixture was diluted with water and extracted in DCM (20 mL×2). The combined extracts were washed with brine, dried over Na₂SO₄, concentrated, and purified by column (EtOAc/PE=1:20) to give tert-butyl 5-bromo-2-methyl-1H-benzo[d]imidazole-1-carboxylate 86b as solid (300 mg, yield 97%).

A mixture of 86b (300 mg, 0.97 mmol), 4,4,4',4',5,5,5',5'-octamethyl-2,2'-bi(1,3,2-dioxaborolane) (465 mg, 1.94 mmol), Pd(dppf)Cl₂ (68 mg, 0.1 mmol), and KOAc (190 mg, 1.94 mmol) in dioxane (20 mL) was purged and stirred at 90° C. for 5 h under N₂. The mixture was cooled to r.t., extracted with EtOAc (20 mL×2), washed with brine (20 mL), dry over Na₂SO₄, concentrated, and purified by column (EtOAc/PE=1:8) to give tert-butyl 2-methyl-5-(4,4,5,5-tetramethyl-1,3,2-dioxaborolan-2-yl)-1H-benzo[d]imidazole-1-carboxylate 86c as solid (200 mg, yield 62%).

A solution of 3,5-dibromo-4-ethylpyridin-2-amine 7b (320 mg, 1.14 mmol), (Boc)₂O (500 mg, 2.29 mmol), DMAP (286 mg, 2.86 mmol), TEA (420 mg, 3.43 mmol) in DCM (30 mL) was stirred at r.t. for 5 h. The mixture was diluted with water and extracted in EtOAc (20 mL×3). The combined extracts were washed with brine, dried over Na₂SO₄, concentrated and purified by column (EtOAc/PE=1:40) to give 3,5-dibromo-4-ethylpyridin-2-(bis-tert-butyloxycarbonyl)amine 13a as a solid (580 mg, yield 100%).

A mixture of 13a (140 mg, 0.29 mmol), 86c (125 mg, 0.35 mmol), Pd(dppf)Cl₂ (5 mg, 0.006 mmol), and K₂CO₃ (85 mg, 0.58 mmol) in dioxane/water (15 mL/3 mL) was purged and stirred at 90° C. for 5 h under N₂. The mixture was cooled to r.t. and extracted with EtOAc (15 mL×3), washed with brine (15 mL), dried over Na₂SO₄, concentrated to give crude 3-bromo-4-ethyl-5-(2-methyl-1H-(tert-butoxycarbonyl)benzo[d]imidazol-5-yl)pyridin-2-(bis-tert-butoxycarbonyl)amine 86d (120 mg, yield 65%) which was used to next step.

To a stirred solution of 86d (120 mg, 0.19 mmol) in DCM (20 mL) was added HCl-EtOAc (3 mL) at 0° C. After the reaction mixture was stirred at r.t. for 3 h, it was concentrated and purified by column (EtOAc/PE=1:10) to give 3-bromo-4-ethyl-5-(2-methyl-1H-benzo[d]imidazol-5-yl)pyridin-2-amine 86e as solid (60 mg, yield 85%).

A mixture of 86e (60 mg, 0.18 mmol), (4-hydroxyphenyl)boronic acid (30 mg, 0.22 mmol), Pd(dppf)Cl₂ (2 mg, 0.004 mmol), and K₂CO₃ (50 mg, 0.26 mmol) in dioxane/water (10 mL/2 mL) was purged and stirred at 90° C. for 5 h under N₂. The mixture was cooled to r.t. and extracted with EtOAc (10 mL×3). It was washed with brine (10 mL), dried over Na₂SO₄, concentrated and purified by pre-HPLC to give 86 (14.1 mg, yield: 23%). LCMS: (5-95, AB, 1.5 min), 0.628 min, MS=344.9 [M+1]. ¹H NMR (400 MHz, Methanol-d4) δ 7.87-7.79 (m, 3H), 7.61 (d, J=8.4 Hz, 1H), 7.19 (d, J=8.4 Hz, 2H), 7.01 (d, J=8.4 Hz, 2H), 2.87 (s, 3H), 2.49-2.43 (m, 2H), 0.700 (t, J=7.6 Hz, 3H)

Example 87

4-[6-amino-4-ethyl-5-(1H-indazol-5-yl)-3-pyridyl]phenol 87

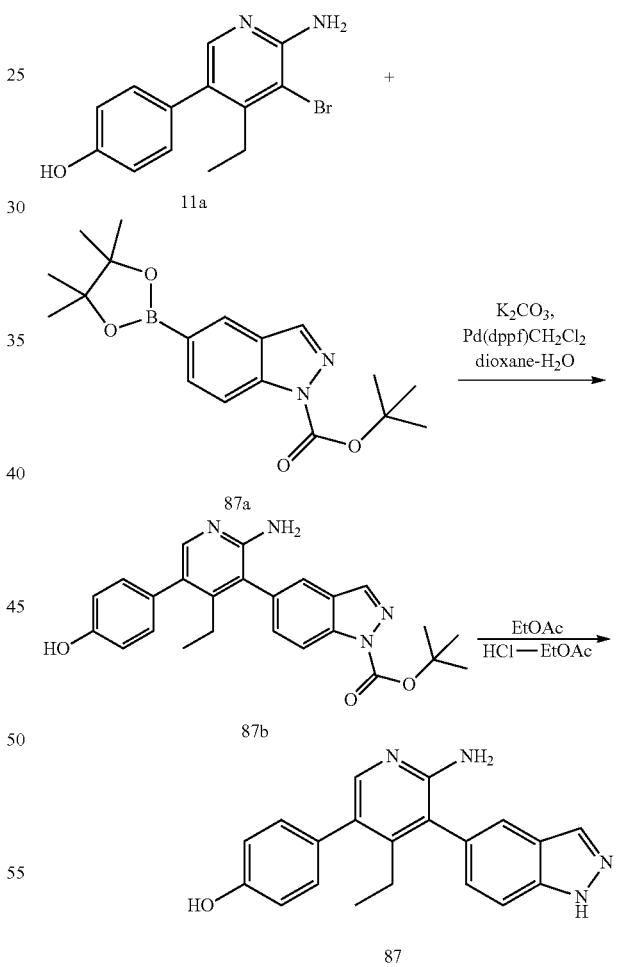

To a solution of 4-(6-bis(tert-butoxycarbonyl)amino-5-bromo-4-ethylpyridin-3-yl)phenol 59a (1.45 g, 2.94 mmol) in EtOAc (15 mL) was added HCl/EtOAc (15 mL). The reaction mixture was stirred at 25° C. for 3 h. It was concentrated and water (10 mL). pH was adjusted to 9 with NaHCO₃. It was extracted with EtOAc (3×20 mL), dried over $Na_2SO_4$, and concentrated to give crude 4-(6-amino-5-bromo-4-ethylpyridin-3-yl)phenol 11a.

A microwave tube containing 11a (80 mg, 0.273 mmol), tert-butyl 5-(4,4,5,5-tetramethyl-1,3,2-dioxaborolan-2-yl)-1H-indazole-1-carboxylate 87a (94 mg, 0.273 mmol), $K_2CO_3$ (189 mg, 1.36 mmol), dioxane-$H_2O$ (5:1, 2.3 mL) and Pd(dppf)$Cl_2$ (25.00 mg) was purged with $N_2$ and heated under the microwave irradiation at 120° C. for 45 min. The mixture was cooled to 25° C. and water (15 mL) was added. It was extracted it with EtOAc (20 mL×3), dried over $Na_2SO_4$, and concentrated to give tert-butyl 5-(2-amino-4-ethyl-5-(4-hydroxyphenyl)pyridin-3-yl)-1H-indazole-1-carboxylate 87b (155 mg) as brown solid. LCMS: (5-95, AB, 1.5 min), 0.695 min, MS=330.9 [M−100]; 0.786 min, MS=431.0 [M+1].

To the mixture of 87b (100 mg, 0.239 mmol) in EtOAc (5 mL) was added HCl/EtOAc (7 mL) and the reaction mixture was stirred at 25° C. for 2 h. Solvent was removed and it was purified by prep-HPLC to give 87 (20 mg, yield: 26.1%) as white solid. LCMS: (5-95, AB, 1.5 min), 0.702 min, MS=330.9 [M+1]. $^1$H NMR (400 MHz, $CD_3OD$) δ 8.28 (s, 1H), 8.13 (s, 1H), 7.76-7.72 (m, 2H), 7.69 (s, 1H), 7.32-7.29 (d, J=12.0 Hz, 1H), 7.18-7.16 (m, 2H), 6.87-6.85 (d, J=8.8 Hz, 2H), 2.46-2.35 (m, 2H), 0.73-0.69 (t, J=7.6 Hz, 3H).

Example 88

4-[2-amino-4-ethyl-5-(1H-indazol-5-yl)-3-pyridyl]phenol 88

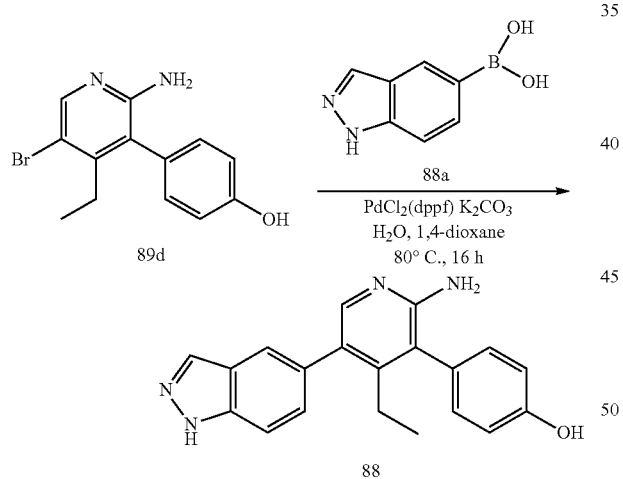

Into a 250-mL 3-necked round-bottom flask purged and maintained with an inert atmosphere of nitrogen was placed 4-(2-amino-5-bromo-4-ethylpyridin-3-yl)phenol 89d (1.0 g, 3.41 mmol, 1.00 equiv), (2H-indazol-6-yl)boronic acid 88a (663 mg, 4.09 mmol, 1.20 equiv), $K_2CO_3$ (3.3 g, 23.70 mmol, 6.95 equiv), water (25 mL), 1,4-dioxane (25 mL), and Pd(dppf)$Cl_2$ (0.2 g, 0.1 eq). The resulting solution was stirred at 80° C. for 8 h and then extracted with 3×30 mL of ethyl acetate. The organic layers were combined and concentrated under vacuum. The residue was purified on a silica gel column eluting with DCM/$CH_3OH$ (20/1-10/1). The crude product was re-crystallized from EtOH/$H_2O$ in the ratio of 1:1 to afford 251 mg (22%) of 88 as a white solid. LC-MS: (ES, m/z): 331 [M+H]$^+$. H-NMR: (300 MHz, DMSO, ppm): δ 13.05 (s, 1H), 9.56 (s, 1H), 8.09 (s, 1H), 7.76-7.79 (m, 2H), 7.41 (s, 1H), 7.04-7.09 (m, 3H), 6.88-6.91 (d, J=8.7 Hz, 2H), 5.12 (s, 2H), 2.27-2.30 (q, 2H), 0.59-0.64 (t, 3H)

Example 89

4-[2-amino-4-ethyl-5-(2-methylindazol-6-yl)-3-pyridyl]phenol 89

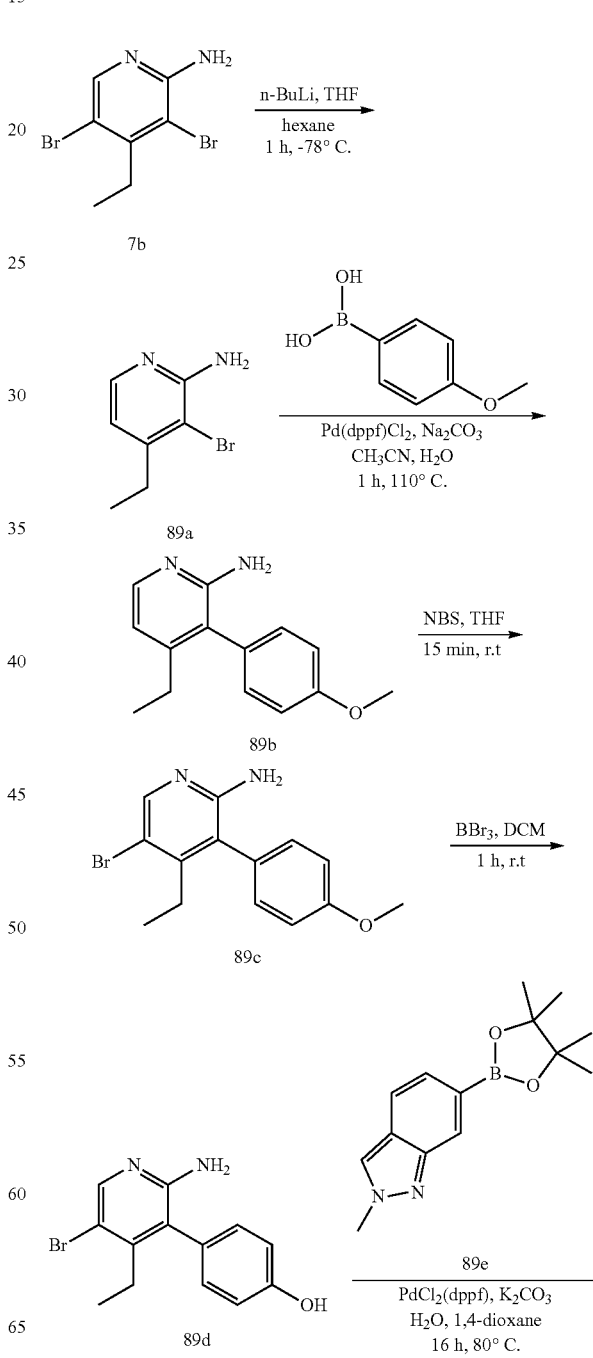

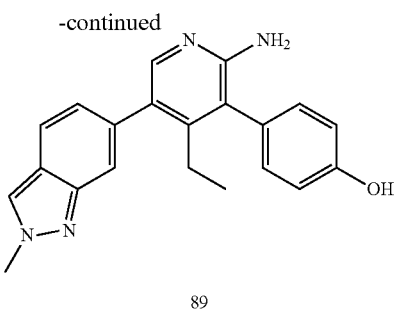

89

Into a 500-mL 3-necked round-bottom flask purged and maintained with an inert atmosphere of nitrogen was placed 4-ethylpyridin-2-amine 7a (10 g, 81.85 mmol, 1.00 equiv), tetrahydrofuran (200 mL), and NBS (29 g, 162.94 mmol, 2.00 equiv) at 0° C. The resulting solution was stirred at room temperature for 15 min and then concentrated under vacuum. The residue was purified on a silica gel column eluting with DCM/MeOH (100:1-20:1) to afford 18 g (79%) of 3,5-dibromo-4-ethylpyridin-2-amine 7b as a white solid.

Into a 500-mL 3-necked round-bottom flask purged and maintained with an inert atmosphere of nitrogen was placed 7b (18 g, 64.29 mmol, 1.00 equiv) in tetrahydrofuran (360 mL). To this was added a solution of n-BuLi (in hexane) (58 mL, 2.00 equiv, 2.2 mol/L) at −78° C. The resulting solution was stirred at −78° C. for 1 h, quenched by the addition of 450 mL of NH$_4$Cl and then extracted with 2×500 mL of ethyl acetate. The combined organic layers were washed with 2×500 mL of brine, dried over anhydrous sodium sulfate and concentrated under vacuum. The crude product was purified by Flash-Prep-HPLC to afford 12 g (93%) of 3-bromo-4-ethylpyridin-2-amine 89a as a white solid.

Into a 500-mL 3-necked round-bottom flask purged and maintained with an inert atmosphere of nitrogen was placed a solution of 89a (12 g, 59.68 mmol, 1.00 equiv) in CH$_3$CN (100 mL), (4-methoxyphenyl)boronic acid (11 g, 72.39 mmol, 1.20 equiv), Na$_2$CO$_3$ (120 mL, sat.), and Pd(dppf)Cl$_2$ (1.2 g, 1.64 mmol, 0.03 equiv). The resulting solution was stirred at 110° C. for 1 h, diluted with of 500 mL of EA and then extracted with of 2×500 mL of ethyl acetate. The combined organic layers were washed with 3×200 mL of brine, dried over anhydrous sodium sulfate and concentrated under vacuum. The residue was purified on a silica gel column eluting with ethyl acetate/petroleum ether (1:100-1:10) to afford 10 g (73%) of 4-ethyl-3-(4-methoxyphenyl)pyridin-2-amine 89b as a white solid.

Into a 250-mL 3-necked round-bottom flask purged and maintained with an inert atmosphere of nitrogen was placed 89b (10 g, 43.80 mmol, 1.00 equiv), tetrahydrofuran (100 mL), followed by NBS (7.8 g, 43.83 mmol, 1.00 equiv) at 0° C. The resulting solution was stirred at room temperature for 15 min, diluted with 500 mL of EtOAc and 500 mL of H$_2$O. The resulting solution was extracted with 2×500 mL of ethyl acetate. The organic layers were combined, washed with 2×500 mL of brine and concentrated under vacuum. The residue was purified on a silica gel column eluting with ethyl acetate/petroleum ether (1:20-1:10) to afford 8 g (59%) of 5-bromo-4-ethyl-3-(4-methoxyphenyl)pyridin-2-amine 89c as a white solid.

Into a 250-mL 3-necked round-bottom flask purged and maintained with an inert atmosphere of nitrogen was placed 89c (8 g, 26.04 mmol, 1.00 equiv), dichloromethane (100 mL), followed by tribromoborane (19.6 g, 78.24 mmol, 3.00 equiv) at 0° C. The resulting solution was stirred at room temperature for 1 h and then quenched by the addition of 100 mL of NaHCO$_3$ (1M) at 0° C. The solids were collected by filtration and then washed with 1×100 mL of H$_2$O and 1×300 mL of EA/PE (1:1) to afford 6.3 g (83%) of 4-(2-amino-5-bromo-4-ethylpyridin-3-yl)phenol 89d as a white solid.

Into a 250-mL 3-necked round-bottom flask purged and maintained with an inert atmosphere of nitrogen was placed 89d (1.0 g, 3.41 mmol, 1.00 equiv), 2-methyl-6-(tetramethyl-1,3,2-dioxaborolan-2-yl)-2H-indazole 89e (880 mg, 3.41 mmol, 1.00 equiv), potassium carbonate (3.3 g, 23.88 mmol, 7.00 equiv), water (30 mL), 1,4-dioxane (25 mL), and Pd(dppf)Cl$_2$ (200 mg, 0.3 mmol, 0.1 equiv). The resulting solution was stirred at 80° C. for 16 h, diluted with 500 mL of H$_2$O and 500 mL of ethyl acetate. The organic layer was washed with 2×250 mL of brine and concentrated under vacuum. The residue was purified on a silica gel column eluting with DCM/CH$_3$OH (20:1-10:1). The crude product was re-crystallized from MeOH/H$_2$O in the ratio of 1:1 to afford 327 mg (28%) of 89 as a white solid. LC-MS: (ES, m/z): 345 [M+H]$^+$. H-NMR: (300 MHz, DMSO, ppm): δ 9.54 (s, 1H), 8.34 (s, 1H), 7.76 (s, 1H), 7.68-7.71 (d, J=9.0 Hz, 1H), 7.44-7.45 (d, J=0.9 Hz, 1H), 7.06-7.09 (d, J=8.4 Hz, 2H), 6.95-6.99 (m, 1H), 6.87-6.90 (d, J=8.4 Hz, 2H), 4.99 (s, 2H), 4.17 (s, 3H), 2.25-2.32 (m, 2H), 0.59-0.64 (m, 3H).

Example 90

4-[2-amino-5-(3-aminophenyl)-4-ethyl-3-pyridyl]phenol 90

Following the procedures of Example 89, 90 was prepared. $^1$H NMR (400 MHz, DMSO-d$_6$) δ 9.50 (s, 1H), 7.65 (s, 1H), 7.09-6.98 (m, 3H), 6.92-6.83 (m, 2H), 6.56-6.46 (m, 2H), 6.41 (dt, J=7.4, 1.3 Hz, 1H), 5.06 (s, 2H), 4.87 (d, J=6.4 Hz, 2H), 2.27 (q, J=7.4 Hz, 2H), 0.65 (t, J=7.4 Hz, 3H). M+H (m/z) 306

Example 91

4-[2-amino-5-(4-aminophenyl)-4-ethyl-3-pyridyl]phenol 91

Following the procedures of Example 89, 91 was prepared. M+H (m/z) 306

Example 92

5-[6-amino-4-ethyl-5-(4-hydroxyphenyl)-3-pyridyl]-N-methyl-pyridine-2-carboxamide 92

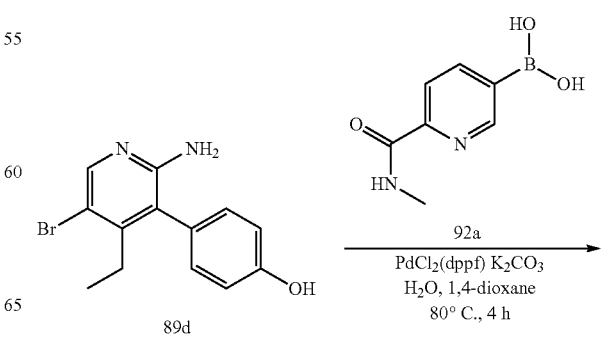

-continued

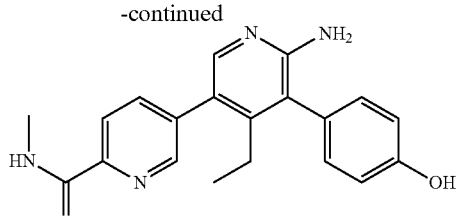

92

Into a 100-mL 3-necked round-bottom flask purged and maintained with an inert atmosphere of nitrogen was placed 4-(2-amino-5-bromo-4-ethylpyridin-3-yl)phenol 89d (800 mg, 2.73 mmol, 1.00 equiv), [6-(methylcarbamoyl)pyridin-3-yl]boronic acid 92a (540 mg, 3.00 mmol, 1.10 equiv), potassium carbonate (2.9 g, 20.83 mmol, 7.00 equiv), 1,4-dioxane (21 mL), water (21 mL), and Pd(dppf)Cl$_2$ (160 mg). The resulting solution was stirred at 80° C. for 16 h, cooled and extracted with 3×20 mL of ethyl acetate. The organic layers were combined and concentrated under vacuum. The residue was purified on a silica gel column eluting with DCM/CH$_3$OH (20/1-10/1). The crude product was re-crystallized from MeOH/H$_2$O in the ratio of 1:1 to afford 270 mg (28%) of 92 as an off-white solid. LC-MS: (ES, m/z): 349 [M+H]$^+$. H-NMR (300 MHz, DMSO, ppm): δ 9.56 (s, 1H), 8.78-8.81 (m, 1H), 8.58-8.59 (d, J 3.0 Hz, 1H), 8.04-8.07 (m, 1H), 7.94-7.98 (m, 1H), 7.78 (s, 1H), 7.04-7.07 (d, J 8.4 Hz, 2H), 6.87-6.90 (d, J 8.7 Hz, 2H), 5.20 (s, 2H), 2.83-2.84 (d, J 3.0 Hz, 3H), 2.22-2.29 (m, 2H), 0.58-0.63 (m, 3H)

Example 93

4-[6-amino-4-ethyl-5-(1H-indazol-6-yl)-3-pyridyl]phenol 93

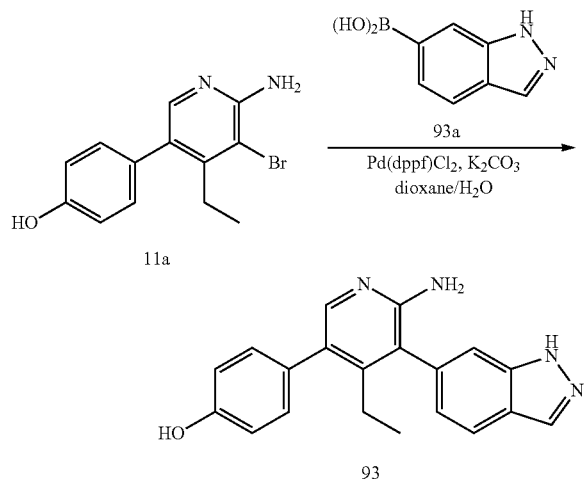

A solution of 4-(6-amino-5-bromo-4-ethylpyridin-3-yl)phenol 11a (60 mg, 0.20 mmol), (1H-indazol-6-yl)boronic acid 93a (40 mg, 0.24 mmol), Pd(dppf)Cl$_2$ (4 mg, 0.004 mmol), and K$_2$CO$_3$ (57 mg, 0.40 mmol) in dioxane/water (10 mL/2 mL) was purged with N$_2$ and stirred at 90° C. for 5 h under N$_2$. The mixture was cooled to r.t. and extracted with EtOAc (10 mL×3), washed brine (10 mL), dry over Na$_2$SO$_4$, concentrated, and purified by pre-HPLC to give 93 (5.8 mg, yield: 10%). $^1$H NMR (400 MHz, Methanol-d4) δ 8.24 (s, 1H), 8.03 (m, 1H), 7.70 (s, 1H), 7.13 (d, J=6.0 Hz, 1H), 7.23 (d, J=8.8 Hz, 2H), 6.91-6.87 (d, J=7.2 Hz, 1H), 6.91-6.87 (m, 2H), 2.47 (t, 2H), 0.77-0.70 (m, 3H).

Example 94

5-[6-amino-4-ethyl-5-(4-hydroxyphenyl)-3-pyridyl]-2-hydroxy-benzonitrile 94

Following the procedures of Example 89, 94 was prepared: M+H (m/z) 332

Example 95

5-[6-amino-4-ethyl-5-(4-hydroxyphenyl)-3-pyridyl]-2-hydroxy-benzamide 95

Following the procedures of Example 89, 95 was prepared: $^1$H NMR (400 MHz, DMSO-d$_6$) δ 13.04 (s, 1H), 9.52 (s, 1H), 8.38 (s, 1H), 7.89-7.78 (m, 2H), 7.71 (s, 1H), 7.35 (dd, J=8.4, 2.1 Hz, 1H), 7.09-6.99 (m, 2H), 6.95-6.85 (m, 3H), 4.96 (s, 2H), 2.24 (q, J=7.4 Hz, 2H), 0.62 (t, J=7.4 Hz, 3H). M+H (m/z) 350

Example 901

Ubiquitin-Rhodamine 110-Glycine Expression, Purification and Preparation

For the cloning of the ubiquitin-intein-His6 expression vector, the coding region for amino acids 1-75 of human ubiquitin were amplified by PCR with suitable primers for subsequent cloning into in the expression vector pTYB2. Ubiquitin-intein-His6 was expressed and purified as described (Hassiepen, U. et al (2007) Anal. Biochem. 371: 138-143) with the following exceptions. Ubiquitinintein was batch purified on nickel chelating affinity media (Amersham) and Ubiquitin-MES was released by addition of 100 mM Na-mercaptoethanesulfonate (MES) for 5 h at 22° C. Ubiquitin-MES was eluted with 4 column volumes of 20 mM 2-(N-morpholino)ethanesulfonic acid, pH 6.5, 100 mM NaCl. Eluted material was concentrated by ultrafiltration (Vivaspin 6, 5-kDa cutoff) to less than 5 ml and supplemented with 10 eq. N-hydroxysuccinimide (Fluka 56480), 10 eq. sym-collidine (Fluka 27690) and 15 eq. bisglycyl-rhodamine110 for 24 h at 37° C. For purification the reaction mixture was desalted into 20 mM 2-(N-morpholino) ethanesulfonic acid, pH 6.5 on a HiPrep Sephadex G-25 26/10 column (GE healthcare) then applied to a Source 15 S HR 10/10 column (GE healthcare) which was developed with a gradient of 0-1 NaCl. Final Ubiquitin-Rhodamine110-Gly fractions were pooled, dialysed into 50 mM Tris, pH 7.5 then concentrated to 1 mg per ml. Ub-Rho110-Gly is commercially available from Boston Biochem.

In the fluorescent assay, 0.5 mM Ubiquitin-Rhodamine110-Gly in 40 mM Tris-HCl buffer, pH 7.6, 5 mM DTT and 0.05 mg ml-1 BSA were incubated with 0.05-5 ng/ml of each DUB for 60 min at 30° C. Samples were prepared in triplicates and analyzed in 96-well plates using a Envision® 2104 multi label reader (Perkin Elmer) at Excitation/Emission 485/535 nm (Hassiepen, U. et al (2007) Anal. Biochem. 371:138-143; Ritorto, M. S., et al (2014) Nature Communications 5:4763; doi: 10.1038).

Example 902

Ub-Rho110 (USP7_Ub-Rho preInc (IC50) Mol and USP7_Ub-Rho110 Fluor (IC50) µmol)

Biochemical USP7 assays using Ubiquitin-Rho110 as a substrate: The final assay conditions were as follows: The Reaction Buffer consisted of: 50 mM Tris (pH 7.5), 0.01% (v/v) Triton X-100, 2.5 mM Dithiothreitol, 0.1% (w/v) bovine gamma globulin (Sigma cat #G5009-25G); USP7, full-length, native C-Terminus, 0.2 nM; the substrate, Ubiquitin-Rho110 (Boston Biochem cat #U-555), 1 uM. Reactions were carried out for 1 hour at room temperature, in black 20 µL volume polystyrene ProxiPlate 384 F Plus® (PerkinElmer cat #6008260).

Test compounds, including a control USP7 inhibitor (Ub-aldehyde, Boston Biochem cat #U-201) were serially diluted in DMSO, in 384 well clear V-bottom polypropylene plates (Greiner cat #781280). Compounds in DMSO were diluted 10-fold into Reaction Buffer, to achieve 3-fold the final desired concentration. The substrate, Ubiquitin-Rho110 (Boston Biochem cat #U-555), was prepared at 3 µM (3-fold the final concentration) and 5 ul was dispensed into the reaction plate. 5 ul of the compounds (diluted in Reaction Buffer at 3-fold the final concentration) were transferred to the reaction plate. 5 ul of 0.6 nM USP7 (diluted in Reaction Buffer at 3-fold the final concentration) was transferred to the reaction plate to initiate the reaction. After 1 hour incubation at room temperature the reaction was quenched by the addition of 5 ul of 400 mM acetic acid. The enzymatic product was measured by quantifying the fluorescence signal of cleaved Rhodamine-110 using excitation at 485 nm and emission at 535 nm. When pre-incubation of USP7 with compounds was required, the order of addition of reagents was modified to pre-mix the compounds with USP7 (with a 1 hour incubation period), prior to the addition of the substrate and the initiation of the reaction period. Percentage inhibition values were calculated relative to a no enzyme control and a uninhibited enzyme control. Curve fitting and IC50 calculations were carried out using Genedata Screener software.

The palm binding site (palm site) is a region defined by residues in the USP7 catalytic domain within 0.5 nm distance of the palm ligand. This encompasses residues V296, Q297, C300, R301, L304, D305, E308, I320, P321, F324, Y348, D349, H403, Q405 and M515.

Table 2 shows that chemical optimization of palm site fragment compounds enhances biochemical potency and retains USP7 selectivity. Measuring the inhibition of USP7 and the USP7 catalytic domain measures potency. Measuring the inhibition of USP47 and USP5 reflects selectivity. These data thus indicate that the USP7 antagonists Compounds 88, 45, and 81 are selective antagonists of USP7 catalytic activity, but the inactive control compounds 89 and 25 are ineffective in antagonizing the activity of any DUB evaluated.

TABLE 2

| | Ub-Rho110 IC$_{50}$ (µM) | | | |
|---|---|---|---|---|
| Compound No. | USP7 | USP7 cat | USP47 | USP5 |
| 88 | 0.98 | 0.43 | >200 | 18.63 |
| 89 | >63.3 | >200 | >200 | >200 |
| 45 | 2.9 | 1.3 | >200 | >200 |
| 81 | 1.4 | 0.53 | >200 | >200 |
| 25 | >63.3 | >63.3 | >200 | >200 |

Example 903

Activity-Based Enrichment of Deubiquitinases 293T cells at 80% confluency are harvested by rinsing the plate one time with 10 ml PBS followed by scraping. Cells are cleared by spinning them for 3 min at 350 g at 4° C. and the pellet is flash-frozen in liquid nitrogen and stored at −80° C. until lysis. Frozen cells are lysed by quickly re-thawing them in Buffer A (50 mM Tris-HCl pH 7.5, 250 mM Sucrose, 5 mM TCEP, 2 mM ATP, 50 µM phenylmethylsulfonyl fluoride (PMSF), 120 mM NaCl, 5 mM MgCl$_2$) and the lysate is cleared by centrifugation by spinning at 18,000 g at 4° C. The protein concentration is adjusted to 5 mg/ml and either 1.25 mg, 2.5 mg, or 5 mg of this cell lysate are incubated in duplicate with either 15 µM of compound 88 (a total of 2 separate USP7 antagonist-treated samples) or 15 µM of compound 89 (a total of 2 control compound-treated samples) in a Thermomixer (Eppendorf, Hauppage, N.Y.), 900 rpm, at 25° C., for 20 min. Subsequently, the 4 samples are all incubated with 6.6 µg/ml of either one of the following activity-based DUB probes (the same probe for each of the 4 samples): HA-tagged ubiquitin vinyl sulfone (Boston Biochem, Cambridge, Mass.), HA-tagged ubiquitin propargylamine (UbiQ Bio BV, Amsterdam, The Netherlands) or HA-tagged ubiquitin vinylmethyl ester (UbiQ Bio BV, Amsterdam, The Netherlands), 1200 rpm, at 25° C., for 1 hr. The reaction is terminated by adding a 20% SDS solution to a final concentration of 0.4% for at least 30 min at room temperature, rotating. Subsequently, the reacted lysate is diluted 10× with Buffer B (50 mM Tris-HCl pH 7.5, 150 mM NaCl, 5 mM EDTA, protease inhibitor cocktail EDTA-free (Roche, Mannheim, Germany), 50 µM PMSF, 0.5% NP-40). 60-100 µl slurry depending on input protein amount of pre-equilibrated anti-HA affinity matrix (Roche, Mannheim, Germany) are added and HA-tagged proteins are immunopurified with this matrix by rotating the samples over night at 4° C. The next day the beads are washed with the following buffers in this order: three times ice-cold Buffer B, one time ice-cold Buffer B NP-40 free, and three times ice-cold 15 mM TEAB pH 8.5. Spins between washes are performed at 2000 g and 4° C.

To elute the immunopurified material 35 µl of Buffer C (1 mg/ml HA peptide (ThermoScientific, Waltham, Mass.), 15 mM TEAB pH 8, 0.02% Rapigest® (Waters, Milford, Mass.) is added and the samples are incubated at 37° C. for 30 min at 1000 rpm shaking in an Eppendorf Thermomixer® (Eppendorf AG). The eluted material is cleared from the beads by adding 300 µl of 15 mM TEAB and spinning at 2600 g. The cleared material is stored at −80° C. until further processing.

Example 904

In-Gel Tryptic Digestion & Mass Spectrometric Analysis

Eluted samples were separated on 4-12% Bis. Tris gel (Life Technologies, Carlsbad, Calif.) at 160 V for 30 min. Protein bands were visualized using Simply Blue® staining solution (Life Technologies, Carlsbad) for one hour and destained in Milli-Q water for overnight. Bands were excised from top to bottom of the gel into 10 gel regions. Gel bands were further destained in 50 mM ammonium bicarbonate/50% acetonitrile (ACN) solution for 30 min followed by dehydration in 100% ACN for 10 min. Trypsin (Promega, Madison, Wis.) solution at 0.02 µg/µL was added to the gel pieces and was chilled on ice for 1 h. Excess trypsin solution was removed and tryptic digestion was performed in 25 mM ammonium bicarbonate at 37° C. overnight. Peptides were extracted with 10% ACN/0.1% trifluoroacetic acid (TFA) and dried down completely in the SpeedVac® vacuum evaporator. Peptides were reconstituted in 2% ACN/0.1% formic acid (FA) and analyzed by mass spectrometry.

Samples were injected via an auto-sampler for separation by reverse phase chromatography on a NanoAcquity® UPLC system (Waters, Dublin, Calif.). Peptides were loaded onto a C18 column (1.7 μm BEH-130, 0.1×100 mm, Waters, Dublin, Calif.) with a flow rate of 1 μL a minute and a 35-minute gradient of 2% Solvent B to 25% Solvent B (where Solvent A is 0.1% Formic acid/2% ACN/water and Solvent B is 0.1% FA/2% water/ACN). Peptides were eluted directly into an LTQ Orbitrap Elite® mass spectrometer (ThermoFisher, San Jose, Calif.). Precursor ions were analyzed in the FTMS at 60,000 resolution. MS/MS was performed in the ion trap with the instrument operated in data dependent mode whereby the top 15 most abundant ions were subjected for fragmentation.

Example 905

Data Analysis and Bioinformatics

MS/MS data was searched using the Mascot® Search Algorithm (Matrix Sciences, London, UK). Search criteria included a full MS tolerance of 50 ppm, MS/MS tolerance of 0.8 Da with oxidation of Methionine as variable modification with up to 2 missed cleavages. Data was searched against the human and contaminant subset of the Uniprot database that consists of the reverse protein sequences. Data was then filtered using Linear Discriminator Analysis (LDA) at peptide level at 5% FDR rates and further filtered using Protein FDR tool at 5% FDR (Huttlin et al. (2010) Cell 143(7):1174-1189). All peptides subsequently were subjected to quantitation of peak area under curve (AUC) with Vista (Bakalarski et al. (2008) J Proteome Res 7(11):4756-4765)

Example 906

Cellular Data Methods

Cell Lines:

All cells were obtained from American Type Culture Collection (ATCC), 10801 University Boulevard Manassas, Va. 20110 USA, unless otherwise noted. HCT WT (Human colorectal carcinoma, wild-type) parental, HCT USP7null (Horizon; HD R02-028), HCT p53null (Horizon; HD 104-001). MCF-7. MDA-MB157, U2Os, SaOs, normal mammary cells (Life Technologies; HMEC A10565), normal osteoblasts (Lonza; CC-2538), KMS-21BM, KMS-28PE (Japanese Collection of Research Bioresources Cell Bank), RKO, RKO-E6, Vibo, SiHA.

Antibodies:

USP7 (Abcam; ab84098), MDM2 (Santa Cruz; sc-965), tubulin (Licor; 926-42211), p53 (Thermo Scientific; MS738-P1), p21 (Millipore; 05-655), E6AP (Santa Cruz; sc-25509).

Compounds:

Formula I compounds, cisplatin, doxorubicin.

Cell Viability Assays:

2,500-5,000 cells were seeded in 1-well of a 96-well plate (Corning; 3904). The following day, the media was changed from normal (10%) to low serum (0.5%) containing vehicle (DMSO) or compounds. 16-24 h later FBS was added to each well to bring serum levels back to normal (10%). Cells were then allowed to grow for 2 days. All treatments were done in triplicate.

a) IncuCyte™ (Cell Density and Caspase Activity)

The day after cells were seeded, the media was changed to low serum media containing 2 μM CellEvent Caspase 3/7 reagent (Life Technologies; C10423) and compounds. The plates were placed in an IncuCyte (Essen Bioscience, Inc.) live cell imager and scanning was started 15-20 mins after. IncuCyte™ ZOOM facilitates live-cell monitoring via customized imaging protocols. Images were taken every 2 h for at least 3 days, using a 10× objective. Phase contrast was used to measure cell confluency/density while green fluorescence was used to measure caspase activity. The images were analyzed using IncuCyte software (Basic Analysis parameters) and a ratio of caspase activity to cell density was determined.

b) CellTitre-Glo (Promega; G7570)

Seventy two hours after compounds were added, CellTitre Glo (CTG) reagent was added following the protocol provided by the manufacturer (Promega). In the experiment to test compound dependency on USP7, 3× more USP7 null cells were plated per well (7,500 vs. 2,500 for wild-type (WT) cells), given the slower proliferation of USP7 null cells. For the multiple myeloma experiment, cells seeded in low serum and treated with compounds immediately. Twenty four hours later, serum was added back to normal levels. CTG assay was done 24 h later i.e. 48 h after compounds were added instead of 72 hrs later for the adherent cells.

MDM2 Turnover:

In 24-well plates, 0.15×$10^6$ MCF-7 cells were treated for a total of 8 h with DMSO or compounds (15 μM). During that 8 h, cycloheximide (CHX) was added for the indicated times prior to harvest.

Western Blots:

In 24-well plates, 0.10-0.15×$10^6$ (adherent) or 0.5×$10^6$ (suspension) cells were treated with 15 μM or 2.5 μM compounds, respectively, for 24 h in low serum prior to lysis for Western Blot analysis.

Cellular Ubiquityl-MDM2 Assay Protocol:

HCT116 colon cancer cells or SJSA-1 osteosarcoma cells were seeded at a density of 150,000 cell per well in 90 ml (RPMI 1640 media, 10% FBS, 1× GlutaMAX™, Gibco) in 96-well black clear bottom, TC-treated (Greiner, Cat#655090), and incubated for 2 hours at 37° C., 5% $CO_2$ in a tissue culture incubator. Compounds were prepared in a serial dilution in DMSO at 200× the final desired concentration in a 96-well polypropylene V-bottom (Greiner, Cat#651261), then diluted 1:20 in RPMI tissue culture medium and 10 ml transferred to each well of the cell plate. Cell plates were incubated overnight for 20 hours, 37° C., 5% $CO_2$. 20 ml of a 120 mM stock (in RPMI) of the proteasome inhibitor, MG132 (Cayman Chemical, Cat#10012628), was added to each well. Cells were incubated for 1 hour at 37° C., 5% $CO_2$. Quantitation of ubiquityl-MDM2 was carried out using Ub/Total MDM2 whole cell lysate kit (MSD, Cat#K15168D-2). Cells were lysed by adding 15 ml of 5×MSD lysis buffer (containing additives: 10 mM NaF, 10 mM beta-glycerophosphate, 1.5 mM $Na_3VO_4$, protease inhibitor cocktail (Sigma, P8340) to each well and incubated at 4° C. for 30 minutes with shaking. 100 ml of lysate was transferred to each well of the MSD 96-well plate, incubated at room temperature for 1 hour while shaking (650 RPM) in the dark. The MSD plates were washed 3 times in Tris buffered saline (50 mM Tris-Cl, pH 7.5. 150 mM NaCl) using a Biotek EL405 plate washer. 3 mls of detection antibody solution was prepared per plate (1 ml of block buffer A, 1.82 ml 1× Tris wash buffer, 150 ul 2% Blocker D-M, 30 ul 10% Blocker D-R, 60 ul 50× anti-total MDM2 antibody). 25 ml of detection antibody solution was added per well and incubated for 1 hour at room temperature (650 RPM) in the dark. Plates were washed 3 times in Tris buffered saline using a Biotek EL405 plate washer. MSD read buffer was prepared according to manufacturer's instructions and 150 ml added per well. Plates were read using a MSD Sector Reader. The final measurement was the ratio of Ubiquitinated MDM2/Total MDM2. Percentage increase in ubiquityl-MDM2 was calculated relative to DMSO controls using Genedata Screener software.

Compound 88 caused an increase in ubiquityl-MDM2 in SJSA-1 cells in low serum conditions (EC50=2 micromolar). Expression of p53 is required for full Palm site 3 compound activity in HCT116 colon cancer cells, breast cancer cells and osteosarcoma cells. USP7 expression is required for Formula I compound activity. Low MDM2 expression compromises Palm site 3 compound activity.

Formula I compounds increase p53 and p21 without stabilizing MDM2 and may combine with standard of care chemotherapeutics. Formula I compounds destabilize MDM2 and selectively inhibit endogenous USP7 DUB activity.

Example 907

Primary NMR Screen

A primary fragment screen was performed using NMR for direct binding detection. The saturation difference spectroscopy method (Mayer, M.; Meyer B. Angew. Chem., Int. Ed., 38, 1784-1788 (1999)) was applied to identify compounds in a library that interacted with the target protein. The screening library consisted of 4862 "fragments" of a molecular weight averaging approximately 250 Dalton. In a first step, mixtures of 5 fragments were measured in the presence of USP7 catalytic domain and compounds that showed binding were repeated as singles. Compounds were selected as primary binders based on the signal to noise (SINO) of >5 in the STD spectra of mixtures and a SINO of >10 from the confirmation measurements. Fragment binders were identified and confirmed in the primary screen and were followed up by addition of the primary binder to 2H/13C/15N isotope labeled USP7 protein and observation and classification of the 15N shift perturbations in TROSY-HSQC spectra (Pervushin, K., Riek, R., Wider, G. & Wüthrich, K. (1997) Proc Natl Acad Sci USA 94:12366-12371). Shift perturbations allowed grouping of scaffolds to specific binding sites based on the involved amino acids and the USP7 crystal structure. A 15N TROSY overlay shows chemical shift perturbations characteristic of fragment binding to the "palm site" of USP7.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:
1. A compound selected from Formula I:

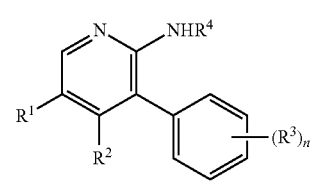

or stereoisomers, tautomers, or pharmaceutically acceptable salts thereof, wherein:
$R^1$ is selected from $C_6$-$C_{20}$ aryl, $C_3$-$C_{12}$ carbocyclyl, $C_2$-$C_{20}$ heterocyclyl, and $C_1$-$C_{20}$ heteroaryl;
$R^2$ is selected from —$CH_2CH_3$, —$CH_2CH_2CH_3$, —CH($CH_3$)$_2$, and cyclopropyl;
$R^3$ is selected from F, Cl, Br, I, —CN, —$CH_3$, —$CH_2CH_3$, —CH($CH_3$)$_2$, —$CH_2CH(CH_3)_2$, —$CH_2OH$, —$CH_2OCH_3$, —$CH_2CH_2OH$, —C($CH_3$)$_2$OH, —CH(OH)CH($CH_3$)$_2$, —C($CH_3$)$_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —CH($CH_3$)CN, —C($CH_3$)$_2$CN, —$CH_2CN$, —$CO_2H$, —$COCH_3$, —$CO_2CH_3$, —$CO_2C(CH_3)_3$, —COCH(OH)CH$_3$, —$CONH_2$, —$CONHCH_3$, —$CONHCH_2CH_3$, —CONHCH($CH_3$)$_2$, —CON($CH_3$)$_2$, —C($CH_3$)$_2CONH_2$, —$NH_2$, —$NHCH_3$, —N($CH_3$)$_2$, —$NHCOCH_3$, —N($CH_3$)$COCH_3$, —NHS(O)$_2CH_3$, —N($CH_3$)C($CH_3$)$_2CONH_2$, —N($CH_3$)$CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —S(O)$_2$N($CH_3$)$_2$, —$SCH_3$, —S(O)$_2CH_3$, —S(O)$_3$H, cyclopropyl, cyclopropylamide, oxetanyl, azetidinyl, 1-methyl-azetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;
n is selected from 0, 1, 2, and 3; and
$R^4$ is selected from H, $C_1$-$C_3$ alkyl, $C_1$-$C_3$ fluoroalkyl, cyclopropyl, and cyclopropylmethyl;
where aryl, carbocyclyl, heterocyclyl, and heteroaryl are optionally substituted with one or more groups independently selected from F, Cl, Br, I, —CN, —$CH_3$, —$CH_2CH_3$, —CH($CH_3$)$_2$, —$CH_2CH(CH_3)_2$, —$CH_2OH$, —$CH_2OCH_3$, —$CH_2CH_2OH$, —C($CH_3$)$_2$OH, —CH(OH)CH($CH_3$)$_2$, —C($CH_3$)$_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —C($CH_3$)$_2$CN, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)CH$_3$, —$CONH_2$, —$CONHCH_3$, —CON($CH_3$)$_2$, —C($CH_3$)$_2CONH_2$, —$NH_2$, —$NHCH_3$, —N($CH_3$)$_2$, —$NHCOCH_3$, —N($CH_3$)$COCH_3$, —NHS(O)$_2CH_3$, —N($CH_3$)C($CH_3$)$_2CONH_2$, —N($CH_3$)$CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —S(O)$_2$N($CH_3$)$_2$, —$SCH_3$, —S(O)$_2CH_3$, —S(O)$_3$H, cyclopropyl, cyclopropylamide, oxetanyl, azetidinyl, 1-methyl-azetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino.

2. The compound of claim 1 wherein $R^1$ is optionally substituted $C_6$-$C_{20}$ aryl.

3. The compound of claim 2 wherein $R^1$ is 4-phenol.

4. The compound of claim 1 wherein $R^1$ is optionally substituted $C_1$-$C_{20}$ heteroaryl.

5. The compound of claim 4 wherein $R^1$ is selected from 1H-indazol-5-yl, 1H-indazol-6-yl, 2-methylindazol-4-yl, 1H-benzimidazol-5-yl, 2-thienyl, pyrimidin-5-yl, 3-pyridyl, 4-pyridyl, and 1H-pyridin-2-one.

6. The compound of claim 1 wherein $R^2$ is —CH$_2$CH$_3$.

7. The compound of claim 1 wherein $R^3$ is —OH, and n is 1.

8. The compound of claim 1 wherein $R^4$ is H.

9. The compound of claim 1 selected from Formulas Ia-f:

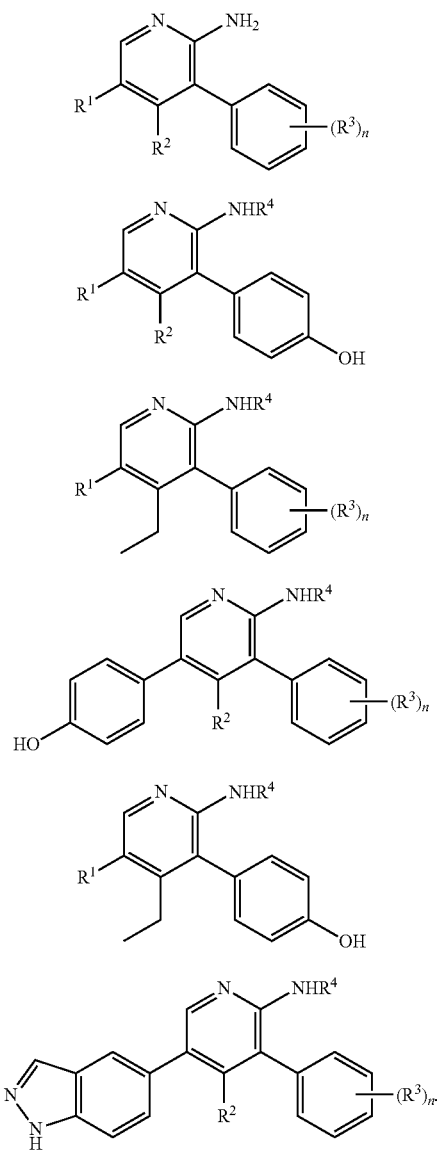

10. The compound of claim 1 selected from:
4-[6-amino-4-ethyl-5-(4-hydroxyphenyl)-3-pyridyl]phenol;
4-[6-amino-5-(4-hydroxyphenyl)-4-isopropyl-3-pyridyl]phenol;
4-[6-amino-5-(4-hydroxyphenyl)-4-propyl-3-pyridyl]phenol;
4-[6-amino-4-ethyl-5-(4-hydroxyphenyl)-3-pyridyl]-3-fluoro-phenol;
N-[3-[6-amino-4-ethyl-5-(4-hydroxyphenyl)-3-pyridyl]phenyl]acetamide;
4-[6-amino-4-cyclopropyl-5-(4-hydroxyphenyl)-3-pyridyl]phenol;
4-[6-amino-4-ethyl-5-(2-fluoro-4-methoxy-phenyl)-3-pyridyl]phenol;
4-[2-amino-4-ethyl-5-(4-hydroxyphenyl)-3-pyridyl]-3-fluoro-phenol;
4-[2-amino-5-[3-[(dimethylamino)methyl]phenyl]-4-ethyl-3-pyridyl]phenol;
N-[3-[6-amino-4-ethyl-5-(2-thienyl)-3-pyridyl]phenyl]acetamide;
N-[3-[6-amino-4-ethyl-5-(1H-indazol-6-yl)-3-pyridyl]phenyl]acetamide;
4-[4-ethyl-5-(4-hydroxyphenyl)-6-(propylamino)-3-pyridyl]phenol;
4-(6-amino-4-ethyl-5-phenyl-3-pyridyl)phenol;
4-[6-amino-4-ethyl-5-(m-tolyl)-3-pyridyl]phenol;
4-[6-amino-5-(3,4-difluorophenyl)-4-ethyl-3-pyridyl]phenol;
3-[2-amino-4-ethyl-5-(4-hydroxyphenyl)-3-pyridyl]benzonitrile;
4-[6-amino-4-ethyl-5-(4-methylsulfonylphenyl)-3-pyridyl]phenol;
tert-butyl N-[4-[2-amino-4-ethyl-5-(4-hydroxyphenyl)-3-pyridyl]phenyl]carbamate;
4-[6-amino-4-ethyl-5-(3-morpholinophenyl)-3-pyridyl]phenol;
tert-butyl N-[[3-[2-amino-4-ethyl-5-(4-hydroxyphenyl)-3-pyridyl]phenyl]methyl]carbamate;
4-[6-amino-4-ethyl-5-[3-(methoxymethyl)phenyl]-3-pyridyl]phenol;
4-[6-amino-4-ethyl-5-[4-(methoxymethyl)phenyl]-3-pyridyl]phenol;
4-[6-amino-4-ethyl-5-[3-(morpholinomethyl)phenyl]-3-pyridyl]phenol;
2-[3-[2-amino-4-ethyl-5-(4-hydroxyphenyl)-3-pyridyl]phenyl]acetonitrile;
tert-butyl N-[4-[2-amino-4-ethyl-5-(4-hydroxyphenyl)-3-pyridyl]phenyl]-N-methyl-carbamate;
5-[2-amino-4-ethyl-5-(4-hydroxyphenyl)-3-pyridyl]pyridine-3-carbonitrile;
N-[4-[2-amino-4-ethyl-5-(4-hydroxyphenyl)-3-pyridyl]phenyl]methanesulfonamide;
tert-butyl N-[3-[2-amino-4-ethyl-5-(4-hydroxyphenyl)-3-pyridyl]phenyl]carbamate;
4-(2-amino-4-ethyl-5-pyrimidin-5-yl-3-pyridyl)phenol;
4-[2-amino-4-ethyl-5-(o-tolyl)-3-pyridyl]phenol;
4-[2-amino-4-ethyl-5-(4-fluorophenyl)-3-pyridyl]phenol;
4-[2-amino-4-ethyl-5-(6-methyl-3-pyridyl)-3-pyridyl]phenol;
4-[2-amino-4-ethyl-5-(p-tolyl)-3-pyridyl]phenol;
4-(2-amino-4-ethyl-5-phenyl-3-pyridyl)phenol;
4-[2-amino-4-ethyl-5-(4-pyridyl)-3-pyridyl]phenol;
4-[2-amino-4-ethyl-5-(3-pyridyl)-3-pyridyl]phenol;
4-[6-(cyclopropylmethylamino)-4-ethyl-5-(4-hydroxyphenyl)-3-pyridyl]phenol;
N-[3-[2-amino-4-ethyl-5-(4-hydroxyphenyl)-3-pyridyl]phenyl]methanesulfonamide;
4-[2-amino-4-ethyl-5-(3-piperazin-1-ylphenyl)-3-pyridyl]phenol;

4-[4-ethyl-5-(4-hydroxyphenyl)-6-(methylamino)-3-pyridyl]phenol;
4-[2-amino-5-(4-chloro-3-methyl-phenyl)-4-ethyl-3-pyridyl]phenol;
4-[6-amino-4-ethyl-5-(4-hydroxyphenyl)-3-pyridyl]benzamide;
3-[6-amino-4-ethyl-5-(4-hydroxyphenyl)-3-pyridyl]benzamide;
4-[2-amino-4-ethyl-5-(3-isopropylphenyl)-3-pyridyl]phenol;
4-[2-amino-5-(3,4-difluorophenyl)-4-ethyl-3-pyridyl]phenol;
3-[6-amino-4-ethyl-5-(4-hydroxyphenyl)-3-pyridyl]benzonitrile;
4-[2-amino-4-ethyl-5-(2-fluorophenyl)-3-pyridyl]phenol;
4-[6-amino-4-ethyl-5-(4-hydroxyphenyl)-3-pyridyl]benzonitrile;
4-[2-amino-4-ethyl-5-(3-methoxyphenyl)-3-pyridyl]phenol;
4-[2-amino-4-ethyl-5-(4-methoxyphenyl)-3-pyridyl]phenol;
3-[6-amino-4-ethyl-5-(4-hydroxyphenyl)-3-pyridyl]-N,N-dimethyl-benzamide;
4-[2-amino-4-ethyl-5-[4-(hydroxymethyl)phenyl]-3-pyridyl]phenol;
4-[6-amino-4-ethyl-5-(4-hydroxyphenyl)-3-pyridyl]-N,N-dimethyl-benzamide;
4-[2-amino-4-ethyl-5-(m-tolyl)-3-pyridyl]phenol;
5-[6-amino-4-ethyl-5-(4-hydroxyphenyl)-3-pyridyl]-1H-pyridin-2-one;
4-[6-amino-4-ethyl-5-(3-methyl-1H-indazol-5-yl)-3-pyridyl]phenol;
[4-[6-amino-4-ethyl-5-(4-hydroxyphenyl)-3-pyridyl]phenyl]-morpholino-methanone;
4-[2-amino-5-(3-benzyloxyphenyl)-4-ethyl-3-pyridyl]phenol;
5-[6-amino-4-ethyl-5-(4-hydroxyphenyl)-3-pyridyl]pyridine-2-carbonitrile;
5-[6-amino-4-ethyl-5-(4-hydroxyphenyl)-3-pyridyl]pyridine-3-carbonitrile;
[3-[6-amino-4-ethyl-5-(4-hydroxyphenyl)-3-pyridyl]phenyl]-pyrrolidin-1-yl-methanone;
4-[6-amino-4-ethyl-5-(4-hydroxyphenyl)-3-pyridyl]-N-cyclopropyl-benzamide;
2-[3-[6-amino-4-ethyl-5-(4-hydroxyphenyl)-3-pyridyl]phenyl]acetonitrile;
4-[6-amino-4-ethyl-5-(4-hydroxyphenyl)-3-pyridyl]-2-fluoro-benzonitrile;
4-[2-amino-4-ethyl-5-(6-methoxy-3-pyridyl)-3-pyridyl]phenol;
3-[6-amino-4-ethyl-5-(4-hydroxyphenyl)-3-pyridyl]-N-isopropyl-benzamide;
N-[[4-[6-amino-4-ethyl-5-(4-hydroxyphenyl)-3-pyridyl]phenyl]methyl]methanesulfonamide;
4-[2-amino-4-ethyl-5-(1-isobutylpyrazol-4-yl)-3-pyridyl]phenol;
5-[2-amino-4-ethyl-5-(4-hydroxyphenyl)-3-pyridyl]-2-hydroxy-benzonitrile;
4-[2-amino-4-ethyl-5-(2-methyl-4-pyridyl)-3-pyridyl]phenol;
4-[2-amino-5-[3-(difluoromethyl)phenyl]-4-ethyl-3-pyridyl]phenol;
N-[5-[6-amino-4-ethyl-5-(4-hydroxyphenyl)-3-pyridyl]-2-pyridyl]acetamide;
4-[2-amino-5-(3,5-difluorophenyl)-4-ethyl-3-pyridyl]phenol;
4-[2-amino-5-(3-chlorophenyl)-4-ethyl-3-pyridyl]phenol;
4-[2-amino-5-(2-chlorophenyl)-4-ethyl-3-pyridyl]phenol;
4-[2-amino-4-ethyl-5-(4-fluoro-3-methyl-phenyl)-3-pyridyl]phenol;
4-[2-amino-5-(4-chlorophenyl)-4-ethyl-3-pyridyl]phenol;
4-[6-amino-4-ethyl-5-(4-hydroxyphenyl)-3-pyridyl]-N-methyl-benzamide;
4-[2-amino-4-ethyl-5-[3-(morpholinomethyl)phenyl]-3-pyridyl]phenol;
4-[2-amino-4-ethyl-5-(2-methoxypyrimidin-5-yl)-3-pyridyl]phenol;
4-[2-amino-4-ethyl-5-(1H-indazol-6-yl)-3-pyridyl]phenol;
4-[2-amino-4-ethyl-5-(2-methylindazol-4-yl)-3-pyridyl]phenol;
4-[2-amino-4-ethyl-5-(2-methyl-1H-benzimidazol-5-yl)-3-pyridyl]phenol;
4-[6-amino-4-ethyl-5-(1H-indazol-5-yl)-3-pyridyl]phenol;
4-[2-amino-4-ethyl-5-(1H-indazol-5-yl)-3-pyridyl]phenol;
4-[2-amino-4-ethyl-5-(2-methylindazol-6-yl)-3-pyridyl]phenol;
4-[2-amino-5-(3-aminophenyl)-4-ethyl-3-pyridyl]phenol;
4-[2-amino-5-(4-aminophenyl)-4-ethyl-3-pyridyl]phenol;
5-[6-amino-4-ethyl-5-(4-hydroxyphenyl)-3-pyridyl]-N-methyl-pyridine-2-carboxamide;
4-[6-amino-4-ethyl-5-(1H-indazol-6-yl)-3-pyridyl]phenol;
5-[6-amino-4-ethyl-5-(4-hydroxyphenyl)-3-pyridyl]-2-hydroxy-benzonitrile; and
5-[6-amino-4-ethyl-5-(4-hydroxyphenyl)-3-pyridyl]-2-hydroxy-benzamide.

11. A pharmaceutical composition comprised of a compound of claim 1 and a pharmaceutically acceptable carrier, glidant, diluent, or excipient.

12. The pharmaceutical composition according to claim 11, further comprising a therapeutic agent.

* * * * *